US008586567B2

(12) United States Patent
Sampalis et al.

(10) Patent No.: US 8,586,567 B2
(45) Date of Patent: Nov. 19, 2013

(54) CONCENTRATED THERAPEUTIC PHOSPHOLIPID COMPOSITIONS

(75) Inventors: Fotini Sampalis, Laval (CA); Henri Harland, Rosemere (CA)

(73) Assignee: Acasti Pharma, Inc., Laval (CA)

( * ) Notice: Subject to any disclaimer, the term of this patent is extended or adjusted under 35 U.S.C. 154(b) by 0 days.

(21) Appl. No.: 12/915,724

(22) Filed: Oct. 29, 2010

(65) Prior Publication Data

US 2011/0160161 A1 Jun. 30, 2011

Related U.S. Application Data

(60) Provisional application No. 61/256,106, filed on Oct. 29, 2009.

(51) Int. Cl.
*A61K 31/661* (2006.01)
*A61K 31/215* (2006.01)
*A61K 31/131* (2006.01)

(52) U.S. Cl.
USPC ............................ 514/120; 514/667; 514/506

(58) Field of Classification Search
None
See application file for complete search history.

(56) References Cited

U.S. PATENT DOCUMENTS

| | | | |
|---|---|---|---|
| 4,331,695 | A | 5/1982 | Zosel |
| 4,915,876 | A | 4/1990 | Lindsay |
| 4,963,527 | A | 10/1990 | Bombardelli et al. |
| 5,006,281 | A | 4/1991 | Rubin et al. |
| 5,434,183 | A | 7/1995 | Larsson-Backstrom |
| 6,055,936 | A | 5/2000 | Collin |
| 6,265,450 | B1 | 7/2001 | Asami et al. |
| 6,521,768 | B2 | 2/2003 | Beaudoin |
| 6,713,447 | B2 | 3/2004 | Beaudoin |
| 7,034,168 | B2 | 4/2006 | Basheer |
| 7,572,464 | B2 | 8/2009 | Chandler |
| 7,935,365 | B2 | 5/2011 | Dror |
| 8,030,348 | B2 | 10/2011 | Sampalis |
| 8,057,825 | B2 | 11/2011 | Sampalis |
| 2008/0274203 | A1 | 11/2008 | Bruheim |
| 2011/0104297 | A1 | 5/2011 | Bruheim |

FOREIGN PATENT DOCUMENTS

| | | |
|---|---|---|
| AU | 671329 B | 8/1996 |
| CA | 1098900 A | 4/1981 |
| CA | 2115571 A1 | 12/1993 |
| CA | 2 251 265 A1 | 4/2000 |
| CA | 2 362 663 A1 | 6/2001 |
| EP | 0 275 005 A2 | 7/1988 |
| EP | 0 209 037 B1 | 2/1990 |
| EP | 0 507 363 B1 | 5/1993 |
| EP | 0 275 224 B1 | 7/1993 |
| EP | 0 609 078 A1 | 8/1994 |
| EP | 0 209 038 B2 | 3/1996 |
| EP | 0 732 378 A2 | 9/1996 |
| EP | 0 773 283 B1 | 7/1999 |
| ES | 2 088 750 B1 | 3/1997 |
| JP | 51-76467 | 7/1976 |
| JP | 53-112195 | 9/1978 |
| JP | 55-23949 A | 2/1980 |
| JP | 59-196032 A | 11/1984 |
| JP | 60-03507 A | 2/1985 |
| JP | 60-153779 A | 8/1985 |
| JP | S6323819 | 7/1986 |
| JP | 63-295698 | 12/1988 |
| JP | 64-50890 A | 2/1989 |
| JP | 02-167055 | 6/1990 |
| JP | 2-215351 A | 8/1990 |
| JP | 4-57853 A | 2/1992 |
| JP | 04-273817 | 9/1992 |
| JP | 06-237703 | 8/1994 |
| JP | 8-198754 A | 8/1996 |
| JP | 8-302382 A | 11/1996 |
| JP | 2909508 B2 | 6/1999 |
| JP | 2000-60432 A | 2/2000 |
| KR | 2002037140 | 5/2002 |
| NO | 147365 B | 12/1982 |
| WO | WO 84/01715 A1 | 5/1984 |
| WO | WO 92/21335 A1 | 12/1992 |
| WO | WO 96/37200 A1 | 11/1996 |
| WO | WO 97/39759 A2 | 10/1997 |
| WO | WO 99/64547 A1 | 12/1999 |
| WO | WO 00/23546 A1 | 4/2000 |
| WO | WO 00/44862 A1 | 8/2000 |
| WO | WO 02/092540 | 11/2002 |
| WO | WO 02/102394 | 12/2002 |
| WO | WO 03/011873 A2 | 2/2003 |
| WO | WO 2008/060163 A1 | 5/2008 |
| WO | WO 2008/117062 A1 | 10/2008 |

OTHER PUBLICATIONS

U.S. Appl. No. 60/307,842, filed Jul. 7, 2001, Sampalis.
U.S. Appl. No. 60/298,383, filed Jun. 18, 2001, Sampalis.
"Neptune Technologies IPO Warmly Received in Cool Financial Climate," Extract from Canadian Corporate Newswire, (Jun. 7, 2001).
Araki et al., "Positional Distribution of Fatty Acids in Glycerolipids of the Marine Red Alga, *Porphyra yezoensis*," Plant Cell Physiol. 28(5):761-766 (1987).
Aureli et al., "Aging brain: effect of acetyl-L-carnitine treatment on rat brain energy and phospholipid metabolism. A study by $^{31}$P and $^{1}$H NMR spectroscopy," Brain Research 526(1):108-112 (1990).
Barak et al., "Inositol Treatment of Alzheimer's Disease: A Double Blind, Cross-Over Placebo Controlled Trial," Prog. Neuro-Psychopharmacol. Biol. Psychiat. 20:729-735 (1996).

(Continued)

*Primary Examiner* — Savitha Rao
*Assistant Examiner* — Gregg Polansky
(74) *Attorney, Agent, or Firm* — Cooley LLP

(57) ABSTRACT

The invention relates to concentrated therapeutic phospholipid compositions; methods for treating or preventing diseases associated with cardiovascular disease, metabolic syndrome, inflammation and diseases associated therewith, neurodevelopmental diseases, and neurodegenerative diseases, comprising administering an effective amount of a concentrated therapeutic phospholipid composition.

14 Claims, 38 Drawing Sheets

(56) References Cited

OTHER PUBLICATIONS

Barkai et al., "Reduced Myo-Inositol Levels in Cerebrospinal Fluid from Patients with Affective Disorder," Biol. Psychiatry 13:65-72 (1978).
Basile et al., "Antibacterial activity of pure flavonoids isolated from mosses," Phytochemistry 52(8):1479-1482 (1999).
Bast and Haenen, "Interplay between lipoic acid and glutathione in the protection against microsomal lipid peroxidation," Biochem. Biophys. Acta. 963:558-561 (1988).
Bell and Dick, "Molecular Species Composition of the Major Diacyl Glycerophospholipids from Muscle, Liver, Retina and Brain of Cod (*Gadus morhua*)," Lipids 26(8):565-573 (1991).
Benjamin et al., "Double-blind, placebo-controlled, crossover trial of inositol treatment for panic disorder," Am. J. Psychiatry 15:1084-1086 (1995).
Berkow, R., "Generalized Cardiovascular Disorders," The Merck Manual of Diagnosis and Therapy, Chapter 24, Merck Research Laboratories, Rahway, NJ, USA: pp. 409-431 (1992).
Birchall and Chappell, "Aluminium, Chemical Physiology, and Alzheimer's Disease," Lancet 29:1008-1010 (1988).
Bowyer et al., "The Determination of the Fatty Acid Composition of Serum Lipids Separated by Thin-Layer Chromatography; and a Comparison with Column Chromatography," Biochim. Biophys. Acta 70:423-431 (1963).
Burgess et al., "Long-chain polyunsaturated fatty acids in children with attention-deficit hyperactivity disorder," Am. J. Clin. Nutr. 71(suppl):327S-330S (2000).
Caprioli et al., "Age-Dependent Deficits in Radial Maze Performance in the Rat: Effect of Chronic Treatment with Acetyl-L-Carnitine," Prog. Neuro-Psychopharmacol. Biol, Psychiat. 14(3):359-369 (1990).
Carell et al., "A Novel Procedure for the Synthesis of Libraries Containing Small Organic Molecules," Angew. Chem. Int. Ed. Engl. 33(20):2059-2061 (1994).
Carell et al., "A Solution-Phase Screening Procedure for the Isolation of Active Compounds from a Library of Molecules," Angew. Chem. Int. Ed. Engl. 33(20):2061-2064 (1994).
Cenacchi et al., "Cognitive decline in the elderly: A double-blind, placebo-controlled multicenter study on efficacy of phosphatidylserine administration," Aging Clin. Exp. Res. 5:123-133 (1993).
Chandrasekar et al., "Tissue Specific Regulation of Transforming Growth Factor Beta by Omega-3 Lipid-Rich Krill Oil in Autoimmune Murine Lupus," Nutr. Res. 16(3):489-503 (1996).
Château et al., "Dimethyl sulfoxide-induced apoptosis in human leukemic U937 cells," Anal. Cell. Pathol. 10:75-84 (1996).
Cheng et al., "Huperzine A, a novel promising acetylcholinesterase inhibitor," NeuroReport 8:97-101 (1996).
Christensen et al., "Lymphatic absorption of n-3 polyunsaturated fatty acids from marine oils with different intramolecular fatty acid distributions," Biochim. Biophys. Acta 1215:198-204 (1994).
Church et al., "Spectrophotometric Assay Using o-Phthaldialdehyde for Determination of Proteolysis in Milk and Isolated Milk Proteins," J. Dairy Sci. 66:1219-1227 (1983).
Cohen et al., "Brain Choline Uptake and Cognitive Function in Middle Age," Biol. Psych. 41:90S, Abstract No. 307 (1997).
Cohen et al., "Inositol has behavioral effects with adaptation after chronic administration," J. Neural Transm. 104:299-305 (1997).
Colodny and Hoffman, "Inositol—Clinical Applications for Exogenous Use," Altern. Med. Rev. 3(6):432-447 (1998).
Crook et al., "Effects of phosphatidylserine in age-associated memory impairment," Neurology 41:644-649 (1991).
Dawson et al., "8 Lipids and long-chain fatty acids," pp. 181-184, in Data for Biochemical Research, 3rd Edition (1986).
Delwaide et al., "Double-blind randomized controlled study of phosphatidylserine in senile demented patients," Acta Neurol. Scand. 73:136-140 (1986).
Deutch, "Menstrual pain in Danish women correlated with low n-3 polyunsaturated fatty acid intake," Eur. J. Clin. Nutr. 49(7):508-516 (1995).
Devasagayam et al., "Prevention of Singlet Oxygen-Induced DNA Damage by Lipoate," Chem.-Biol. Interactions 86:79-92 (1993).
Edwards et al., "Omega-3 polyunsaturated fatty acid levels in the diet and in red blood cell membranes of depressed patients," J. Affect. Disord. 48(2-3):149-155 (1998).
Estiarte et al., "Free-air $CO_2$ enrichment of wheat: leaf flavonoid concentration throughout the growth cycle," Physiologia Plantarum 105(3):423-433 (1999).
Folch et al., "A Simple Method for the Isolation and Purification of Total Lipides from Animal Tissues," J. Biol. Chem. 226:497-509 (1957).
Gadaleta et al., "Mitochondrial DNA Transcription and Translation in Aged Rat. Effect of Acetyl-L-carnitine," Ann. N.Y. Acad. Sci. 717:150-160 (1994).
Ghirardi et al., "Effect of Acetyl-L-Carnitine Chronic Treatment on Discrimination Models in Aged Rats," Physiol. Behav. 44(6):769-773 (1988).
Gill et al., "Calcium signalling mechanisms in endoplasmic reticulum activated by inositol 1,4,5-triphosphate and GTP," Cell Calcium 10:363-374 (1989).
Hanahan and Thompson, "Complex Lipids," Ann. Rev. Biochem. 32:215-240 (1963).
Henderson et al., "Lipid Composition of the Pineal Organ from Rainbow Trout (*Oncorhynchus mykiss*)," Lipids 29(5):311-317 (1994).
Hosokawa et al., "Conversion to Docosahexaenoic Acid-Containing Phosphatidylserine from Squid Skin Lecithin by Phospholipase D-Mediated Transphosphatidylation," J. Agric. Food Chem. 48(10):4550-4554 (2000).
Houghten et al., "The Use of Synthetic Peptide Combinatorial Libraries for the Identification of Bioactive Peptides," BioTechniques 13(3):412-421 (1992).
Ikeda et al., "Effects of Long-Term Feeding of Marine Oils with Different Positional Distribution of Eicosapentaenoic and Docosahexaenoic Acids on Lipid Metabolism, Eicosanoid Production, and Platelet Aggregation in Hypercholesterolemic Rats," Lipids 33(9):897-904 (1998).
Imperato et al., "Acetyl-L-carnitine enhances acetylcholine release in the striatum and hippocampus of awake freely moving rats,"Neurosci. Lett. 107(1-3):251-255 (1989).
Kagan et al., "Dihydrolipoic Acid—A Universal Antioxidant Both in the Membrane and in the Aqueous Phase. Reduction of Peroxyl, Ascorbyl and chromanoxyl Radicals," Biochem. Pharmacol 44:1637-1649 (1992).
Kalmijn et al., "Polyunsaturated Fatty Acids, Antioxidants, and Cognitive Function in Very Old Men," Am. J. Epidemiol. 145(1):33-41 (1997).
Kalmijn et al., "Dietary Fat Intake and the Risk of Incident Dementia in the Rotterdam Study," Ann. Neurol. 42:776-782 (1997).
Kawakami et al., "The Rationale for E2020 as a Potent Acetylcholinesterase Inhibitor," Bioorg. Med. Chem. 4:1429-1446 (1996).
Kidd, "Phosphatidylcholine: A Superior Protectant Against Liver Damage," Alt. Med. Rev. 1:258-274 (1996).
Kitamura et al., "Inhibition of myo-inositol transport causes acute renal failure with selective medullary injury in the rat," Kidney Int. 53:146-153 (1998).
Knopman et al., "Long-term tacrine (Cognex) treatment: Effects on nursing home placement and mortality, tacrine study group" Neurology 47:166-177 (1996).
Kojima et al., "Different Changes in Expression and Function of Connexin 26 and Connexin 32 During DNA Synthesis and Redifferentiation in Primary Rat Hepatocytes Using a DMSO Culture System," Hepatology 26(3):585-597 (1997).
Kristensen et al., "Dietary supplementation with n-3 polyunsaturated fatty acids and human platelet function: a review with particular emphasis on implications for cardiovascular disease," J. Intern. Med. 225(Suppl. 1):141-150 (1989).

(56) References Cited

OTHER PUBLICATIONS

Lam, "Application of combinatorial library methods in cancer research and drug discovery," Anti-Cancer Drug Design 12:145-167 (1997).
Levine et al., "Double-blind, controlled trial of inositol treatment of depression," Am. J. Psychiatr. 152:792-794 (1995).
Levine et al., "Follow-up and Relapse Analysis of an Inositol Study of Depression," Isr. J. Psychiatry Relat. Sci. 32:14-21 (1995).
Levine et al., "Inositol treatment raises CSF inositol levels," Brain Res. 627:168-170 (1993).
Levine, "Controlled trials of inositol in psychiatry," Eur. Neuropsychopharmacol. 7:147-155 (1997).
Markham et al., "Luteolin 7-Glucuronide-3'-Mono(trans)ferulylglucoside and other Unusual Flavonoids in the Aquatic Liverwort Complex, *Riccia fluitans*," Phytochemistry 17:1601-1604 (1978).
McCormick and Mabry, "The Flavonoids of *Passiflora sexflora*," J. Nat. Prod. 45(6):782 (1982).
Mills et al., "Dietary N-6 and N-3 Fatty Acids and Salt-induced Hypertension in the Borderline Hypertensive Rat," Lipids 24(1):17-24 (1989).
Mohr et al., "Treatment of Alzheimer's Disease with Sabeluzole: Functional and Structural Correlates," Clin. Neuropharmacol. 20:338-345 (1997).
Mori et al., "Purified eicosapentaenoic and docosahexaenoic acids have differential effects on serum lipids and lipoproteins, LDL particle size, glucose, and insulin in mildly hyperlipidemic men," Am. J. Clin. Nutr. 71:1085-1094 (2000).
Navarra and Lipkowitz, pp. 134, 141-142 in Encyclopedia of Vitamins, Minerals and Supplements (1996).
Newberne et al., "Lipotropes, Immunocompetence, and Cancer," Cancer Res. 43(Suppl.):2426s-2434s (1983).
Paradies et al., "Carnitine-acylcarnitine translocase activity in cardiac mitochondria from aged rats: the effect of acetyl-L-carnitine," Mech. Aging Develop. 84(2):103-112 (1995).
Parthasarathy et al., "Biochemical and Molecular Properties of Lithium-Sensitive Myo-Inositol Monophosphatase," Life Sci. 54(16):1127-1142 (1994).
Prados et al., "Actin, Tropomyosin and α-Actinin as Markers of Differentiation in Human Rhabdomyosarcoma Cell Lines Induced with Dimethyl Sulfoxide," Cell. Mol. Biol. 39(5):525-536 (1993).
Prentice et al., "Nerve growth factor-induced changes in neural cell adhesion molecule (N-CAM) in PC12 cells," EMBO J. 6(7):1859-1863 (1987).
Raa and Hansen, "Isolation of astaxanthin from crayfish or shrimp waste for use as a coloring agent in fish feed," Chem. Abstracts 98:177859m (1983).
Rao et al., "Phytochemical Investigation on Leaves of *Rhynchosia densiflora*," Indian J. Nat. Prod. 14(1):20-22 (1998).
Rogers and Adelstein, "MaxEPA Fish Oil Enhances Cholesterol-induced Intimal Foam Cell Formation in Rabbits," Am. J. Pathol. 137(4):945-951 (1990).
Rogers et al., "The Efficacy and Safety of Donepezil in Patients with Alzheimer's Disease: Results of a US Multicentre, Randomized, Double-Blind, Placebo-Controlled Trial," Dementia 7:293-303 (1996).
Sargent, "Fish oils and human diet," Br. J. Nutr. 78(Suppl. 1):S5-S13 (1997).
Saynor and Gillott, "Changes in Blood Lipids and Fibrinogen with a Note on Safety in a Long Term Study on the Effects of n-3 Fatty Acids in Subjects Receiving Fish Oil Supplements and Followed for Seven Years," Lipids 27(7):533-538 (1992).
Schneider et al., "Potential Role for Estrogen Replacement in the Treatment of Alzheimer's Dementia," Am. J. Med. 103(3A):46S-50S (1997).
Seidman et al., "Biologic Activity of Mitochondrial Metabolites on Aging and Age-Related Hearing Loss," Am. J. Otol. 21:161-167 (2000).

Seidman, "Polyunsaturated Phosphatidylcholine in NT Factor™ Improves Mitochondrial Function, Auditory Sensitivity and May Slow Some Aspects of the Aging Process," Anti-Aging Medical News, pp. 5, 16-19 (2001).
Serbinova et al., "Thioctic Acid Protects Against Ischemia-Reperfusion Injury in the Isolated Perfused Langendorff Heart," Free Rad. Res. Commun. 17:49-58 (1992).
Sharaf, "Isoscutellarein 8-O-(6"-trans-p-coumaroyl)-β-D-glucoside from *Stachys aegyptiaca*," Fitoterapia 69(4):355-357 (1998).
Simopoulos, "Omega-3 fatty acids in health and disease and in growth and development," Am. J. Clin. Nutr. 54:438-463 (1991).
Sjölander and Urbaniczky, "Integrated Fluid Handling System for Biomolecular Interaction Analysis," Anal. Chem. 63(29):2338-2345 (1991).
Stoll et al., "Omega-3 fatty acids and bipolar disorder: a review," Prostagland. Leukotrienes Essent. Fatty Acids 60(5&6):329-337 (1999).
Suzuki and Shibata, "The utilization of Antarctic krill for human food," Food Rev. Int. 6(1):119-147 (1990).
Suzuki et al., "α-Lipoic acid is a potent inhibitor of NF-κB activation in human T cells," Biochem. Biophys. Res. Commun. 189:1709-1715 (1992).
Szabo et al., "Surface plasmon resonance and its use in biomolecular interaction analysis (BIA)," Curr. Opin. Struct. Biol. 5:699-705 (1995).
Tokunaga et al., "Formation of Dimethyl Sulfide in Antarctic Krill," Bull Jpn. Soc. Sci. Fisheries 43(10):1209-1217 (1977).
Trubiani et al., "The c-myc gene regulates the polyamine pathway in DMSO-induced apoptosis," Cell Prolif. 32:119-129 (1999).
Vadnal et al., "Role of Inositol in the Treatment of Psychiatric Disorders. Basic and Clinical Aspects," CNS Drugs 7:6-16 (1997).
van Dyck et al., "The acetylcholine releaser linopirdine increases parietal regional cerebral blood flow in Alzheimer's disease," Psychopharmacology 132:217-226 (1997).
Wiegand and Anderson, "Phospholipid Molecular Species of Frog Rod Outer Segment Membranes," Exp. Eye Res. 37(2):159-173 (1983).
Yamaguchi et al., "Supercritical Carbon Dioxide Extraction of Oils from Antarctic Krill," J. Agric. Food Chem. 34:904-907 (1986).
Yarochkin et al., "Technochemical Characteristics of the Canned Food 'Natural Antarctic Krill Meat' and Its Food Value," Voprosy pitaniia Mar.-Apr.(2):69-72 (1985).
Yongmanitchai and Ward, "Positional distribution of fatty acids, and molecular species of polar lipids, in the diatom *Phaeodactylum tricornutum*," J. Gen. Microbiol. 139:465-472 (1993).
Youdim et al., "Essential fatty acids and the brain: possible health implications," Int. J. Devl. Neuroscience 18(4-5):383-399 (2000).
Fricke et al., "Lipid, Sterol and Fatty Acid Composition of Antarctic Krill," Lipids, 19(11):821-827 (1984).
Gordeev et al., "Fatty Acid Composition of the Main Phospholipids of the Antarctic Krill *Euphausia superba*," translated from Khimiya Prirodnykh Soedinenii, No. 2, 181-187 (1990).
Kuroda et al., "Comparison of Hypocholesterolemic Effect among Three Phospholipids Containing Different Fatty Acid and the Related Oils in Rats," Jpn. J. Nutr., 48(5):213-220 (1990).
Makuta et al., "Effects of EPA and Use in Health Foods," Japan Food Science 25(1):29-35 (1986).
Aker Biomarine's Corrected Request for Reexamination of Patent No. 8,030,348 (U.S. Appl. No. 95/001,774), Oct. 19, 2011.
Declaration of Bjorn Ole Haugsgjerd, submitted in Aker Biomarine's Corrected Request for Reexamination of Patent No. 8,030,348 (U.S. Appl. No. 95/001,774), Oct. 4, 2011.
Declaration of Thomas Gundersen, submitted in Aker Biomarine's Corrected Request for Reexamination of Patent No. 8,030,348 (U.S. Appl. No. 95/001,774), Oct. 4, 2011.
Non Final Office Action issued in the Reexamination of Patent No. 8,030,348 (U.S. Appl. No. 95/001,774), Dec. 19, 2011.
Aker Biomarine's Corrected Request for Reexamination of Patent No. 8,057,825 (U.S. Appl. No. 95/001,819), Dec. 16, 2011.
Declaration of Nils Hoem, submitted in Aker Biomarine's Corrected Request for Reexamination of Patent No. 8,057,825 (U.S. Appl. No. 95/001,819), Sep. 16, 2011.

(56) References Cited

OTHER PUBLICATIONS

Complaint filed by Neptune in *Neptune Technologies v. Aker Biomarine ASA, et al.*—Case 1:11-cv-00894-UNA Oct. 4, 2011.
Answer filed by Aker/Schiff in *Neptune Technologies v. Aker Biomarine ASA, et al.*—Case 1:11-cv-00894-GMS, Dec. 19, 2011.
Complaint filed by Neptune in *Neptune Technologies v. Enzymotec Limited, et al.*—Case 1:11-cv-00895-UNA, Oct. 4, 2011.
Answer filed by Enzymotec in *Neptune Technologies v. Enzymotec Limited, et al.*—Case 1:11-cv-00895-GMS, Dec. 30, 2011.
Answer filed by Mercola in *Neptune Technologies v. Enzymotec Limited, et al.*—Case 1:11-cv-00895-GMS, Dec. 30, 2011.
Request for Opposition of EP 1417211 submittted by Aker Biomarine (Feb. 29, 2008).
Request for Opposition of EP 1417211 submittted by Enzymotec Technologies (Feb. 29, 2008).
Decision of Board in Opposition of EP 1417211 (Dec. 30, 2009).
Aker Biomarine's Request for Oppostion of accepted application AU 2002322233 (Apr. 22, 2009).
Aker Biomarine's Submission of Experimental Report on Flavonoid Analysis by Professor Andersen (Feb. 29, 2008) in Opposition to EP 1417211.
Extract from an interview by the inventor, Fontini Sampalis (2005).
Sampalis et al., "Evaluation of the Effects of Neptune Krill Oil™ on the Management of Premenstrual Syndrome and Dysmenorrhea," Alternative Medicine Review 8(2), 171-179 (2003).
Extract from online KEGG database for Lucenin-2, Feb. 5, 2005.
Levy et al., "The novel Flavonoid Chemistry and Phylogenetic Origin of Phlox Floridana," Evolution 29:487-499 (Sep. 1975).
Bandyukov et al., "Natural Flavonoid C-Glycosides," Chemistry of Natural Compounds, vol. 17, No. 1 Jan.-Feb. 1981—Translated from Khimiya Prirodnykh Soedinenii, No. 1, pp. 5-24.
Voirin et al., "Separation of Flavone C-Glycosides and Qualitative Analysis of *Passiflora incarnata* L. By Capillary Zone Electrophoresis," Phytochem. Anal. 11, 90-98 (2000).
Iwashina, "The Structure and Distribution of the Flavonoids in Plants," J. Plant Res. 113:287-299 (2000).
Jay, "C-Glycosylflavonoids," The Flavonoids: Advances in Research Since 1986, Ed. J.B. Harborne, Chapter 3 (1994), ISBN 0 412 480700 (1993).
Webpage www.naturalnutritionals.com/kri14.html, Downloaded Jan. 23, 2008.
Definition of "aglycon," IUPAC Compendium of Chemical Terminology, 2nd Edition, ISBN 0865426848 (1997).
Enzymotec's Submission of a Letter from Igal Gozlan of the Tami-IMI Institute of Research and Development to Enzymotec Ltd. (Jan. 14, 2008) in Opposition to EP 1417211.
Pages from www.seakrill.com with publications (computer translations from Spanish to English) (Sep. 1997 and Oct. 1999).
Medina et al., "$^{13}$C Nuclear magnetic resonance monitoring of free fatty acid release after fish thermal processing" *J Amer. Oil Chem. Soc.* 71(5): 479-482 (1994).
Grit et al., "Hydrolysis of Phosphatidylcholine in Aqueous Liposome Dispersions" *Int. J. Pharmaceutics* 50: 1-6 (1989).
Herman and Groves, "The Influence of Free Fatty Acid Formation on the pH of Phospholipid-Stabilized Triglyceride Emulsions" *Pharmaceutical Research* 10(5): 774-776 (1993).
Singh and Heldman, *Introduction to Food Engineering* (3rd ed.), New York, NY: Academic Press, 2008 (pp. 222-227).
Heldman and Lund, *Handbook of Food Engineering*, New York, NY: Marcel Dekker, 1992 (pp. 247-259).
Hughes et al., "Determination of Carryover and Contamination for Mass Spectrometry—Based Chromatographic Assay" *The AAPS Journal*; 9 (3) Article 42, E353-60 (2007).
Elliott et al., Current Trends in Quantitative Proteomics. *J. Mass. Spectrom.*, 44 (12): 1637-1660 (2009).
Gigliotti et al. "Extraction and Characterisation of Lipids from Antarctic Krill (*Euphausia superba*)" Food Chemistry 125(3): 1028-1036 (Apr. 2011).
Kassis et al., "Characterization of Lipids and Antioxidant Capacity of Novel Nutraceutical Egg Products Developed with Omega-2-Rich Oils" J Sci Food Agr 92(1): 66-73 (2012).
O'Doherty et al., "Role of Luminal Lecithin in Intestinal Fat Absorption" Lipids 8: 249-55 (1973).
Mattson et al. "The Digestion and Absorption of Triglycerides" J Biol Chem 239:2772-7 (1964).
Tso et al., "Evidence for Separate Pathways of Chylomicron and Very Low-Density Lipoprotein Assembly and Transport by Rat Small Intestine" Am J Physiol 247: G599-G610 (1984).
Carnielli et al. "Intestinal absorption of long-chain polyunsaturated fatty acids in preterm infants fed breast milk or formula" Am J Clin Nutr 67:97-103 (1998).
Bottino et al., "Resistance of Certain Longchain Polyunsaturated Fatty Acids of Marine Oils to Pancreatic Lipase Hydrolysis" Lipids 2, 489-93 (1967).
Hernell et al., "Does the Bile Salt-Stimulated Lipase of Human Milk Have a Role in the Use of the Milk Long-Chain Polyunsaturated Fatty Acids?" J Pediatr Gastroenterol Nutr 16: 426-31 (1993).
Morgan et al. "Fatty Acid Balance Studies in Term Infants Fed Formula Milk Containing Long-Chain Polyunsaturated Fatty Acids" Acta Paediatr 87: 136-42 (1998).
Simopoulos, "Omega-3 Fatty Acids in Inflammation and Autoimmune Diseases" J Am Coll Nutr 21(6): 495-505 (2002).
Hong et al., "Novel Docosatrienes and 17S-resolvings Generated from Docosahexaenoic Acid in Murine Brain, Human Blood, and Glial Cells. Autacoids in Anti-Inflammation" J Biol Chem 278(17): 14677-87 (2003).
Tou et al., "Krill for Human Consumption: Nutritional Value and Potential Health Benefits" Nutr Rev 65(2): 63-77 (2007).
Bunea et al., "Evaluation of the Effects of Neptune Krill Oil on the Clinical Course of Hyperlipidemia" Altern Med Rev 9: 420-28 (2004).
Bridges et al., "Determination of Digestibility, Tissue Deposition, and Metabolism of the Omega-3 Fatty Acid Content of Krill Protein Concentrate in Growing Rats" J Agric Food Chem 58: 2830-7 (2010).
Ulven et al., "Metabolic Effects of Krill Oil are Essentially Similar to Those of Fish Oil But at Lower Dose of EPA and DHA, in Health Volunteers" Lipids 46: 37-46 (2011).
Sampalis et al., "Evaluation of the Effects of Neptune Krill Oil™ on the Management of Premenstrual Syndrome and Dysmenorrheal" Altern Med Rev 8: 171-9 (2003).
GRAS Notice for Aker Biomarine Antarctic AS, Dec. 14, 2010.
Winther et al., Elucidation of Phosphatidylcholine Composition in Krill Oil Extracted from *Euphausia superba* Lipids 46(1): 25-36 (2011).
Aid et al, "Dietary Docosahexaenoic Acid [22: 6(n-3)] as a Phospholipid or a Triglyceride Enhances the Potassium Chloride—Evoked Release of Acetylcholine in Rat Hippocampus. " J Nutr;135:1008-13 ( 2005).
Barberger-Gateau P, et al. "Fish, meat, and risk of dementia: cohort study." BMJ. Oct. 26;325(7370):932-3 (2002).
Bazan NG. "Synaptic lipid signaling: significance of polyunsaturated fatty acids and platelet-activating factor." J Lipid Res. Dec. 2003;44(12):2221-33. Epub (2003).
Bourre et al., "Dietary omega-3 Fatty acids and psychiatry: mood, behaviour, stress, depression, dementia and aging." J Nutr Health Aging.;9(1):31-8 (2005).
Calon F, Cole G. "Neuroprotective action of omega-3 polyunsaturated fatty acids against neurodegenerative diseases: evidence from animal studies. Prostaglandins Leukot Essent Fatty Acids." 77(5-6):287-93. Epub (2007).
Calon et al., "Docosahexaenoic Acid Protects from Dendritic Pathology in an Alzheimer's Disease Mouse Model". Neuron, vol. 43, Issue 5, 633-645, (2004).
Favreliere, S., et al. "Age-related changes in ethanolamine glycerophospholipids fatty acid levels in rat frontal cortex and hippocampus." Neurobiology of Aging, 21, 653-660 (2000).
Freund-Levi Y, et al. "ω-3 Fatty Acid Treatment in 174 Patients With Mild to Moderate Alzheimer Disease: A Randomized Double-blind Trial" Arch Neurol.;63(10):1402-1408 (2006).

(56) References Cited

OTHER PUBLICATIONS

Grant, W.B., et al. (2002). "The significance of environmental factors in the etiology of Alzheimer's disease." J. Alzheimers Dis. 4, 179-189.

Grupp et al., "Protection against Hypoxia-reoxygenation in the Absence of Poly (AOP-ribose) Synthetase in Isolated Working Hearts" J. Mol. Cell. Cardiol. 31: 297-303 (1999).

Harris, "The omega-3 index: clinical utility for therapeutic intervention." Curr Cardiol Rep. Nov. 2010;12(6):503-8 (2010).

Hebert et al., "Alzheimer Disease in the US PopulationPrevalence Estimates Using the 2000 Census" *Arch Neurol*. 2003;60(8):1119-1122 (2003).

Kuo YM, et al. "Water-soluble Abeta (N-40, N-42) oligomers in normal and Alzheimer disease brains." J Biol Chem 271:4077-4081(1996).

Lim et al. "The curry spice curcumin reduces oxidative damageand amyloid pathology in an Alzheimer transgenic mouse." J. Neurosci. 21, 8370-8377 (2001).

Lucien FP, et al. "Separation of biomolecules using supercritical fluid extraction." Australas Biotechnol. May-Jun. 1993;3(3):143-147.

Lukiw et al., "A role for docosahexaenoic acid—derived neuroprotectin D1 in neural cell survival and Alzheimer disease." J. Clin. Invest. 115:2774-2783 (2005).

Montine et al., "Isoprostanes and related products of lipid peroxidation in neurodegenerative diseases." Chem. Phys. Lipids 128, 117-124 (2004).

Morris et al "Consumption of fish and n-3 fatty acids and risk of incident Alzheimer disease." Arch Neurol 60: 940-946 (2003).

Morris et al., "Relation of the tocopherol forms to incident Alzheimer disease and to cognitive change" Am J Clin Nutr 2005;81:508-14 (2005).

Peet and Stokes, "Omega-3 fatty acids in the treatment of psychiatric disorders." Drugs. 2005;65(8):1051-9 (2005).

Rosamond W, et al., "Heart Disease and Stroke Statistics—2007 Update : A Report From the American Heart Association Statistics Committee and Stroke Statistics Subcommittee" Circulation, 115, e69-e171, (2007).

Salem Jr N, et al. Mechanisms of action of docosahexaenoic acid in the nervous system. Lipids 36: 945-959 (2001).

Stoll et al., "Omega 3 fatty acids in bipolar disorder: a preliminary double-blind, placebo-controlled trial." Arch Gen Psychiatry;56(5):407-12 (1999).

PCT/CA2010/001720 International Preliminary Report on Patentability.

PCT/CA2010/001720 International Search Report.

*P<0.05

Effects of Composition 3 on lipid biomarkers in male ZDF rats compared to age-matched controls Effects of Composition 3 on Glucose Intolerance in male ZDF rats Effects of Composition 3 on Glucose Intolerance in male SD rats

Effects of Composition 3 on Glucose Intolerance in male SD rats

CONCENTRATED THERAPEUTIC PHOSPHOLIPID COMPOSITIONS

CROSS-REFERENCE TO RELATED APPLICATIONS

This application claims the benefit of Provisional Application Ser. No. 61/256,106, filed Oct. 29, 2009, the contents of which are incorporated by reference in their entirety. All patents, patent applications, and publications cited herein are incorporated herein by reference in their entireties.

FIELD OF THE INVENTION

The invention relates to concentrated therapeutic compositions. More particularly, the invention relates to concentrated therapeutic phospholipid compositions useful for treating or preventing diseases.

BACKGROUND OF THE INVENTION

Genetic traits, coupled with a Western diet and lifestyle, have made cardiometabolic disorders/metabolic syndrome (MetS) a growing global epidemic. Cardiometabolic syndrome refers to a cluster of cardiovascular risk factors that include central obesity, high blood pressure, impaired glucose tolerance, hyperglycemia and dyslipidemia. Dyslipidemia is a major modifiable risk factor leading to atherosclerotic and related cardiovascular diseases (CVD), the nation's number one killer.

Cardiovascular Disease

Cardiovascular disease affects one in three people in the United States during their lifetime, and accounts for nearly a third of the deaths that occur each year (Rosamond W, et al., Circulation, 115, e69-e171, (2007)). Cardiovascular diseases are defined as diseases which affect the heart or blood vessels Statins are considered as first-line therapy for subjects at risk for CVD focusing predominantly on the reduction in low-density lipoprotein cholesterol (LDL-C or "bad cholesterol"), to recommended target levels. However statins have minimal effect in raising high-density lipoprotein cholesterol (HDL C or "good cholesterol"), now recognized as a major risk factor for developing cardiovascular disease. Treatment options to raise HDL-C are very limited and include Niaspan® (branded niacin) which is known to cause flushing and is reported to cause hepatic enzyme abnormalities, and Tricor® (branded fenofibrates) which causes a 40% increase in LDL C and significant increase in liver enzymes, hematological changes, gall stones, pancreatitis, as well as myopathy. Some treatment options lower plasma triglycerides but have a negligible effect on HDL-C (Lovaza®). Other treatment options increase HDL-C, but are less effective on triglycerides.

Others have tried to increase HDL C (good cholesterol) without deleteriously affecting LDL, TG, or causing hypertension, but have not been successful. For example, torcetrapib appeared to raise HDL levels, but had no effect on TGs and LDL. However, torcetrapib caused severe hypertension and high mortality in phase III trials. Despite advancements in lowering total cholesterol, lipid abnormalities as well as other severe negative side effects still prevail. Treatment gaps in the management of dyslipidemia, considered one of the top five major modifiable risk factors of CVD, represent critical unmet medical needs. While most treatment methods only target the intrinsic LDL-C synthesis in the liver, other treatments are needed to further reduce triglycerides while increasing HDL-C and not increasing LDL-C.

Neurodevelopmental and Neurodegenerative Disease

Neurodevelopmental and neurodegenerative diseases/disorders and neurological imbalance (in neurotransmitters) affect many people, and are defined as chronic progressive neuropathy characterized by selective and generally symmetrical loss of neurons in motor, sensory, or cognitive systems. One progressive neurodegenerative disorder, Alzheimer's disease (AD), is irreversible, and is characterized by gradual cognitive deterioration, changes in behavior and personality. These symptoms are related to neurochemical changes, neural death, and the breakdown of the inter-neural connections. Loss of short-term memory is often the first sign, followed by cognitive deficits involving multiple functions. Early stages of AD and mild cognitive impairment are characterized as milder forms of memory loss or cognitive impairment that could precede the onset of dementia and AD. Prevention of further cognitive decline in subjects with these possible precursor conditions is of paramount importance given that reversibility of AD is not possible.

It is estimated there are currently about 5.1 million people with Alzheimer's disease (AD) in the United States (Alzheimer's Association, 2007) and this number is expected to reach 13.2 million by 2050 (Hebert et al., 2003) Alzheimer's is ranked as the 7th leading cause of death in the US for people of all ages and the 5th for people aged 65 or older (National Center for Health Statistics, 2004). In Canada it is 280,000 people over 65 that are estimated to have AD, and over 750,000 are expected to have the disease by 2031 (Alzheimer Society of Canada, 2006). It is estimated to 10% of all North Americans over the age of 70 years have early stage AD or mild cognitive impairment.

Alzheimer's disease is characterized by two main pathological features of the brain: intracellular neurofibrillary tangles formed by abnormal protein τ (tau); and extracellular neuritic plaques formed by β-amyloid peptides (Aβ) (Kuo et al., 1996). The overproduction of Aβ42 is genetically induced but environmental risk factors are required to get fully symptomatic AD (Grant et al., 2002). Among these risk factors, low docosahexaenoic acid (DHA) is one of the most important dietary risk factor for AD (Morris et al., 2005). The reasons for the impact of DHA on learning and memory and the association with AD are unclear but could result from its loss in synapses (Montine et al., 2004), which are normally rich in DHA (Salem et al., 2001), where it is particularly important for postsynaptic transmission and neuroprotection (Bazan, 2003). Studies in animal models have consistently showed that brain n-3 fatty acid content is highly dependent on dietary intake and aging (Favrere et al., 2000; Youdim et al., 2000; Calon & Cole, 2007). However, some reports claim higher concentrations of DHA have a deleterious effect in neurological patients.

Omega-3 Fatty Acids and Inflammation

Several animal studies, has shown that increased DHA intake has been found to increase hippocampal acetycholine levels and its derivatives, neuroprotectin DI, which decreased cell death (Aid et al, 2005; Lukiw et al., 2005). A study conducted on aged mice showed that DHA intake improved memory performance (Lim et al. 2001). In another Alzheimer's disease mouse model, reduction in dietary DHA showed loss of postsynaptic proteins associated with increased oxidation, which was localized in the dendrites. However, when a group of DHA-restricted mice where given DHA, they showed signs that the DHA intake protected them against dendritic pathology, implying that DHA could be useful in preventing cognitive impairment in Alzheimer's Disease (Calon et al., 2004).

Several epidemiological studies have shown a protective effect associated with increased fish intake (a direct source of omega 3 fatty acids) against dementia and cognitive impairment decline (Kalmijin et al. 1997, Barberger-Gateau et al. 2002; Morris et al 2003). Recently, one large randomized double-blind placebo-controlled study found 1.6 g DHA and 0.7 EPA may be beneficial in reducing risk for AD (Freund-Levi et al, 2006). In addition, there is mounting evidence that dietary supplementation with Omega 3 fatty acids may be beneficial in different psychiatric conditions such as mood behaviour, depression and dementia (Bourre et al., 2005; Peet and Stokes, 2005; Stoll et al., 1999).

The anti-inflammatory effects of omega-3 fatty acids have been widely studied with positive results for several chronic inflammatory diseases. C-reactive protein (CRP) is a protein that increases dramatically during inflammatory processes and is commonly measured as a marker of inflammation. Greater intake of omega-3 polyunsaturated fatty acid is related to a lower prevalence of elevated CRP levels. Animal models of colitis indicate that fish oil, a natural source of omega 3 fatty acids, decreases colonic damage and inflammation. Fish oil supplements in subjects with IBD have shown to modulate levels of inflammatory mediators and may be beneficial for the induction and maintenance of remission in ulcerative colitis. In the management of RA and other inflammatory conditions, side effects limit the use of NSAIDs, such as salicylates, ibuprofen and naproxen. A clinical trial showed that 39 percent of subjects with RA supplemented with cod liver oil were able to reduce their daily NSAID requirement by greater than 30 percent. Omega-3 fatty acids have been used to reduce the risk for sudden death caused by cardiac arrhythmias.

Furthermore, omega-3 fatty acids have been shown to improve insulin sensitivity and glucose tolerance in normoglycemic men and in obese individuals. Omega-3 fatty acids have also been shown to improve insulin resistance in obese and non-obese subjects with an inflammatory phenotype. Lipid, glucose and insulin metabolism have been show to be improved in overweight hypertensive subjects through treatment with omega-3 fatty acids.

Omega-3 fatty acids can be obtained from marine organisms such as squid, fish, krill, etc. and are sold as dietary supplements. However, the uptake of omega-3 fatty acids by the body is not efficient and these raw oils contain other substances such a triglycerides and cholesterol which are known to cause deleterious side effects such as an increase in LDL-C. Certain fish oils have been developed as pharmaceutical-grade OM3-acid ethyl esters. One such OM3-acid ethyl ester is presently sold under the brand name Lovaza®. Studies have shown that Lovaza® can decrease plasma triglycerides levels in patients, however, Lovaza® has a negligible effect on raising good cholesterol (HDL-C). AMR101 is another ethyl ester form of OM3 fatty acids based on EPA with little or no DHA that is presently in clinical trials. AMR101 also appears to decrease triclycerides but also has a negligible effect on raising HDL-C.

A phospholipid composition of OM3 fatty acids has been disclosed in US 2004/0234587. This phospholipid composition has OM3 fatty acids esterified to the phospholipid. This phospholipid composition is reported to be at a concentration of about 40% phospholipids (w/w composition) and contains high concentrations of triglycerides (about 45%) and free fatty acids (about 15%). When tested in subjects, this composition demonstrated very little effect on lowering triglyceride plasma levels (less than 11% reduction).

Marine oil compositions comprising free fatty acids and lipids, including OM3 fatty acids and phospholipids, have been disclosed in WO 2000/23546, however the compositions do not disclose OM3 fatty acids esterified to diglycerol phosphate and have very high concentrations of triglycerides and free fatty acids, and for these reasons would not be expected to reduce triglycerides even to the level of the composition disclosed in US 2004/0234587, described above.

Therefore, new forms of omega-3 fatty acids are needed that are useful for treating or preventing disease. Described herein are novel concentrated therapeutic phospholipid compositions, as well as pharmaceutical compositions comprising same, and methods of their use.

SUMMARY OF THE INVENTION

Accordingly, in one aspect concentrated therapeutic phospholipid compositions are described, the compositions comprising compounds of the Formula I:

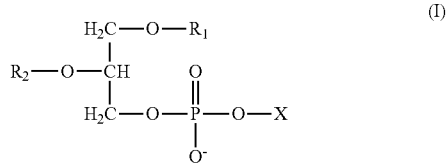

wherein for each compound of Formula I in the compositions
each $R_1$ is independently selected from hydrogen or any fatty acid;
each $R_2$ is independently selected from hydrogen or any fatty acid;
wherein at least one of $R_1$ and $R_2$ in each compound of Formula I is a fatty acid; and
each X is independently selected from —$CH_2CH_2NH_3$, —$CH_2CH_2N(CH_3)_3$ or

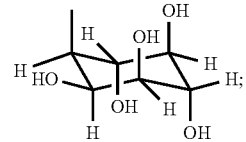

wherein the total amount of the compounds of Formula I in the composition being at a concentration of between 45% (w/w) to about 99% (w/w).

In some embodiments, the compounds of Formula I in the concentrated therapeutic phospholipid composition are in a concentration of between about 45% (w/w (phospholipids/total composition)) up to 70% (w/w (phospholipids/total composition)). In still further embodiments, the compounds of Formula I in the concentrated therapeutic phospholipid composition are in a concentration of between about 50% (w/w (phospholipids/total composition)) up to 70% (w/w (phospholipids/total composition)). In other embodiments, the compounds of Formula I in the concentrated therapeutic phospholipid composition are in a concentration of between about 60% (w/w (phospholipid/total composition)) up to 70% (w/w (phospholipids/total composition)). In still other embodiments, the compounds of Formula I in the concentrated therapeutic phospholipid composition are in a concentration of about 66% (w/w (phospholipids/total composition)).

In other embodiments, the compounds of Formula I in the concentrated therapeutic phospholipid composition are in a concentration of above 70% (w/w (phospholipids/total composition)) to about 99% (w/w (phospholipids/total composition)). In still other embodiments, the compounds of Formula I in the concentrated therapeutic phospholipid composition are in a concentration of between about 80% (w/w (phospholipids/total composition)) to about 98% (w/w (phospholipids/total composition)). In still other embodiments, the compounds of Formula I in the concentrated therapeutic phospholipid composition are in a concentration of between about 85% (w/w (phospholipids/total composition)) to about 95% (w/w (phospholipids/total composition)). In further embodiments, the compounds of Formula I in the concentrated therapeutic phospholipid composition are in a concentration of about 90% (w/w (phospholipids/total composition)).

In some embodiments, R1 is a monounsaturated fatty acid. In other embodiments, R1 is a polyunsaturated fatty acid. In some embodiments, R2 is a monounsaturated fatty acid. In other embodiments, R2 is a polyunsaturated fatty acid. In other embodiments, the polyunsaturated fatty acid is an omega 3 fatty acid. In still other embodiments, both R1 and R2 are each independently selected from an omega 3 fatty acid. When at least one of R1 and R2 is an omega 3 fatty acid, the concentrated therapeutic phospholipid composition comprising compounds of Formula I is known as an OM3:PL.

In other embodiments, R1 is docosahexaenoic acid (DHA). In other embodiments, R2 is a monounsaturated fatty acid and R1 is DHA. In other embodiments, R2 is a polyunsaturated fatty acid and R1 is DHA. In other embodiments, R2 is an omega 3 fatty acid and R1 is DHA. In still further embodiments, R2 is EPA and R1 is DHA. In still further embodiments, R2 is DHA and R1 is DHA.

In other embodiments, R1 is eicosapentaenoic acid (EPA). In other embodiments, R2 is a monounsaturated fatty acid and R1 is EPA. In other embodiments, R2 is a polyunsaturated fatty acid and R1 is EPA. In other embodiments, R2 is an omega 3 fatty acid and R1 is EPA. In still further embodiments, R2 is DHA and R1 is EPA. In still further embodiments, R2 is EPA and R1 is EPA.

In another embodiment, R2 is DHA. In other embodiments, R1 is a monounsaturated fatty acid and R2 is DHA. In other embodiments, R1 is a polyunsaturated fatty acid and R2 is DHA. In other embodiments, R1 is an omega 3 fatty acid and R2 is DHA.

In other embodiments, R2 is EPA. In other embodiments, R1 is a monounsaturated fatty acid and R2 is EPA. In other embodiments, R1 is a polyunsaturated fatty acid and R2 is EPA. In other embodiments, R1 is an omega 3 fatty acid and R2 is EPA.

In some embodiments, the compounds of Formula I in the concentrated therapeutic phospholipid composition have predominantly DHA at the R2 position of Formula I. In other embodiments, there is more DHA in the compounds of Formula I in the concentrated therapeutic phospholipid composition than EPA. In some embodiments, the compounds of Formula I in the concentrated therapeutic phospholipid composition have greater than 60% DHA. In other embodiments, the compounds of Formula I in the concentrated therapeutic phospholipid composition have greater than 70% DHA. In other embodiments, the compounds of Formula I in the concentrated therapeutic phospholipid composition have greater than 80% DHA. In other embodiments, the compounds of Formula I in the concentrated therapeutic phospholipid composition have greater than 90% DHA. In other embodiments, the compounds of Formula I in the concentrated therapeutic phospholipid composition have greater than 95% DHA.

In some embodiments, there are free fatty acids in the concentrated therapeutic phospholipid composition, in addition to the fatty acids esterified to the phosphate. In other embodiments, there are essentially no free fatty acids (also expressed as 0% free fatty acids (or FFA)) in the concentrated therapeutic phospholipid composition.

In other embodiments, the ratio of the total amount of DHA to EPA in the concentrated therapeutic phospholipid composition is between about 1:1 and 1:0.1. In some embodiments, the ratio is between about 1:0.7 and about 1:0.3. In other embodiments, the ratio is about 1:0.5.

In some embodiments, the ratio of the total amount of EPA to DHA in the compounds of Formula I in the concentrated therapeutic phospholipid composition is between about 1:1 and 1:0.1. In some embodiments, the ratio is between about 1:0.7 and about 1:0.3. In other embodiments, the ratio is about 1:0.5.

In some embodiments, the total amount of OM3 fatty acids in the concentrated therapeutic phospholipid composition is between about 20% and about 50%. In other embodiments, the total amount of OM3 fatty acids in the concentrated therapeutic phospholipid composition is between about 30% and about 45%. In other embodiments, the total amount of OM3 fatty acids in the concentrated therapeutic phospholipid composition is about 40%.

In some embodiments, the total amount of DHA in the concentrated therapeutic phospholipid composition is between about 5% and 20%. In some embodiments, the total amount of DHA in the concentrated therapeutic phospholipid composition is between about 10% and 15%. In some embodiments, the total amount of DHA in the concentrated therapeutic phospholipid composition is about 14%.

In some embodiments, the total amount of EPA in the concentrated therapeutic phospholipid composition is between about 10% and 30%. In some embodiments, the total amount of DHA in the concentrated therapeutic phospholipid composition is between about 15% and 25%. In some embodiments, the total amount of EPA in the concentrated therapeutic phospholipid composition is about 22%.

In some embodiments, X is —CH$_2$CH$_2$NH$_3$. In other embodiments, X is —CH$_2$CH$_2$N(CH$_3$)$_3$. In some embodiments, X is

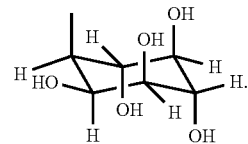

In some embodiments, the concentrated therapeutic phospholipid composition comprises predominantly phospholipids containing —CH$_2$CH$_2$N(CH$_3$)$_3$ (also known as a phosphoyidyl-N-trimethylethanolamine).

In other embodiments, the concentrated therapeutic phospholipid composition further comprises an antioxidant. In some embodiments, the antioxidant is a carotenoid. In other embodiments, the carotenoid is pro-vitamin A. In other embodiments, the antioxidant is a flavonoid. In other embodiments, the flavonoid is selected from naringin, naringenin, hesperetin/kaempferol, rutin, luteolin, neohesperidin, quecertin. In other embodiments, the flavonoid is

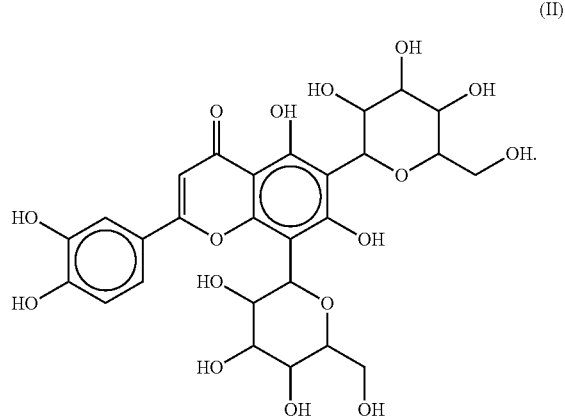
(II)

In some embodiments, the concentration of the flavonoid is between about 1 mg/kg (w/w of composition) and about 20 mg/kg (w/w of composition). In other embodiments, the concentration of the flavonoid is greater than about 10 mg/kg (w/w of composition).

In further embodiments, the concentrated therapeutic phospholipid composition has a concentration of astaxanthin greater than 2000 mg/kg (w/w of composition). In still other embodiments, the concentration of astaxanthin is between about 2,000 mg/kg (w/w of composition) and about 5,500 mg/kg (w/w of composition).

In some embodiments, the concentrated therapeutic phospholipid composition has a free fatty acid concentration below about 22% (w/w of composition). In some embodiments, the concentrated therapeutic phospholipid composition has a free fatty acid concentration below about 15% (w/w of composition). In some embodiments, the concentrated therapeutic phospholipid composition has a free fatty acid concentration below about 10% (w/w of composition). In some embodiments, the concentrated therapeutic phospholipid composition has a free fatty acid concentration below about 5% (w/w of composition). In some embodiments, the concentrated therapeutic phospholipid composition has a free fatty acid concentration of about 1% (w/w of composition). In some embodiments, the concentrated therapeutic phospholipid composition has a free fatty acid concentration below 1% (w/w of composition). In some embodiments, the concentrated therapeutic phospholipid composition has a free fatty acid concentration of 0% (w/w of composition).

In some embodiments, the concentrated therapeutic phospholipid composition has a free fatty acid concentration of between about 1% (w/w) and about 20% (w/w). In some embodiments, the concentrated therapeutic phospholipid composition has a free fatty acid concentration of between about 5% (w/w) and about 17% (w/w). In some embodiments, the concentrated therapeutic phospholipid composition has a free fatty acid concentration of between about 10% (w/w) and about 15% (w/w).

In some embodiments, the concentrated therapeutic phospholipid composition has a triglyceride concentration between about 0% (w/w) and about 30% (w/w). In other embodiments, the concentrated therapeutic phospholipid composition has a triglyceride concentration between about 5% and about 20%. In still further embodiments, the concentrated therapeutic phospholipid composition has a triglyceride concentration between about 10% and about 15%.

In some embodiments, the concentrated therapeutic phospholipid composition has a triglyceride concentration below about 15%. In some embodiments, the concentrated therapeutic phospholipid composition has a triglyceride concentration below about 10%. In some embodiments, the concentrated therapeutic phospholipid composition has a triglyceride concentration below about 5%. In some embodiments, the concentrated therapeutic phospholipid composition has a triglyceride concentration about 1%. In some embodiments, the concentrated therapeutic phospholipid composition has a triglyceride concentration below 1%. In some embodiments, the concentrated therapeutic phospholipid composition has a triglyceride concentration of about 0%.

In other embodiments, the concentrated therapeutic phospholipid composition comprises at least 50% compounds of Formula I (w/w), wherein at least 15% of the fatty acid content is EPA, at least 9% of the fatty acid content is DHA, and at least 0.1% astaxanthin (w/w). In other embodiments, the concentrated therapeutic phospholipid composition comprises at least 66% compounds of Formula I (w/w), wherein at least 20% of the fatty acid content is EPA, at least 12% of the fatty acid content is DHA, and at least 0.4% astaxanthin (w/w). In other embodiments, the concentrated therapeutic phospholipid composition comprises at least 90% compounds of Formula I (w/w), at least 22% of the fatty acid content is EPA, at least 12% of the fatty acid content is DHA, and 0.4% astaxanthin (w/w).

In other embodiments, the concentrated therapeutic phospholipid composition comprises at least 50% compounds of Formula I (w/w composition), wherein at least 15% of the fatty acid content is EPA, at least 9% of the fatty acid content is DHA. In other embodiments, the concentrated therapeutic phospholipid composition comprises at least 66% compounds of Formula I (w/w), wherein at least 20% of the fatty acid content is EPA, at least 12% of the fatty acid content is DHA. In other embodiments, the concentrated therapeutic phospholipid composition comprises above 70% compounds of Formula I (w/w), wherein at least 22% of the fatty acid content is EPA, at least 12% of the fatty acid content is DHA. In other embodiments, the concentrated therapeutic phospholipid composition comprises above 90% compounds of Formula I (w/w), wherein at least 22% of the fatty acid content is EPA, at least 12% of the fatty acid content is DHA.

In one aspect, a concentrated therapeutic phospholipid composition is described comprising compounds of Formula at a concentration of about 66% (w/w (phospholipids/total composition) a free fatty acid (FFA) concentration of less than 6% (w/w FFA/total composition) and a triglyceride concentration of about 0%, the composition being useful for treating and preventing cardiometabolic disorders/metabolic syndrome. In some embodiments, 1 g of the concentrated therapeutic phospholipid composition comprises about 387 mg of total OM3 fatty acids wherein EPA is at about 215 mg and DHA is at about 136 mg) and astaxanthine at about 5 mg.

In one aspect, a concentrated therapeutic phospholipid composition is described comprising compounds of Formula at a concentration of above 70% (w/w (phospholipids/total composition), a free fatty acid (FFA) concentration of about 0% and a triglyceride concentration of about 0%, the composition being useful for treating and preventing neurodegenerative and neurodevelopmental disorders and diseases.

In one aspect, the invention is based in part on the unexpected and surprising discovery that concentrated therapeutic phospholipid compositions are useful in modulating plasma triglyceride levels as well as plasma HDL C levels, while not elevating LDL C levels. This unexpected and surprising discovery is useful in the treatment or prevention of disorders associated with increased triglyceride levels, increased LDL-C levels and decreased HDL-C levels. Such diseases and disorders include but are not limited to cardiometabolic disorders/metabolic syndrome (MetS), neurodevelopmental and neurodegenerative diseases/disorders, and inflammation disorders.

In another aspect, a method of treating or preventing a cardiometabolic disorder/metabolic syndrome is described, the method comprising administering to a subject in need thereof a concentrated therapeutic phospholipid composition. In some embodiments, the cardiometabolic disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy. In some instances, the methods described above for treating or preventing a cardiometabolic disorder/metabolic syndrome may utilize concentrated therapeutic phospholipid compositions having a concentration of 66% (w/w (phospholipids/composition)).

In another aspect, methods of treating, preventing, or improving cognition and/or a cognitive disease, disorder or impairment (memory, concentration, learning (deficit)), or of treating or preventing neurodegenerative disorders are described, the method comprising administering to a subject in need thereof a concentrated therapeutic phospholipid composition. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodevelopmental, neurodegenerative disorders, hormonal disorders, neurological imbalance or any combinations thereof. In a specific embodiment, the cognitive disorder is memory impairment. In some instances, the methods described above for treating, preventing, or improving cognition and/or a cognitive disease, disorder or impairment (memory, concentration, learning (deficit)), or of treating or preventing neurodegenerative disorders may utilize concentrated therapeutic phospholipid compositions having a concentration of greater than 70% (w/w (phospholipids/composition)).

In another aspect, a method for inhibiting, preventing, or treating inflammation or an inflammatory disease is described, the method comprising administering to a subject in need thereof, a concentrated therapeutic phospholipid composition. In some embodiments, the inflammation or inflammatory disease is selected from organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated with the concentrated therapeutic phospholipid compositions.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

All patents and publications cited in this specification are incorporated herein by reference in their entireties.

DETAILED DESCRIPTION OF THE INVENTION

Figure 1A:
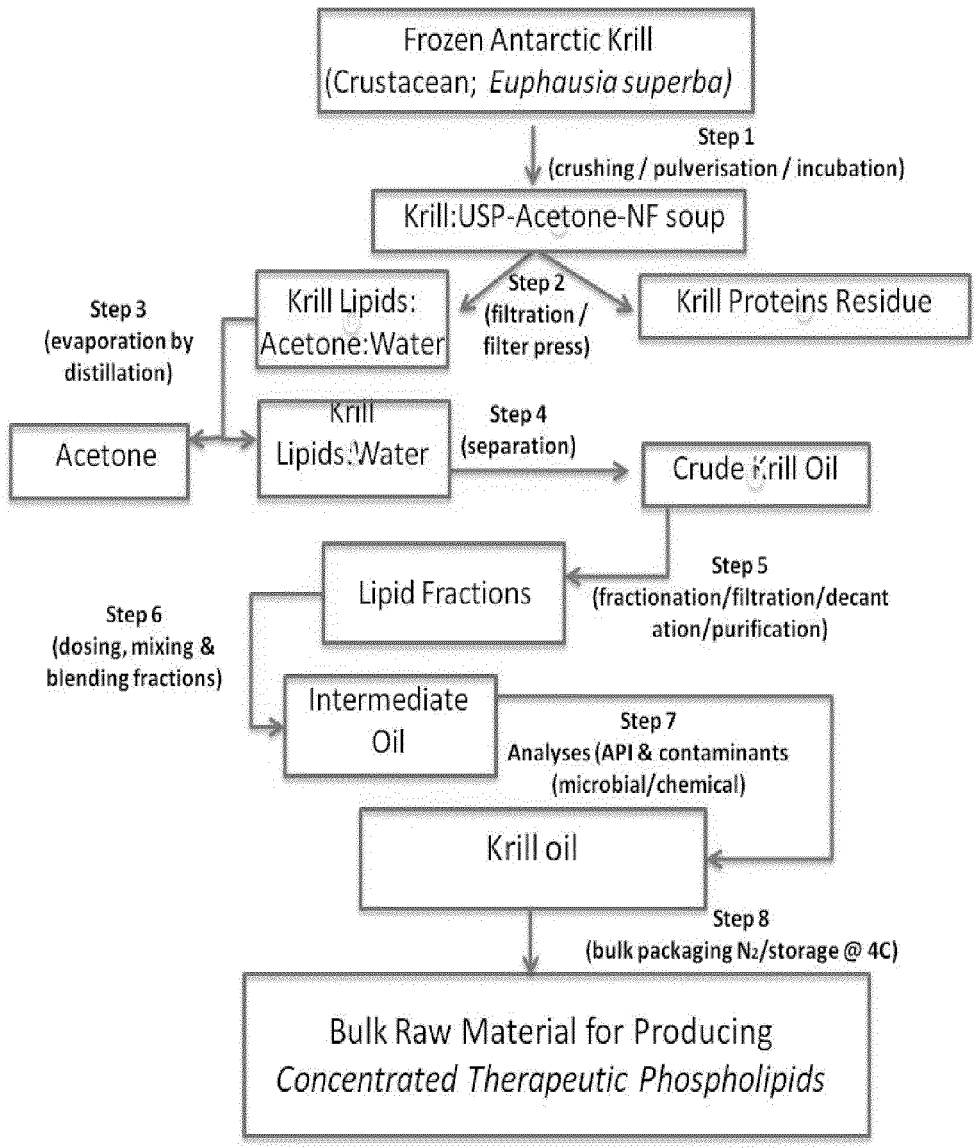
FIG. 1A depicts a flow chart for the process for making the concentrated therapeutic phospholipid compositions.

It has been unexpectedly discovered that concentrated therapeutic phospholipid compositions demonstrate surprising effects in the treatment of metabolic disorders, cardiovascular disease, neurodevelopmental disorders and neurodegenerative diseases, and inflammation disorders.

DEFINITIONS

The following definitions are used in connection with the concentrated therapeutic phospholipid compositions:

The term "concentrated therapeutic phospholipid composition" and "concentrated therapeutic phospholipid compositions" as used herein refer to the concentrated therapeutic phospholipid compositions comprising compounds of Formula I.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "about" when used in this disclosure along with a recited value means the value recited and includes the range of + or −5% of the value. For example, the phrase about 80% means 80% and + or −5% of 80, i.e. 76% to 84%. The recited value "about 0%" as used herein means that the detectable amount is less than one part per thousand.

The term "fatty acid" or "fatty acid residue" as used herein means a carboxylic acid with a long unbranched aliphatic chain, which is either saturated or unsaturated. Saturated fatty acids have the general formula $C_nH_{2n}+1$ COOH. Examples of saturated fatty acids include but are not limited to: Propanoic acid, Butanoic acid, Pentanoic acid, Hexanoic acid, Heptanoic acid, Octanoic acid, Nonanoic acid, Decanoic acid, Undecanoic acid, Dodecanoic acid, Tridecanoic acid, Tetradecanoic acid, Pentadecanoic acid, Hexadecanoic acid, Heptadecanoic acid, Octadecanoic acid, Nonadecanoic acid, Eicosanoic acid, Heneicosanoic acid, Docosanoic acid, Tricosanoic acid, Tetracosanoic acid, Pentacosanoic acid, Hexacosanoic acid, Heptacosanoic acid, Octacosanoic acid, Nonacosanoic acid, Triacontanoic acid, Henatriacontanoic acid, Dotriacontanoic acid, Tritriacontanoic acid, Tetratriacontanoic acid, Pentatriacontanoic acid, Hexatriacontanoic acid. An unsaturated fat is a fat or fatty acid in which there are one or more double bonds in the fatty acid chain. A fat molecule is monounsaturated if it contains one double bond, and polyunsaturated if it contains more than one double bond. Examples of unsaturated fatty acids include but are not limited to: Myristoleic acid, Palmitoleic acid, Sapienic acid, Oleic acid, Linoleic acid, α-Linolenic acid, Arachidonic acid, Eicosapentaenoic acid (EPA), Erucic acid, Docosahexaenoic acid (DHA), and Docosapentaenoic acid.

A "subject" is a mammal, e.g., a human, mouse, rat, guinea pig, dog, cat, horse, cow, pig, or non-human primate, such as a monkey, chimpanzee, baboon or rhesus.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "metabolic disorder" as used herein refers to disorders, diseases and syndromes involving dyslipidemia, and the terms metabolic disorder, metabolic disease, and metabolic syndrome are used interchangeably herein.

An "effective amount" when used to describe an amount of a concentrated therapeutic phospholipid composition useful for treating or preventing a disease or disorder, is an amount that is efficacious with respect to the disease or disorder connected with that particular effective amount.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

Methods of Making the Concentrated Therapeutic Phospholipid Compositions

The concentrated therapeutic phospholipid compositions can be made or produced by any method known to one of skill in the art. For example, phospholipid containing oils can be isolated from natural sources (see US 2004/0234587, US 2009/0074857, and US 2008/0274203, the disclosures of which are incorporated by reference in their entireties), which can then be further processed. Alternatively, following the process outlined in FIG. 1a results in bulk raw material krill oil ready for further processing. These phospholipid containing oils can be further processed using countercurrent supercritical $CO_2$ extraction (Lucien, F. P., et al., Australas Biotechnol. 1993, 3, 143-147) to concentrate the compositions to produce the concentrated therapeutic phospholipid compositions described herein (see FIG. 1b). For example, countercurrent supercritical $CO_2$ extraction at 70 C and 30 MPa and with a $CO_2$/oil ratio of 72 can be used to remove certain biomolecules such as all triglycerides from the bulk raw material krill oil as well as some of the free fatty acids (FIG. 1b). As more of the TGs and FFAs are removed from the bulk raw material krill oil, the concentration of the phospholipids increases. When the TGs have been removed through this process the phospholipid composition is at about 66% concentration (w/w (phospholipids/composition)) and contains less than 5% free fatty acids (w/w). As more of the FFAs are removed using this process, a concentrated therapeutic phospholipid composition results having a phospholipid concentration above 70% up to about 90% (w/w (phospholipids/composition)) having about 1% or less TG and about 0% FFA. Other aquatic and/or marine biomasses may be used as starting materials, such as, for example, squid or blue mussels. Additional components can be added before, during, or after processing. Alternatively, phospholipids can be synthesized; a typical way to synthesize would be, among others, according to the procedure described in U.S. Pat. No. 7,034,168, the disclosure of which is incorporated herein its entirety.

Methods for Using the Concentrated Therapeutic Phospholipid Compositions

Described herein are methods of reducing circulating plasma concentrations of triglycerides, LDL-cholesterol, total cholesterol and NEFA, the method comprising administering to a subject in need thereof an effective amount of a Composition of the Invention.

Also provided are methods of increasing plasma concentrations of HDL-cholesterol and hepatic concentrations of triglycerides and total cholesterol, the method comprising administering to a subject in need thereof an effective amount of a concentrated therapeutic phospholipid composition.

In another aspect, a method of reducing TG without the risk of increasing LDL is described, the method comprising administering to a subject in need thereof, a concentrated therapeutic phospholipid composition.

Also provided are methods for inhibiting, preventing, or treating a metabolic disorder, or symptoms of a metabolic disease, in a subject, the method comprising administering to a subject in need thereof an effective amount of a concentrated therapeutic phospholipid composition. Examples of such disorders include, but are not limited to atherosclerosis, dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, carotid atherosclerosis, peripheral arterial disease, diabetic nephropathy, hypercholesterolemia in HIV infection, acute coronary syndrome (ACS), non-alcoholic fatty liver disease, arterial occlusive diseases, cerebral atherosclerosis, arteriosclerosis, cerebrovascular disorders, myocardial ischemia, and diabetic autonomic neuropathy.

Also provided are methods for inhibiting, preventing, or treating inflammation or an inflammatory disease in a subject. The inflammation can be associated with an inflammatory disease. Inflammatory diseases can arise where there is an inflammation of the body tissue. These include local inflammatory responses and systemic inflammation. Examples of such diseases include, but are not limited to: organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis. Metabolic disease such as type II diabetes mellitus; the prevention of type I diabetes; dyslipedemia; diabetic complications, including, but not limited to glaucoma, retinopathy, nephropathy, such as microaluminuria and progressive diabetic nephropathy, polyneuropathy, atherosclerotic coronary arterial disease, peripheral arterial disease, nonketotic hyperglycemichyperosmolar coma, mononeuropathies, autonomic neuropathy, joint problems, and a skin or mucous membrane complication, such as an infection, a shin spot, a candidal infection or necrobiosis lipoidica diabeticorum; immune-complex vasculitis, systemic lupus erythematosus; inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated with the concentrated therapeutic phospholipid compositions.

Also provided are methods for inhibiting, preventing, or treating hypertriglyceridemia in subject. In some embodiments, the hypertriglyceridemia is moderate hypertriglyceridemia. In some embodiments, the subject is diagnosed with moderate hypertriglyceridemia. Moderate hypertriglyceridemia is defined as a subject having a TG level of >3.9 mmol/L (>350 mg/dL).

Also provided are methods for reducing fasting plasma levels of Low-density Lipoprotein Cholesterol (LDL-C) in a subject. In some embodiments of reducing fasting plasma levels of Low-density Lipoprotein Cholesterol (LDL-C), the subject is diagnosed with moderate hypertriglyceridemia.

Also provided are methods for increasing fasting plasma levels of High-density Lipoprotein Cholesterol (HDL-C) in a subject. In some embodiments of increasing fasting plasma levels of High-density Lipoprotein Cholesterol (HDL-C), the subject is diagnosed with moderate hypertriglyceridemia.

Also provided are methods for increasing the Omega-3 index (OM3I) in a subject. The Omega-3 Index is defined as the percentage of EPA+DHA in red blood cells (RBC) which can be represented by the formula: OM3I=(EPA+DHA)/Total fatty acids in RBC. Low levels of EPA+DHA in erythrocytes are associated with increased risk for sudden cardiac death and can be viewed as a marker of increased risk (an actual risk factor) for death from coronary heart disease (Harris, 2010). In other embodiments, the method provided elevates the omega-3 index (OM3I) and reduces oral glucose intolerance (OGTT). In some embodiments of increasing omega-3 index, the subject is diagnosed with moderate hypertriglyceridemia.

Also provided are methods for reducing high sensitivity C-reactive protein (hs-CRP) in a subject. In some embodiments of reducing high sensitivity C-reactive protein (hs-CRP), the subject is diagnosed with moderate hypertriglyceridemia.

Also provided are methods for inhibiting, preventing, or treating cardiovascular disease in a subject. Cardiovascular diseases include atherosclerosis, arteriosclerosis, coronary artery disease, heart valve disease, arrhythmia, heart failure, hypertension, orthostatic hypotension, shock, endocarditis, diseases of the aorta and its branches, disorders of the peripheral vascular system, and congenital heart disease.

Also provided are methods for inhibiting, preventing, or treating metabolic syndrome in a subject. Metabolic syndrome is a combination of medical disorders that increase the risk of developing cardiovascular disease and diabetes. It affects one in five people, and prevalence increases with age. Some studies estimate the prevalence in the USA to be up to 25% of the population. Metabolic syndrome is also known as metabolic syndrome X, syndrome X, insulin resistance syndrome, Reaven's syndrome, and CHAOS (Australia).

Also provided are methods for inhibiting, preventing, or treating a cognitive disorder, in a subject. The term "cognitive disease or disorder" as used herein should be understood to encompass any cognitive disease or disorder. Non-limiting examples of such a cognitive disease or disorder are Attention Deficit Disorder (ADD), Attention Deficit Hyperactivity Disorder (ADHD), dyslexia, age-associated memory impairment and learning disorders, amnesia, mild cognitive impairment, cognitively impaired non-demented, pre-Alzheimer's disease, autism, dystonias and Tourette syndrome, dementia, age related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodegenerative disorders, hormonal disorders or any combinations thereof. In a specific embodiment, the cognitive disorder is memory impairment.

The term "improving a condition in a subject suffering from a cognitive disease or a cognitive disorder" as used herein should be understood to encompass: ameliorating undesired symptoms associated with a disease, disorder, or pathological condition; preventing manifestation of symptoms before they occur; slowing down progression of a disease or disorder; slowing down deterioration of a disease or disorder; slowing down irreversible damage caused in a progressive (or chronic) stage of a disease or disorder; delaying onset of a (progressive) disease or disorder; reducing severity of a disease or disorder; curing a disease or disorder; preventing a disease or disorder from occurring altogether (for example in an individual generally prone to the disease) or a combination of any of the above. For example, in a subject suffering from memory impairment, for example as a result of Alzheimer's Disease, symptoms including deterioration of spatial short-term memory, memory recall and/or memory recognition are improved by use of a lipid concentrated therapeutic phospholipid composition.

Also provided are methods for inhibiting, preventing, or treating neurodegenerative disorder in a subject. Neurodegenerative disorder is defined as a chronic progressive neuropathy characterized by selective and generally symmetrical loss of neurons in motor, sensory, or cognitive systems. Non limiting examples of neurodegenerative disorders include but are not limited to Alzheimer's disease, Picks disease, Lewy body dementia Basal ganglia—Huntington's disease, Parkinson's disease, dentatorubropallidoluysian atrophy, Freidreich's ataxia, multiple system atrophy, types 1, 2, 3, 6, 7 spinocerebellar ataxia Motor—amyotrophic lateral sclerosis, familial spastic paraparesis, spinal muscular atrophy, spinal and bulbar muscular atrophy, Lou Gehrig's disease, pre-dementia syndrome, Lewy body dementia, age-related cognitive decline, cognitive deterioration, moderate mental impairment, mental deterioration as a result of ageing, dentatorubropallidoluysian atrophy, Freidreich's ataxia, multiple system atrophy, types 1, 2, 3, 6, 7 spinocerebellar ataxia, amyotrophic lateral sclerosis, and familial spastic paraparesis.

Also provided are methods for reducing the decline of global cognitive function in a subject. In some embodiments, the reduction in decline of global cognitive function can be measured by the Neuropsychological Test Battery (NTB). In some embodiments, the subject is diagnosed with early stage Alzheimer's disease.

Also provided are methods for reducing worsening of neuropsychiatric symptoms in a subject. In some embodiments, the reduction is measured by the Neuropsychiatric Inventory questionnaire (NPI). In some embodiments, the subject is diagnosed with early stage Alzheimer's disease.

Also provided are methods for maintaining self-care and activities of daily living function in a subject suffering from Alzheimer's disease. In some embodiments, the subject is diagnosed with early stage Alzheimer's disease. In some embodiments, the maintaining self-care and activities of daily living function is measured by the Disability Assessment in Dementia caregiver-based interview (DAD).

Additional health disorders or conditions which may be treated or improved by the concentrated therapeutic phospholipid compositions include, but are not limited to, high blood cholesterol levels, high triglycerides levels, high blood fibrinogen levels, low HDL/LDL ratio, menopausal or post-menopausal conditions, hormone related disorders, vision disorders, immune disorders, liver diseases, chronic hepatitis, steatosis, lipid peroxidation, dysrhythmia of cell regeneration, destabilization of cell membranes, high blood pressure, cancer, hypertension, aging, kidney disease, skin diseases, edema, gastrointestinal diseases, peripheral vascular system diseases, allergies, airways diseases, and psychiatric diseases.

Combination Therapies

In some embodiments, the subject is administered an effective amount of a concentrated therapeutic phospholipid composition. In other embodiments, the treatment comprises a combination of a concentrated therapeutic phospholipid composition and treatment agents such as anti-dyslipidemic agents. Anti-dyslipidemic agents include but are not limited to atorvastatin, fluvastatin, lovastatin, pitavastatin, pravastatin, rosuvastatin and simvastatin.

In other embodiments, the treatment comprises a combination of a concentrated therapeutic phospholipid composition and a cholinesterase inhibitor. Cholinesterase inhibitors include but are not limited to metrifonate (irreversible), carbamates, physostigmine, neostigmine, pyridostigmine, ambenonium, demarcarium, rivastigmine, phenanthrene derivatives, galantamine, piperidines, donepezil, tacrine, edrophonium, huperzine A, ladostigill and ungeremine.

In some embodiments, the subject is administered a combination of a concentrated therapeutic phospholipid composition and at least one of vitamins, minerals, cox-inhibitors, sterols, fibrates, antihypertensives, insulin, cholesterol digestion inhibitors, for example, ezetimibe, fatty acids, omega-3 fatty acids, antioxidants, and the methylphenydate class of compounds, such as for example ritalin. In other embodiments, a combination of a concentrated therapeutic phospholipid composition and elements depleted during traditional chronic treatments, such as for example during chronic treatment with statins. For example, in some embodiments, a concentrated therapeutic phospholipid composition is described which contains at least one of cox-2, folic acid, vitamin B6, vitamin B12, magnesium or zinc. In other embodiments, combination therapies comprising a concentrated therapeutic phospholipid composition and potassium are described. Potassium is usually depleted during treatment with diuretics. Combination therapies reduce risk of side effects, increase benefits, increase solubility, and/or increase bioavailability.

Modes of Administration

Administration of the concentrated therapeutic phospholipid compositions can be accomplished via any mode of administration for therapeutic agents. These modes include systemic or local administration such as oral, parenteral, transdermal, subcutaneous, or topical administration modes.

Pharmaceutical Formulations

Depending on the intended mode of administration, the compositions can be in solid, semi-solid or liquid dosage form, such as, for example, injectables, tablets, pills, time-release capsules, elixirs, tinctures, emulsions, syrups, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a concentrated therapeutic phospholipid composition neat, or if required, contains a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the concentrated therapeutic phospholipid composition is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the concentrated therapeutic phospholipid composition.

Other illustrative topical preparations include creams, ointments, lotions, aerosol sprays and gels, wherein the concentration of the concentrated therapeutic phospholipid composition ranges from about 0.1% to about 15%, w/w or w/v.

Dosing

The dosage regimen utilizing the concentrated therapeutic phospholipid compositions is selected in accordance with a variety of factors including type, species, age, weight, sex and medical condition of the subject; the severity of the condition to be treated; the route of administration; the renal or hepatic function of the subject; and the particular concentrated therapeutic phospholipid composition employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 10000 mg of the concentrated therapeutic phospholipid composition per day. Dosages for in vivo or in vitro use can contain about 20, 50, 75, 100, 150, 250, 500, 750, 1000, 1250, 2500, 3500, 5000, 7500 or 10000 mg of the concentrated therapeutic phospholipid composition. Effective blood plasma levels after administration of the concentrated therapeutic phospholipid composition to a subject can range from about 0.002 mg to about 100 mg per kg of body weight per day. Appropriate dosages of the concentrated therapeutic phospholipid composition can be determined as set forth in L. S. Goodman, et al., *The Pharmacological Basis of Therapeutics*, 201-26 (5th ed. 1975).

The concentrated therapeutic phospholipid compositions can be administered in a single daily dose, or the total daily dosage can be administered in divided doses of two, three or four times daily. To be administered in the form of a transdermal delivery system, the dosage administration can be continuous rather than intermittent throughout the dosage regimen. In some embodiments, of combination therapy, the concentrated therapeutic phospholipid composition and the therapeutic agent can be administered simultaneously. In other embodiments, the concentrated therapeutic phospholipid composition and the therapeutic agent can be administered sequentially. In still other embodiments of combination therapy, the concentrated therapeutic phospholipid composition can be administered daily and the therapeutic agent can be administered less than daily. In still other embodiments of combination therapy, the concentrated therapeutic phospholipid composition can be administered daily and the therapeutic agent can be administered more than once daily.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Concentrated Therapeutic Phospholipid Compositions

The following non-limiting examples of therapeutic compositions serve to illustrate further embodiments of the concentrated therapeutic phospholipid composition. It is to be understood that any embodiments listed in the Examples section are embodiments of the concentrated therapeutic phospholipid composition and, as such, are suitable for use in the methods and compositions described above.

Figure 1B:
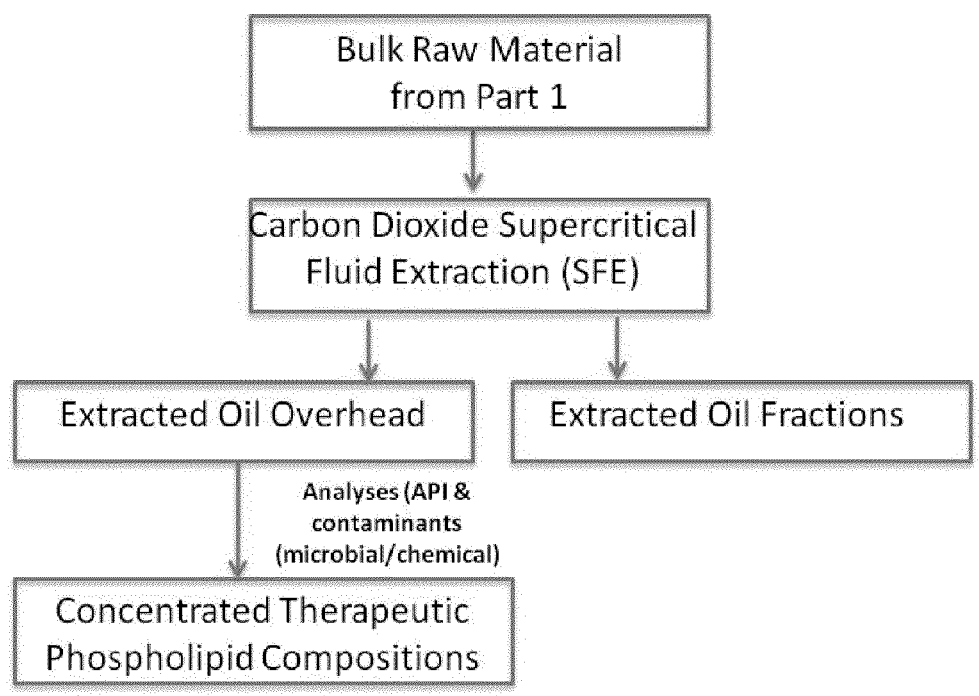
FIG. 1B depicts a flow chart for the process for making the concentrated therapeutic phospholipid compositions.
Figure 1C:
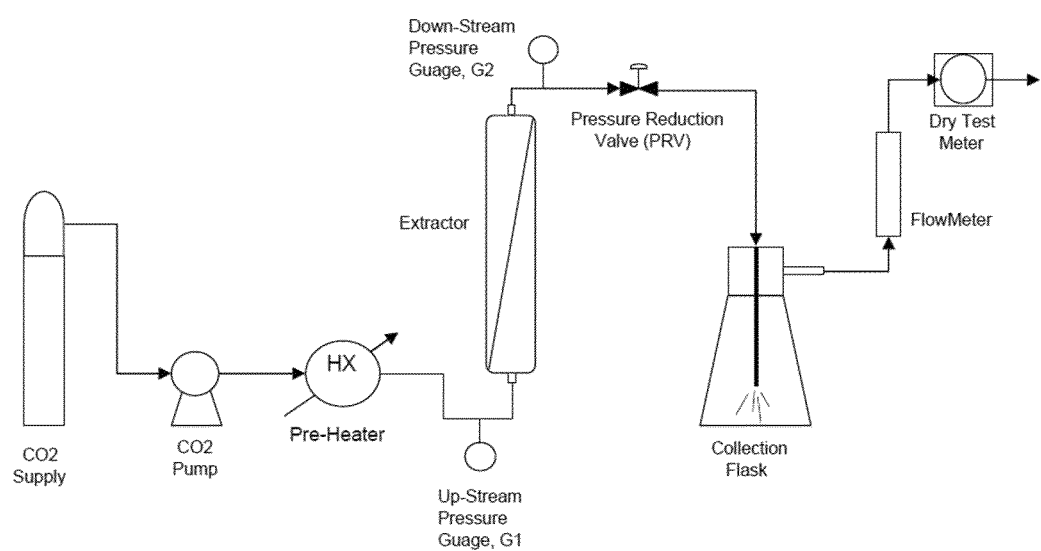
FIG. 1C depicts shows the schematic of the supercritical CO2 extraction apparatus.
Figure 2:
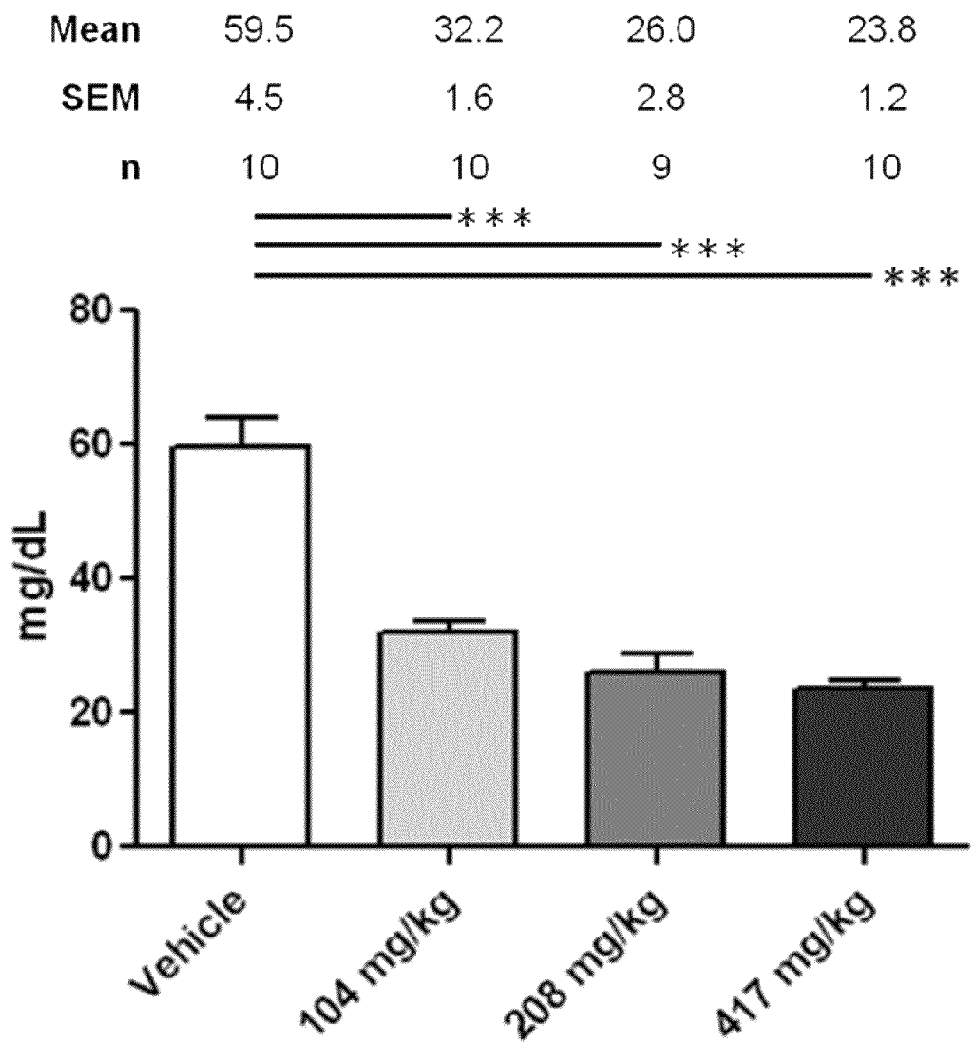
FIG. 2 depicts circulating plasma triglyceride concentration of C57BL/6 mice treated with Composition 3.
Figure 3:
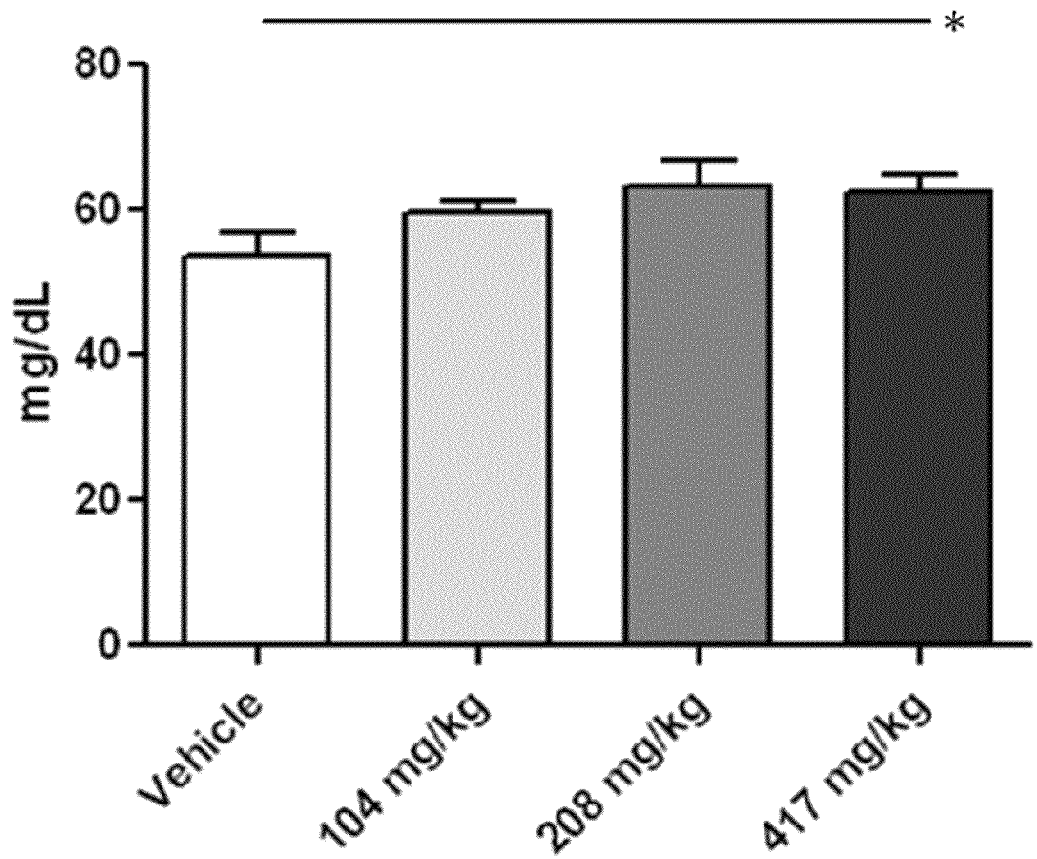
FIG. 3 depicts circulating plasma HDL-Cholesterol concentration of C57BL/6 mice treated with Composition 3.
Figure 4:
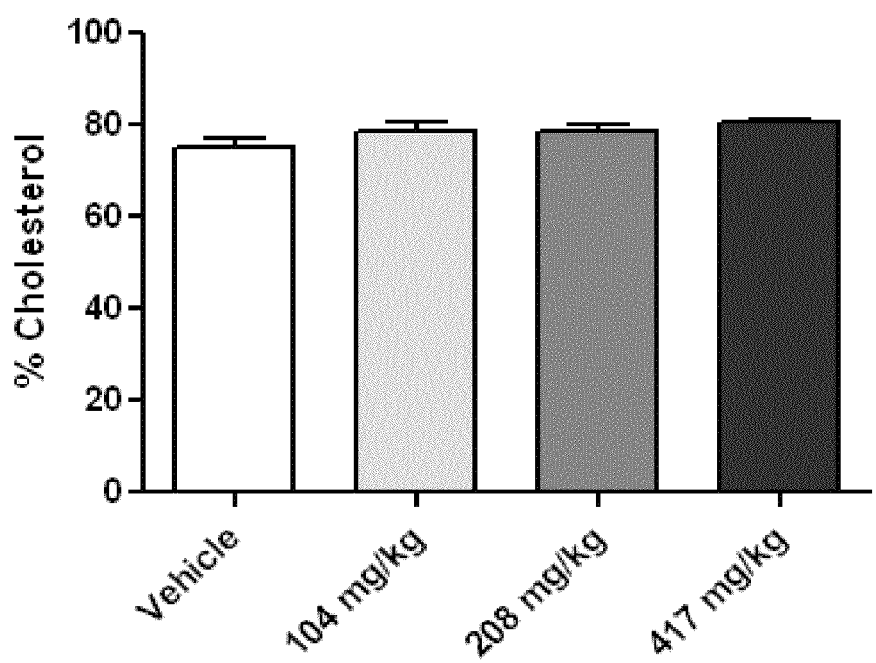
FIG. 4 depicts circulating plasma percentage of HDL-Cholesterol in C57BL/6 mice treated with Composition 3.
Figure 5:
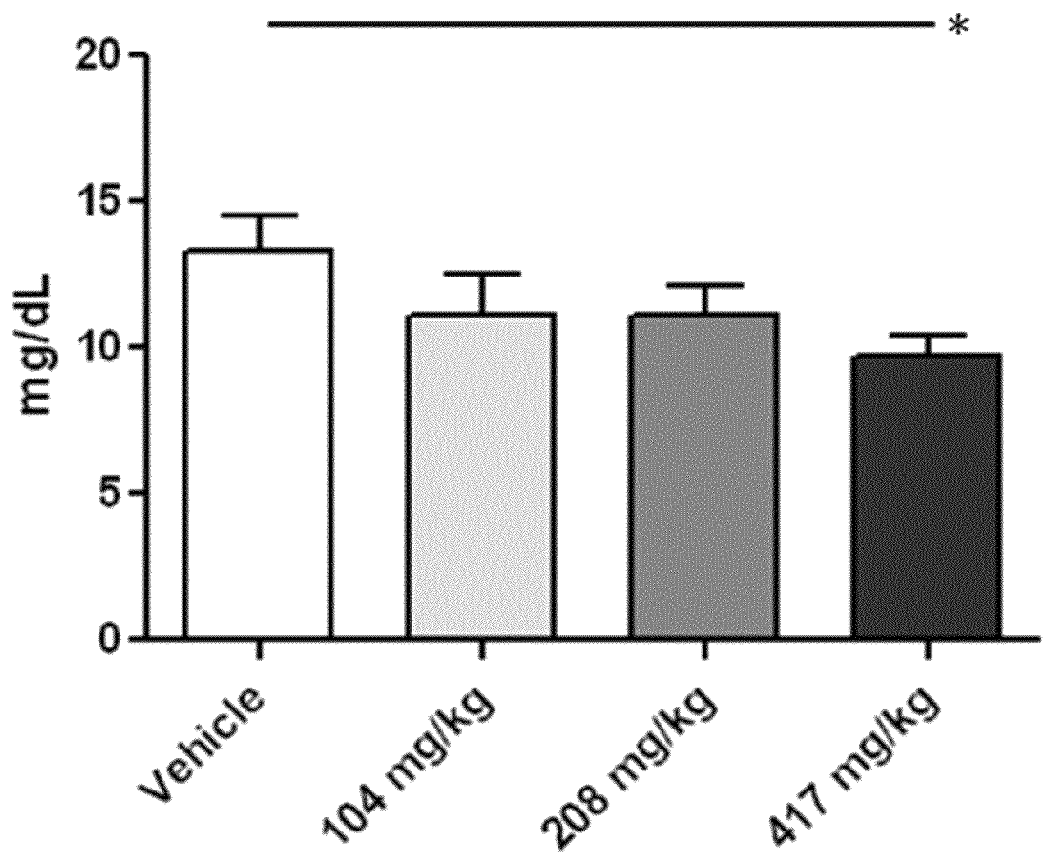
FIG. 5 depicts circulating plasma LDL-Cholesterol concentration of C57BL/6 mice treated with Composition 3.
Figure 6:
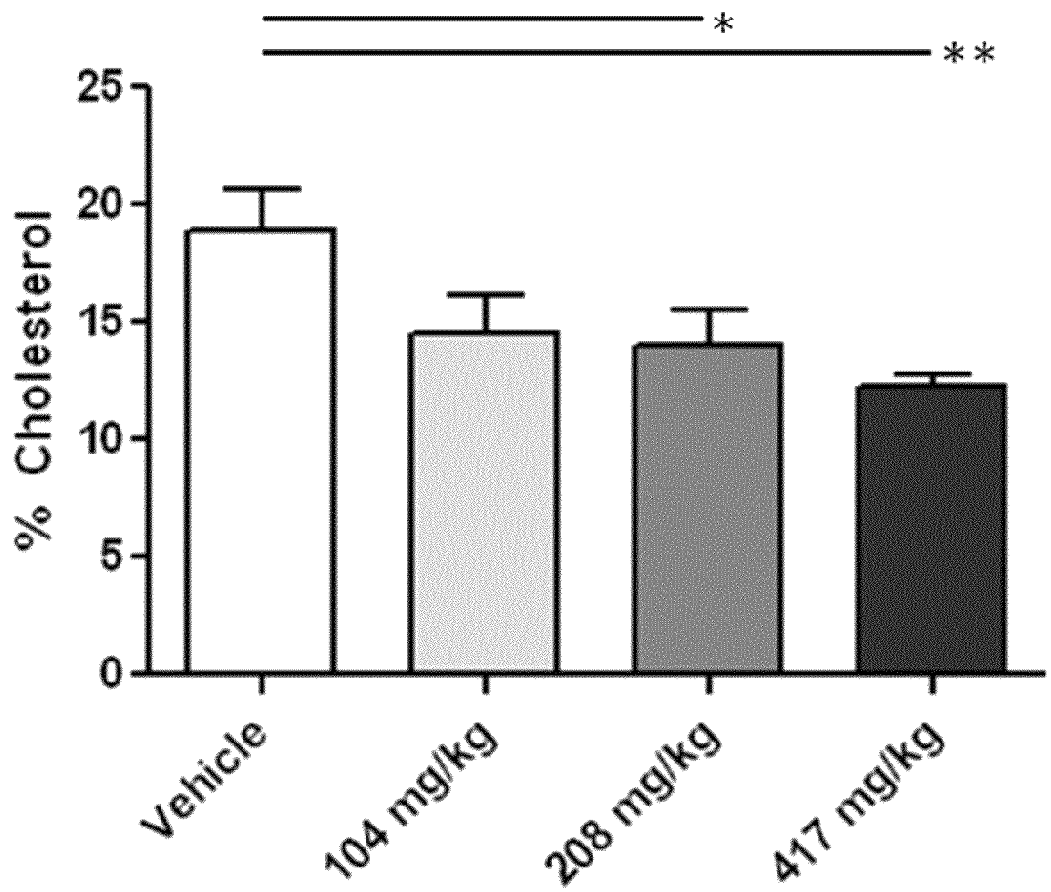
FIG. 6 depicts circulating plasma percentage of LDL-Cholesterol in C57BL/6 mice treated with Composition 3.
Figure 7:
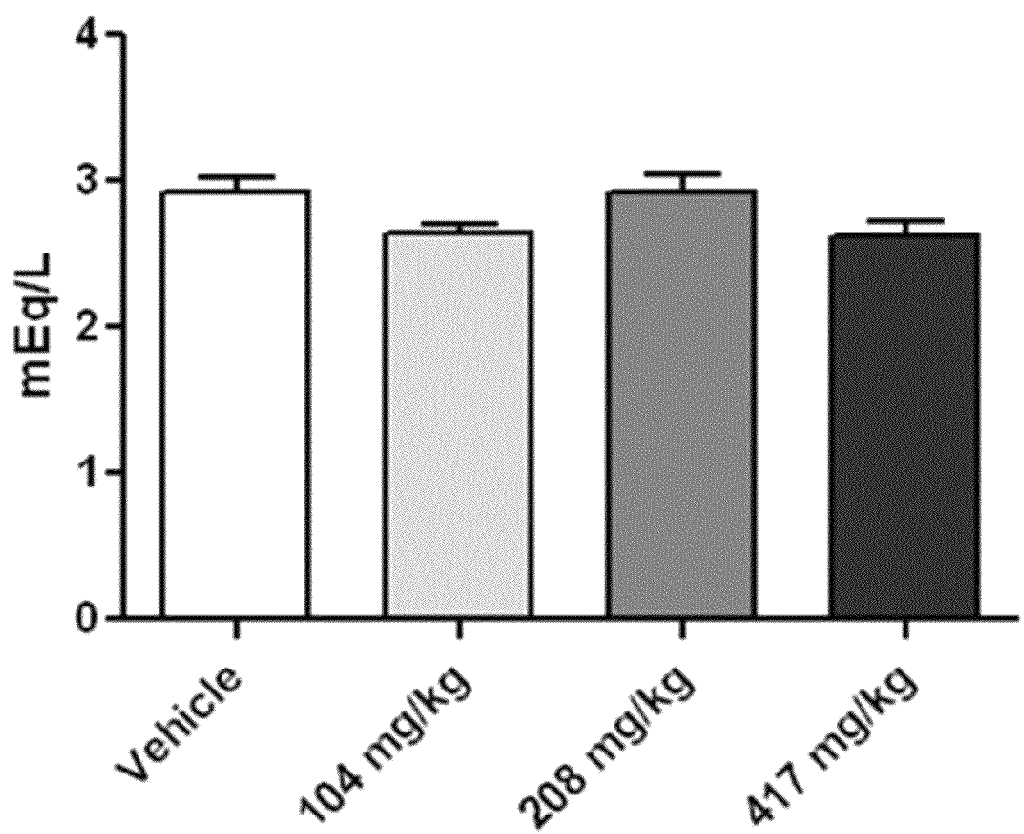
FIG. 7 depicts circulating plasma NEFA concentration of C57BL/6 mice treated with Composition 3.
Figure 8:
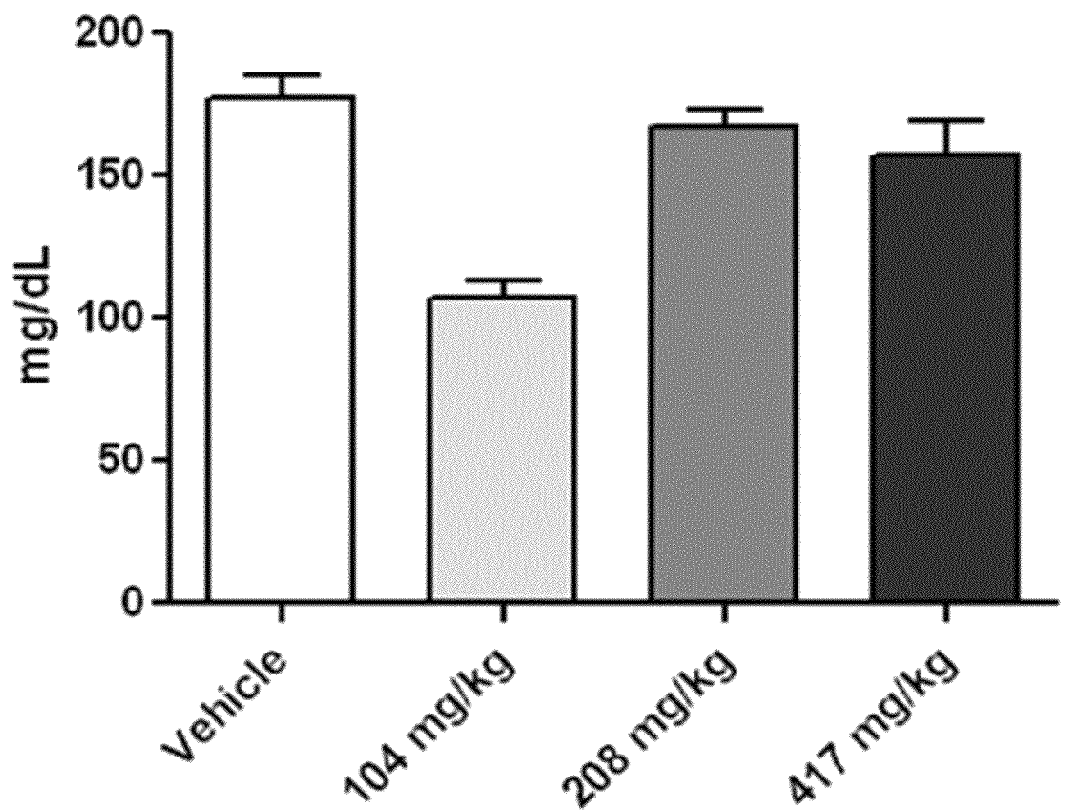
FIG. 8 depicts circulating plasma Glucose concentration of C57BL/6 mice treated with Composition 3.
Figure 9:
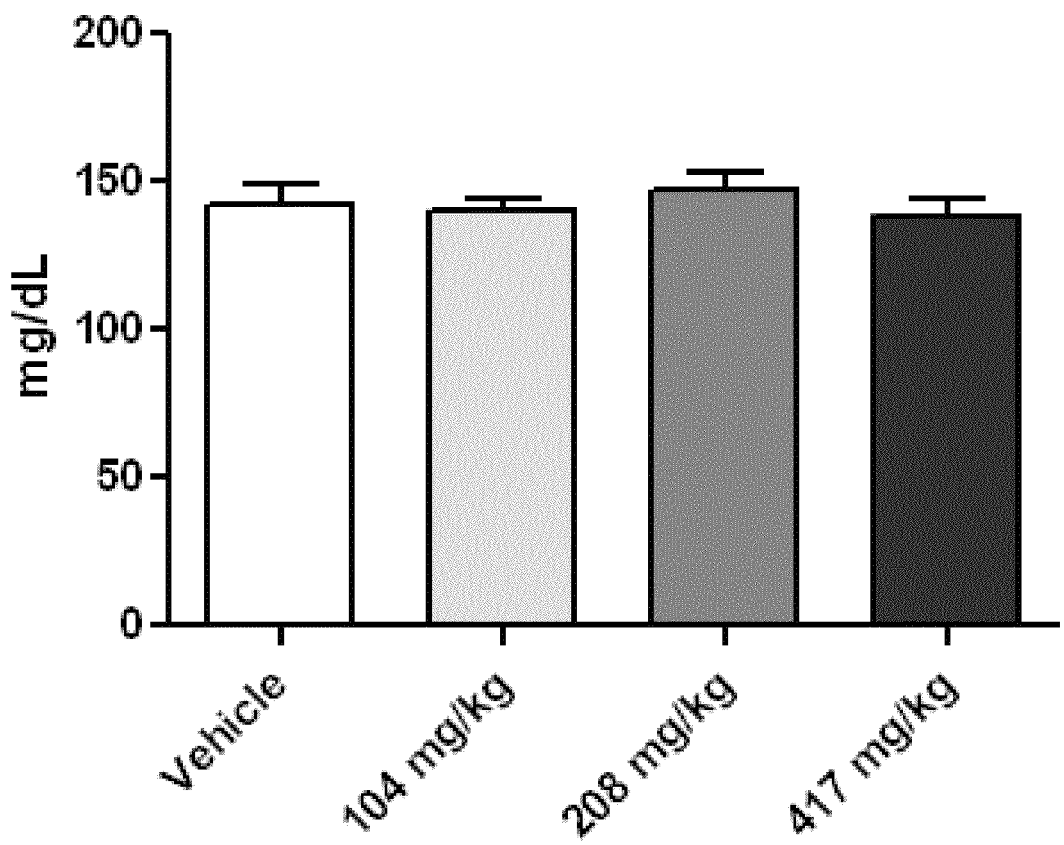
FIG. 9 depicts circulating plasma Phospholipid concentration of C57BL/6 mice treated with Composition 3.
Figure 10:
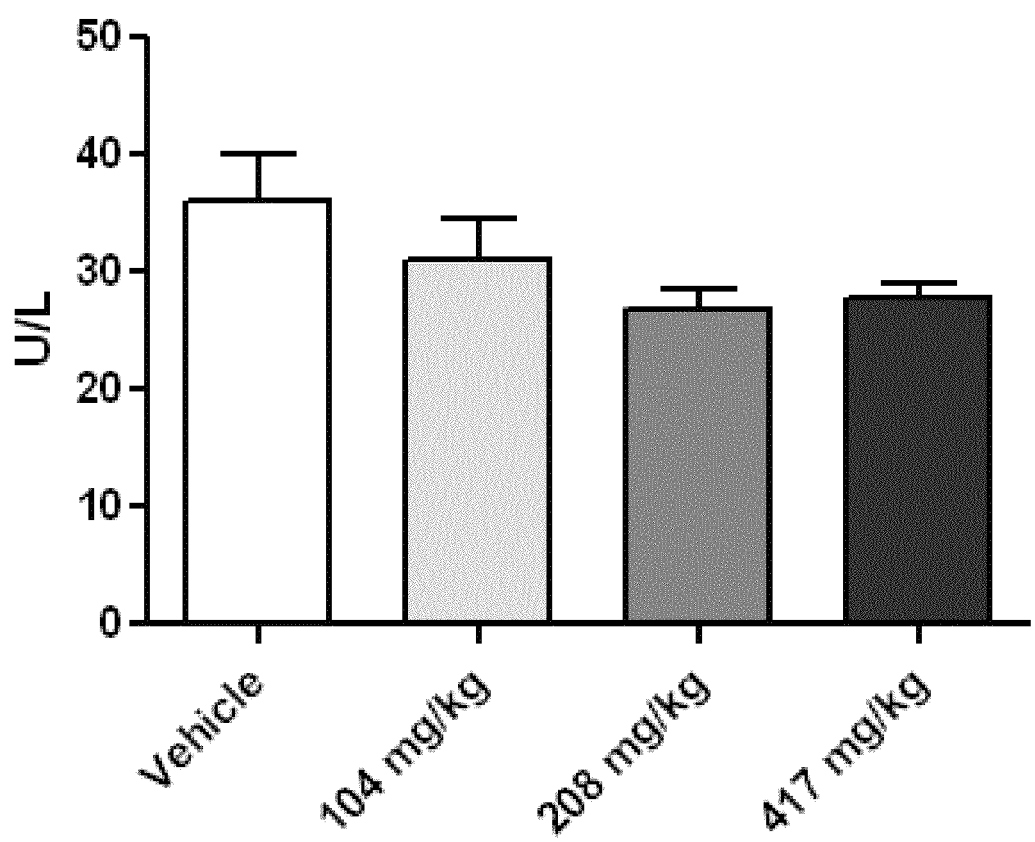
FIG. 10 depicts circulating plasma ALT concentration of C57BL/6 mice treated with Composition 3.
Figure 11:
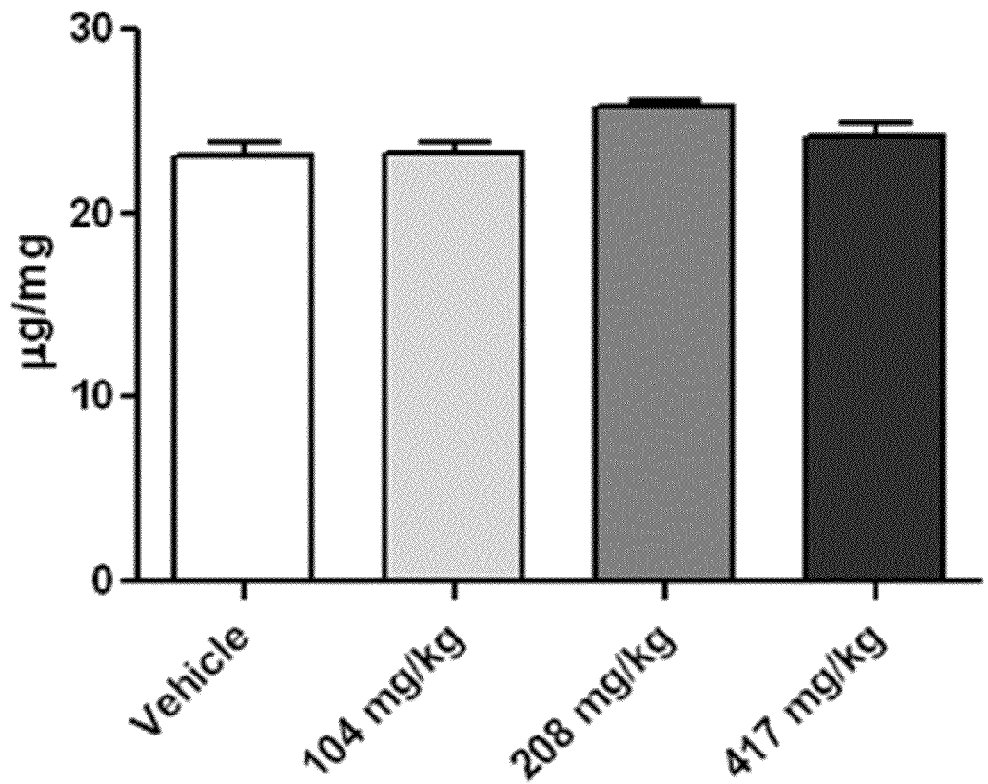
FIG. 11 depicts liver Total Cholesterol concentration of C57BL/6 mice treated with Composition 3.
Figure 12:
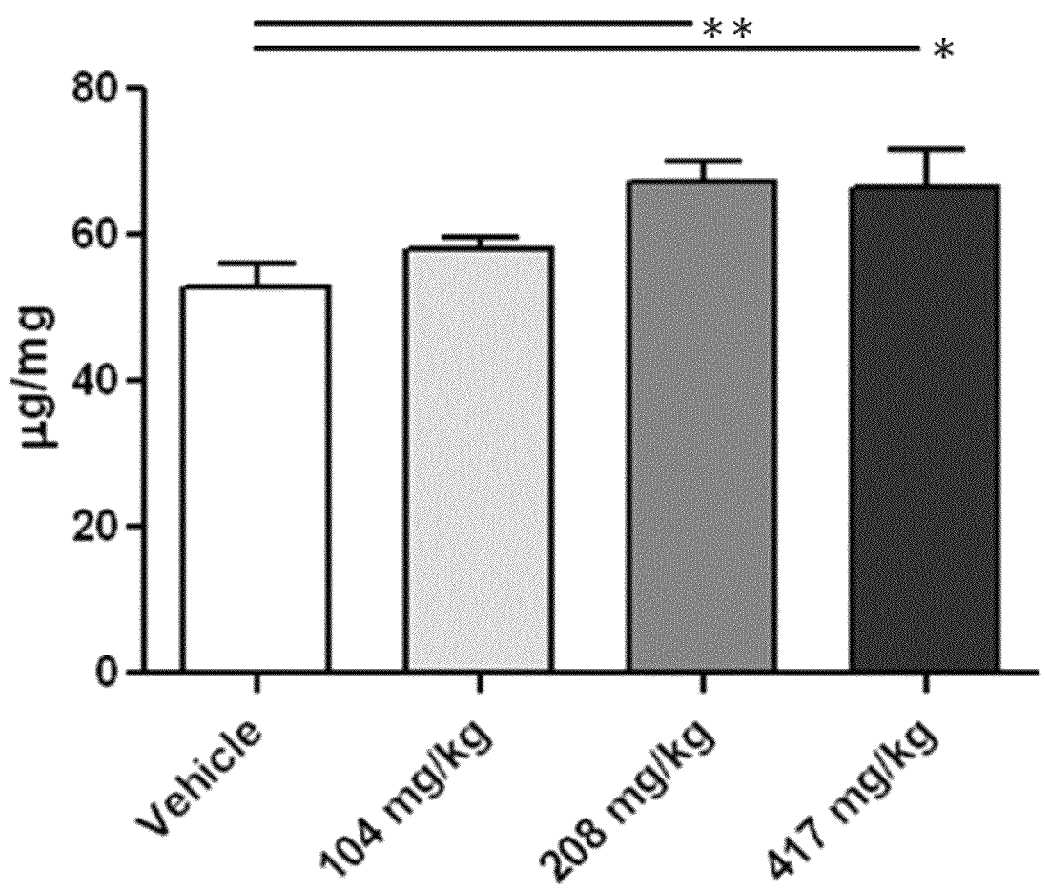
FIG. 12 depicts liver Triglyceride concentration of C57BL/6 mice treated with Composition 3.
Figure 13:
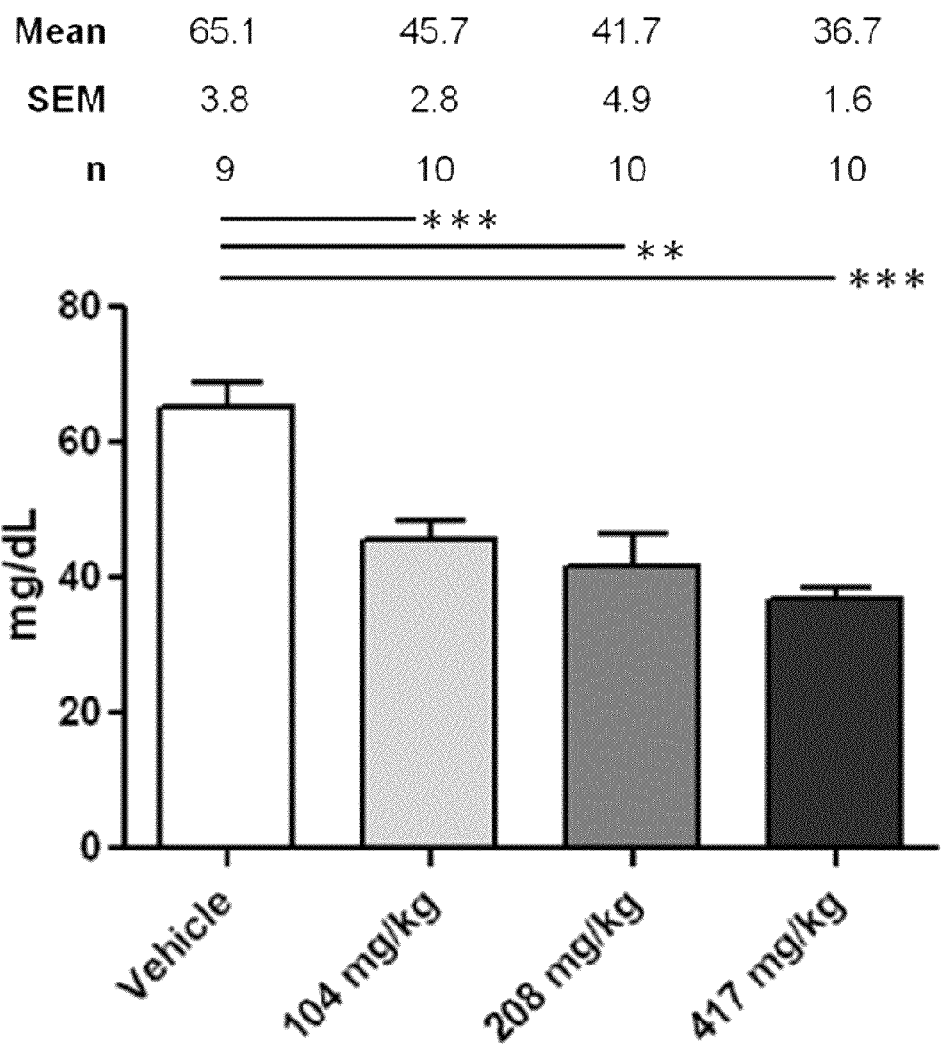
FIG. 13 depicts circulating plasma triglyceride concentration of LDLr KO mice treated with Composition 3.
Figure 14:
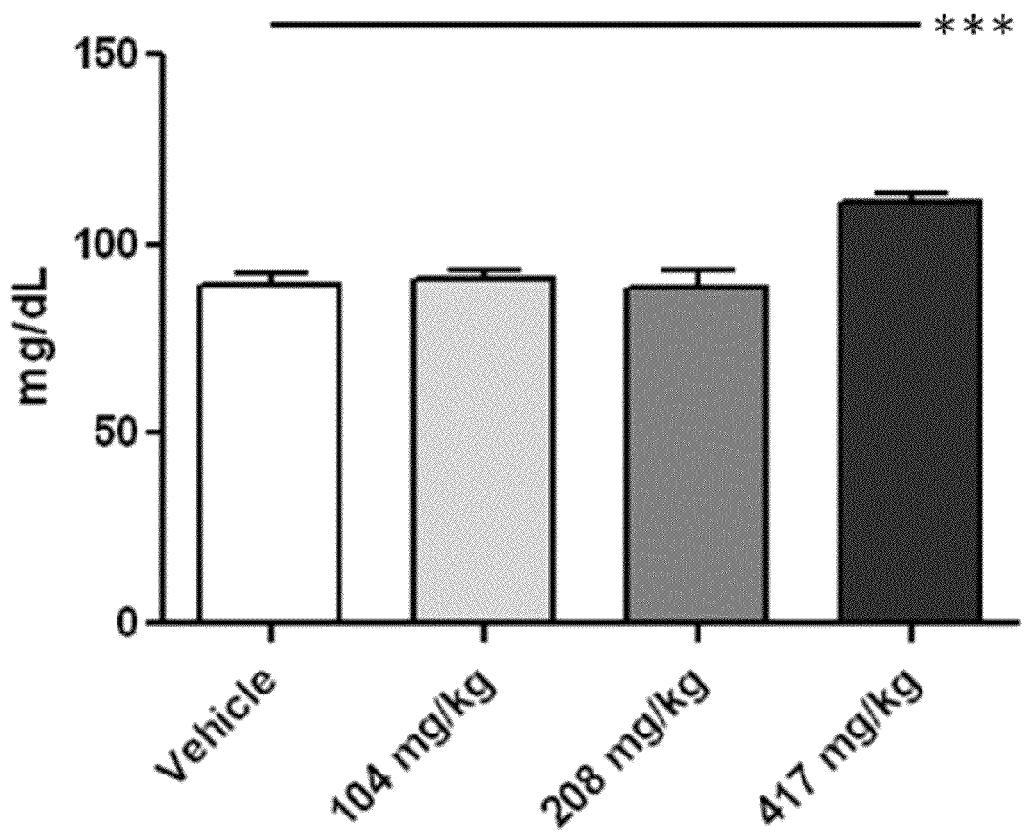
FIG. 14 depicts circulating plasma HDL-Cholesterol concentration of LDLr KO mice treated with Composition 3.
Figure 15:
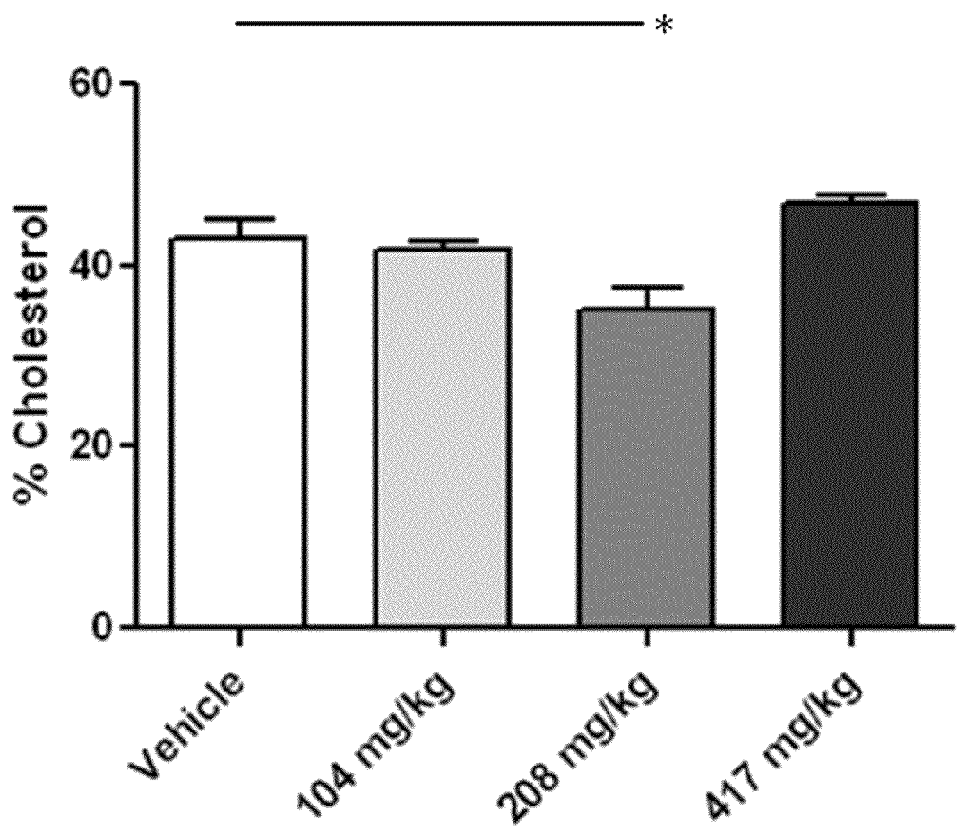
FIG. 15 depicts circulating plasma percentage of HDL-Cholesterol in LDLr KO mice treated with Composition 3.
Figure 16:
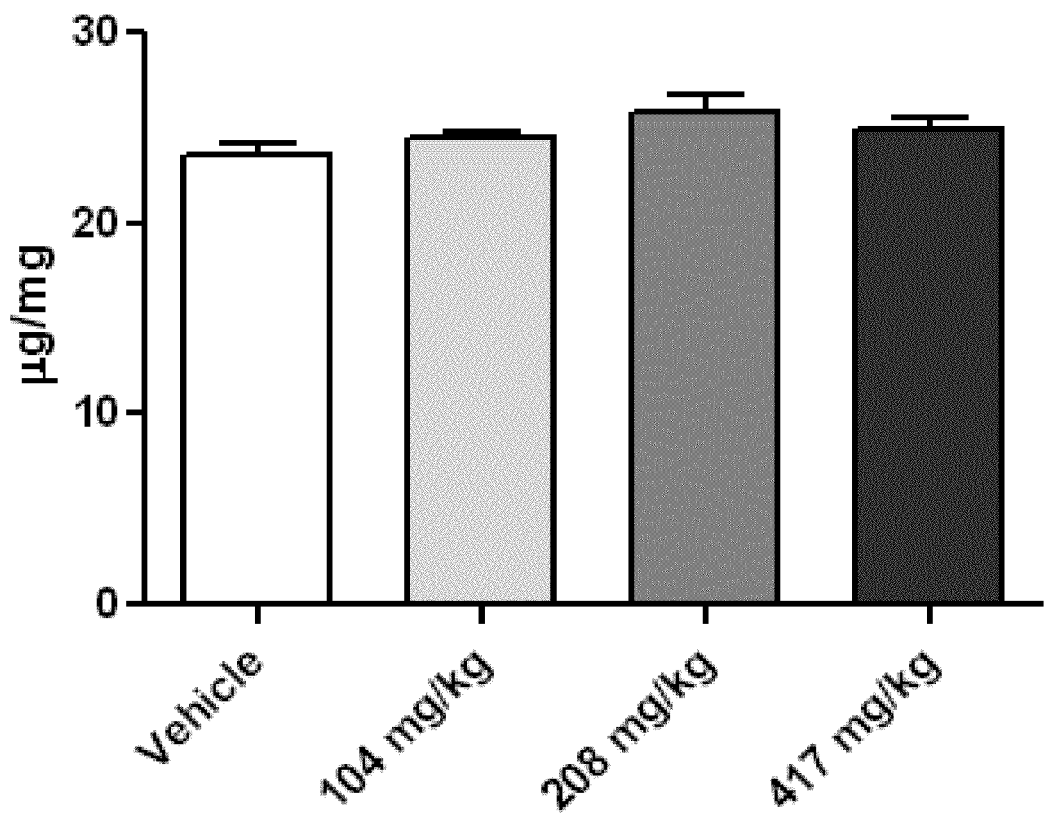
FIG. 16 depicts liver Total Cholesterol concentration of LDLr KO mice treated with Composition 3.
Figure 17:
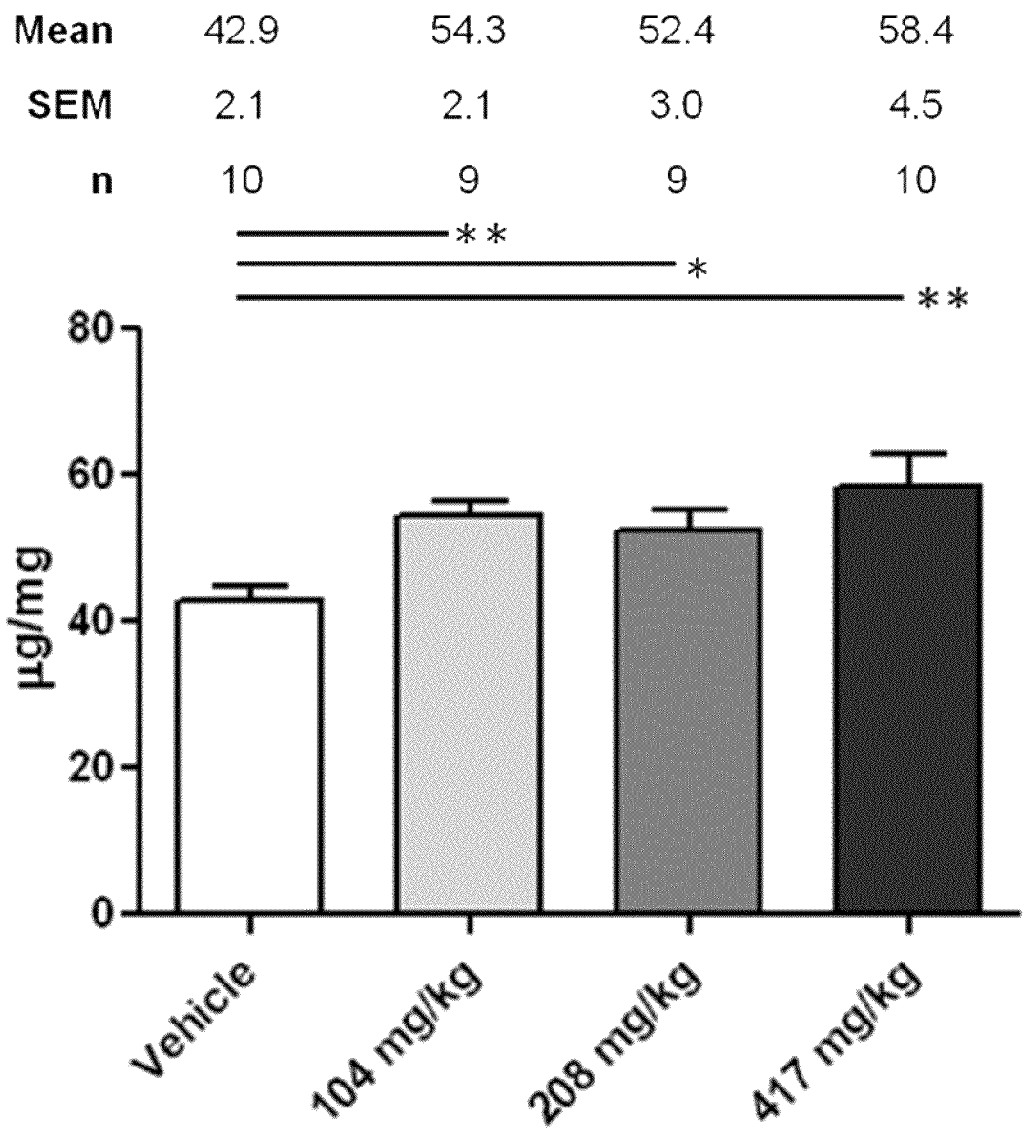
FIG. 17 depicts liver Triglyceride concentration of LDLr KO mice treated with Composition 3.

The following methods can be used to make the concentrated therapeutic phospholipid compositions (FIGS. 1A and 1B)

Step 1:

Frozen krill is mechanically crushed and incubated with a solvent in a ratio of 9:1 acetone water for 60-90 minutes at 8° C. to extract different proportions of the lipids (PL, TG and FFA) from the krill biomass. Lipids are subsequently separated from proteins and krill material by filtration under pressure (50-60 kpa). The solid phase is discarded. The soluble extract is evaporated by a continuous distillation column under vacuum to remove the solvent (acetone). The major part of the aqueous (water) fraction is separated from the lipid fraction by decantation and the remaining water removed by evaporation under vacuum and gentle heating. Those fractions are dosed, analyzed, and blended to constitute an intermediary krill oil product which is re-analyzed to achieve desired specifications±5%: EPA (15 g/100 g), DHA (9 g/100 g), total phospholipids (42 g/100 g) and astaxanthin's forms (125 mg/100 g).

Step 2:

100.5 g of received krill oil from step 1 was charged to a 300 ml extraction vessel (ID=0.68"). The extractor was sealed, pre-heated $CO_2$ at 55° C. was introduced from the bottom, and the pressure in the extractor was maintained at 5,000 psi using a diaphragm $CO_2$ pump. The flow of $CO_2$ was continued in the upflow direction through the extractor and was expanded to atmospheric pressure through a pressure-reduction-valve (PRV) so that the dissolved material in the $CO_2$ precipitated and collected in the flask. The flow rate and volume of $CO_2$ exiting the flask was measured with a flowmeter and dry test meter (DTM). A total of 7200 g of $CO_2$ was passed through the extractor (solvent to feed ratio, S/F=72) and 34.1% of the charge was removed by the $CO_2$. The flow of about 25 Standard Liters/min of $CO_2$ was maintained during the course of the test and the total time of extraction was about 160 min. The extractor was isolated and the $CO_2$ was vented to atmosphere. The extractor was opened and the un-extracted material (raffinate-product) was removed from the vessel.

Step 3:

SC $CO_2$ Extraction to produce 90+% OM3:PLs. 9.44 g of oil was mixed with inert packing and charged to the extractor. The procedure carried out similar to that described in step 2 except more aggressive extraction conditions were used with the pressure and temperature in the extractor maintained at 10,000 psi and 70° C. A total S/F ratio of 200 was used f;

therefore, about 1900 g of CO2 was flowed through the extractor. A flow rate of CO2 of about 10 Standard Liters/min was maintained; therefore, the total run time for this test was 105 min A total of 56.3% of the charge was extracted from this oil during the course of the run. The extractor was isolated, the CO2 vented to atmosphere, the vessel opened, and the resulting raffinate-product scraped off the inert packing. This unextracted material analyzed to be 91% OM3:PLs.

Composition 1

| | 47% OM3:PL | | |
|---|---|---|---|
| *Total lipids as FA$_{TG}$ | g/100 g oil | 61.3 | (100) |
| *Omega-3 | g/100 g oil | 14.1 | (22.5) |
| *EPA | g/100 g oil | 7.4 | (11.6) |
| *DHA | g/100 g oil | 3.8 | (6.1) |
| *DPA | g/100 g oil | 0.2 | (0.3) |
| *Omega-6 | g/100 g oil | 10.8 | (18.3) |
| *Linoleic acid | g/100 g oil | 10.6 | (18.0) |
| *Omega-9 | g/100 g oil | 6.6 | (11.6) |
| *Oleic acid | g/100 g oil | 6.1 | (10.8) |
| *Sat. FA$_{TG}$ | g/100 g oil | 21.4 | (36.1) |
| *Monounsat. FA$_{TG}$ | g/100 g oil | 13.9 | (23.1) |
| *Polyunsat.$_{TG}$ | g/100 g oil | 26.0 | (40.7) |
| *EPA as FA$_{TG}$ | g/100 g oil | | 7.7 |
| *DHA as FA$_{TG}$ | g/100 g oil | | 3.9 |
| Water | % | | 0.8 |
| Color | — | | Red orange |
| Odor | — | | Slightly rancid |
| Total carotenoids | mg/100 g oil | | 36.0 |
| Astaxanthine | mg/100 g oil | | 65.3 |
| Astaxanthine | % diester | | 83.1 |
| | % monoester | | 16.9 |
| | % free | | 0.0 |
| Peroxide Index | mEq peroxide/kg | | 1.0 |
| p-Anisidine Index | — | | 2.0 |
| Iodine Index | gI$_2$/100 g oil | | 101.1 |
| Saponification Index | mg KOH/g oil | | 214.1 |
| Indice acide | mg KOH/g oil | | 17.2 |
| Total fat | % | | |
| Free fatty acid | % as oleic acid | | 5.2 |
| Triglycerides | % | | 36.5 |
| Viscosity | cP | | 1323.0 |
| ash | % | | 5.0 |
| Vitamin A | UI/g Oil | | 40.4 |
| Vitamin E | UI/g Oil | | 0.1 |
| Total phospholipids | g/100 g oil | | 47.2 |
| Phospholipid profile | TLC | | — |
| | % LPC | | 3.7 |
| | % PC | | 53.6 |
| | % PS | | 24.7 |
| | % PE | | 16.4 |
| | % PA | | 1.7 |
| Molecular mass PL | g/mol | | 773.8 |

Composition 2

| 53% OM3:PL | | |
|---|---|---|
| Total lipids as fatty acids (FA) TG | g/100 g oil | 69.80 |
| Total Omega-3 | g/100 g oil | 31.30 |
| C 20:5 (n = 3) EPA | g/100 g oil | 13.90 |
| C 22:6 (n = 3) DHA | g/100 g oil | 10.10 |
| C 22:5 (n = 3) DPA | g/100 g oil | 0.40 |
| Total Omega-6 | g/100 g oil | 1.60 |
| linoleic acid—LA | g/100 g oil | 1.30 |
| Total Omega-9 | g/100 g oil | 6.10 |
| oleic acid—OA | g/100 g oil | 5.70 |
| Saturated FA | g/100 g oil | 21.10 |
| Monounsaturated FA | g/100 g oil | 14.50 |
| Polyunsaturated FA | g/100 g oil | 34.20 |
| EPA as FA | g/100 g oil | 14.40 |
| DHA as FA | g/100 g oil | 10.50 |
| PHOSPHOLIPID PROFILE | | |
| total | g/100 g oil | 52.30 |
| lysophosphatidyl choline—LPC | % | 10.80 |
| sphingomyelin—SM | % | 0.10 |
| phsophatidyl choline—PC | % | 79.70 |
| phsophatidyl serine—PS | % | |
| phsophatidyl inositol—PI | % | |
| phosphatidyl ethanolamine—PE | % | 9.40 |
| PA | % | 0.00 |
| CAROTENOIDS | | |
| total | mg/100 g oil | 92.60 |
| total astaxanthin - AST | mg/100 g oil | 161.60 |
| AST diester | | 62.00 |
| AST monoester | | 35.00 |
| AST free | | 3.00 |

Composition 3

| 66% OM3:PL | | |
|---|---|---|
| Total lipids as fatty acids (FA) TG | g/100 g oil | 74.2 |
| Total Omega-3 | g/100 g oil | 39.8 |
| C 20:5 (n = 3) EPA | g/100 g oil | 21.7 |
| C 22:6 (n = 3) DHA | g/100 g oil | 14.1 |
| C 22:5 (n = 3) DPA | g/100 g oil | 0.5 |
| Total Omega-6 | g/100 g oil | 1.7 |
| linoleic acid—LA | g/100 g oil | 1.3 |
| Total Omega-9 | g/100 g oil | 5.8 |
| oleic acid—OA | g/100 g oil | 5.1 |
| Saturated FA | g/100 g oil | 18.0 |
| Monounsaturated FA | g/100 g oil | 13.2 |
| Polyunsaturated FA | g/100 g oil | 43.1 |
| EPA as FA | g/100 g oil | 22.6 |
| DHA as FA | g/100 g oil | 14.6 |
| PHOSPHOLIPID PROFILE | | |
| total | g/100 g oil | 66.2 |
| lysophosphatidyl choline—LPC | % | 10.7 |
| phsophatidyl choline—PC | % | 75.3 |
| phosphatidyl ethanolamine—PE | % | 11.8 |
| other | % | 2.2 |
| CAROTENOIDS | | |
| total | mg/100 g oil | 273.4 |
| total astaxanthin - AST | mg/100 g oil | 466.8 |
| AST diester | % | 57.4 |
| AST monoester | % | 40.7 |
| AST free | % | 1.9 |

Composition 4

| 80% OM3:PL | | |
|---|---|---|
| Total lipids as fatty acids (FA) TG | g/100 g oil | 68.35 |
| Total Omega-3 | g/100 g oil | 37.90 |
| C 20:5 (n = 3) EPA | g/100 g oil | 20.40 |
| C 22:6 (n = 3) DHA | g/100 g oil | 12.95 |
| C 22:5 (n = 3) DPA | g/100 g oil | 0.48 |
| Total Omega-6 | g/100 g oil | 1.45 |
| linoleic acid—LA | g/100 g oil | 1.26 |

Composition 5

-continued

| 80% OM3:PL | | |
|---|---|---|
| Total Omega-9 | g/100 g oil | 4.93 |
| oleic acid—OA | g/100 g oil | 4.35 |
| Saturated FA | g/100 g oil | 16.15 |
| Monounsaturated FA | g/100 g oil | 11.21 |
| Polyunsaturated FA | g/100 g oil | 40.99 |
| EPA as FA | g/100 g oil | 21.30 |
| DHA as FA | g/100 g oil | 13.50 |
| PHOSPHOLIPID PROFILE | | |
| total | g/100 g oil | 80.00 |
| lysophosphatidyl choline—LPC | % | 9.20 |
| sphingomyeline—SM | % | 0.20 |
| phsophatidyl choline—PC | % | 80.60 |
| phsophatidyl serine—PS | % | 1.10 |
| phsophatidyl inositol—PI | % | 0.10 |
| phosphatidyl ethanolamine—PE | % | 7.50 |
| PA | % | 1.30 |
| CAROTENOIDS | | |
| total | mg/100 g oil | 180.4 |
| total astaxanthin - AST | mg/100 g oil | 325.5 |
| AST diester | % | 68.45 |
| AST monoester | % | 29.27 |
| AST free | % | 2.28 |

Composition 5

| 90% OM3:PL | | |
|---|---|---|
| *Total lipids as $FA_{TG}$ | g/100 g oil | 63.9 |
| *Omega-3 | g/100 g oil | 35.1 |
| *EPA | g/100 g oil | 18.9 |
| *DHA | g/100 g oil | 12.2 |
| *DPA | g/100 g oil | 0.5 |
| *Omega-6 | g/100 g oil | 1.3 |
| *Linoleic acid | g/100 g oil | 1.2 |
| *Omega-9 | g/100 g oil | 4.6 |
| *Oleic acid | g/100 g oil | 3.9 |
| *Sat. $FA_{TG}$ | g/100 g oil | 15.8 |
| *Monounsat. $FA_{TG}$ | g/100 g oil | 10.2 |
| *Polyunsat.$_{TG}$ | g/100 g oil | 37.9 |
| *EPA as $FA_{TG}$ | g/100 g oil | 19.7 |
| *DHA as $FA_{TG}$ | g/100 g oil | 12.7 |
| Acetone | Ppm | 1.6 |
| Humidity and volatiles | % | 1.7 |
| Water | % | 1.9 |
| Color | — | Red chili |
| Odor | — | shellfish |
| Total carotenoids | mg/100 g oil | 168.9 |
| Astaxanthine | mg/100 g oil | 309.3 |
| Astaxanthine | % Diester | 73.1 |
|  | % Monoester | 25.3 |
|  | % Libre | 1.6 |
| Index p-Anisidine | — | 3.1 |
| Index acid | mg KOH/g oil | 33.6 |
| Index iodine | g$I_2$/100 g oil |  |
| Index saponification | mg KOH/g oil |  |
| Index Peroxide | mEq peroxyde/kg | 0.1 |
| Vitamin A | UI/g Oil | 15.2 |
| Vitamin E | UI/g Oil | 0.3 |
| Fatty acid total | % | 97.6 |
| Viscosity | cP |  |
| Total phospholipids | g/100 g oil | 90.6 |
| Phospholipid profile | TLC | — |
|  | % LPC | 13.5 |
|  | % SM | 0.4 |
|  | % PC | 76.3 |
|  | % Other PL | 1.2 |
|  | % PE | 7.9 |
|  | % PA | 0.8 |
| Triglycerides | % | 0.0 |

Composition 6

| 70% OM3:PL derived from Squid | | |
|---|---|---|
| *Total lipids as $FA_{TG}$ | g/100 g oil | 54.5 |
| *Omega-3 | g/100 g oil | 29.1 |
| *EPA | g/100 g oil | 8.9 |
| *DHA | g/100 g oil | 18.3 |
| *DPA | g/100 g oil | 0.2 |
| *Omega-6 | g/100 g oil | 0.7 |
| *Linoleic acid | g/100 g oil | 0.3 |
| *Omega-9 | g/100 g oil | 4.2 |
| *Oleic acid | g/100 g oil | 2.0 |
| *Sat. $FA_{TG}$ | g/100 g oil | 16.9 |
| *Monounsat. $FA_{TG}$ | g/100 g oil | 6.8 |
| *Polyunsat.$_{TG}$ | g/100 g oil | 30.9 |
| *EPA as $FA_{TG}$ | g/100 g oil | 9.3 |
| *DHA as $FA_{TG}$ | g/100 g oil | 19.1 |
| Humidity (calmar) | % |  |
| Indice acide | mg KOH/g oil | 55.7 |
| Vitamin A | UI/g Oil |  |
| Vitamin E | UI/g Oil |  |
| Fatty acid total | % | 2.7 |
| Total carotenoids | mg/100 g oil | 8.3 |
| Astaxanthine | mg/100 g oil | 13.2 |
| Astaxanthine | % diester | 42.5 |
|  | % monoester | 35.6 |
|  | % libre | 21.9 |
| Total phospholipids | g/100 g oil | 70.8* |
| Phospholipid profile | TLC | — |
|  | % LPC | 12.4 |
|  | % SM | 7.8 |
|  | % PC | 55.8 |
|  | % other | 2.0 |
|  | % PE | 22.0 |
|  | % PA | 6.4 |
| Triglycerides | % | 25.0 |
| Free fatty acid | % as oleic acid | 3.2 |
| Index p-Anisidine | — | 4.3 |
| Index Peroxide | mEq peroxyde/kg | 0.6 |
| **PM Phospholipids (g/mol) |  | 847.14 |
| Profile of Fatty Acids of the PL | | |
| *Total lipids as FA | g/100 g PL | 53.9 |
| *Oméga-3 | g/100 g PL | 28.6 |
| *EPA | g/100 g PL | 9.0 |
| *DHA | g/100 g PL | 18.3 |
| *DPA | g/100 g PL | 0.2 |
| *Omega-6 | g/100 g PL | 0.5 |
| *Linoleic acid | g/100 g PL | 0.2 |
| *Omega-9 | g/100 g PL | 3.6 |
| *Oleic acid | g/100 g PL | 1.5 |
| *Sat. FA | g/100 g PL | 18.3 |
| *Monounsat. FA | g/100 g PL | 5.4 |
| *Polyunsat. FA | g/100 g PL | 30.2 |

Biological Examples

Example 1

Managing Dyslipidemia in Three Murine Phenotypes

The aim of this study was to examine the effects of Composition 3 in three age-/sex-matched murine phenotypes representative of (1) normal healthy non-obese normoglycemic control (C57BL6) versus (2) hyperdislipidemic LDL-receptor gene knockout (LDLr−/−) or (3) human apoA-I transgenic mice (Jackson Labs) at 12-w of age: 27.5±0.7 vs 25.6±0.7 vs 29.2±0.8 gr., respectively; n=7-10/gr. kept according to local and national ethic regulations, fed a normal vs a Western-diet regime and water ad libitum. Data are presented as mean±sem and statistics assessed by t-test (unpaired, two-tail) (v5-GraphPad Prism).

Figure 18:
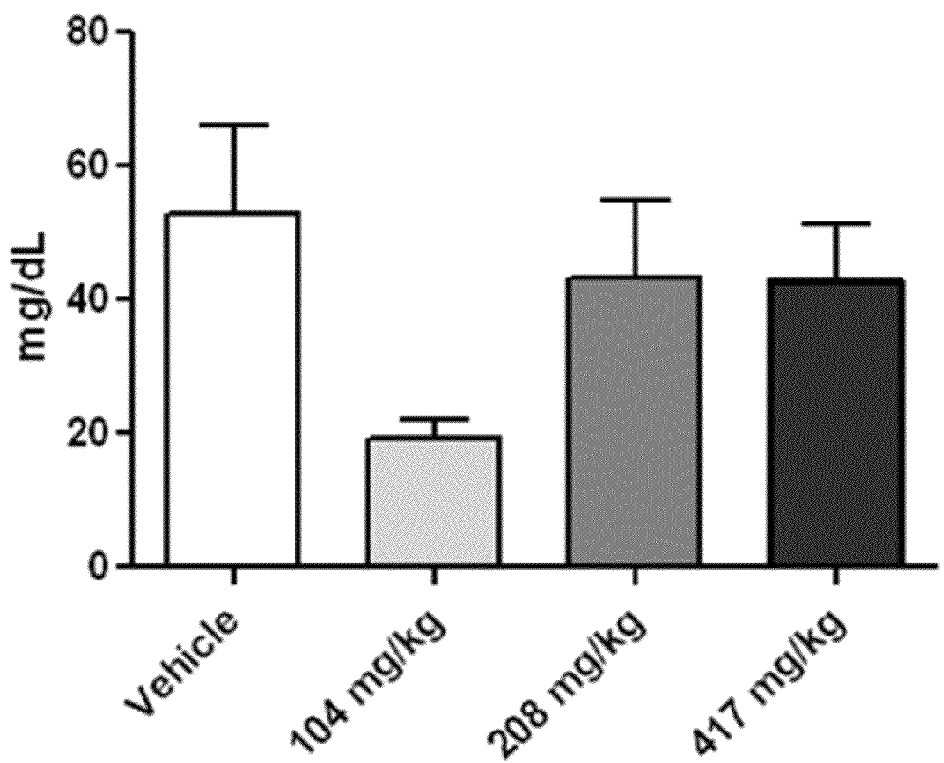
FIG. 18 depicts circulating plasma Triglyceride concentration of ApoA-1 CET Tg mice treated with Composition 3.
Figure 19A:
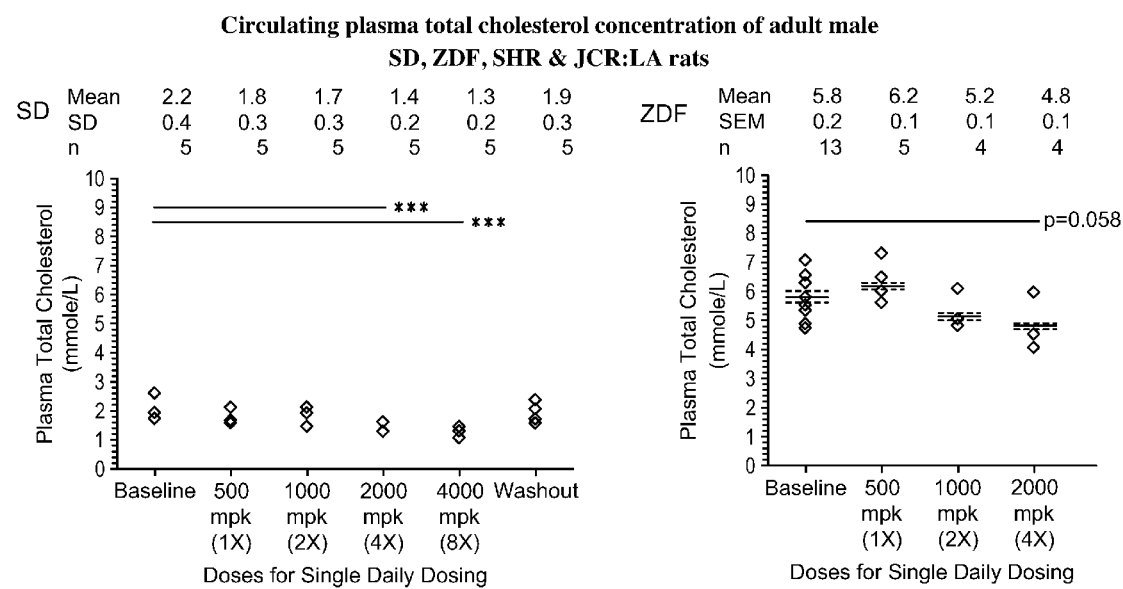
FIG. 19 depicts circulating plasma total cholesterol concentration of adult male SD, ZDF, SHR and JCR:LA rats.
Figure 19B:
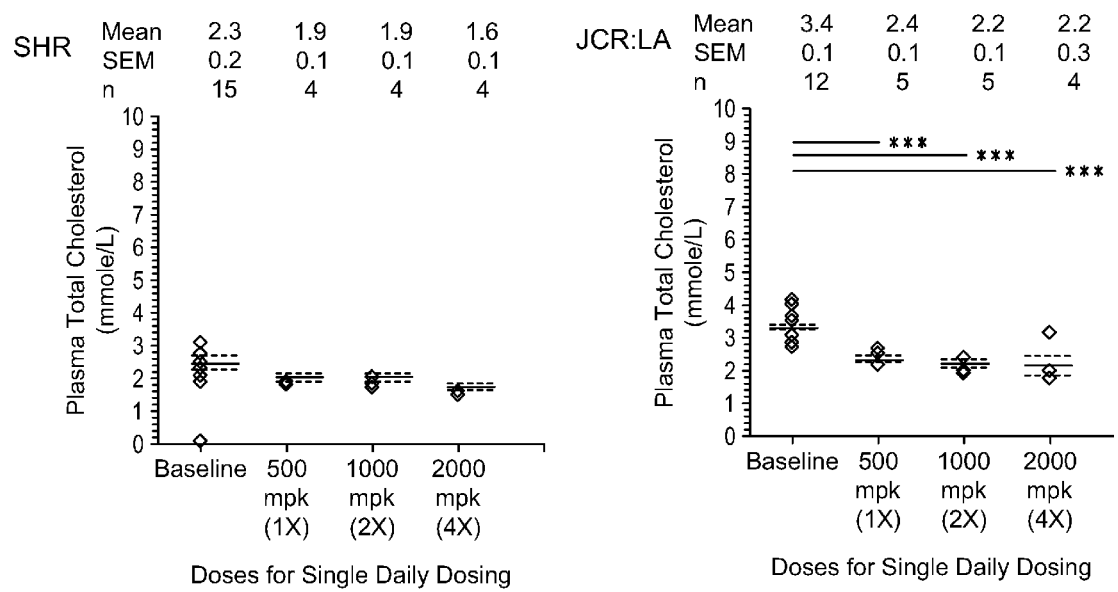
Figure 20:
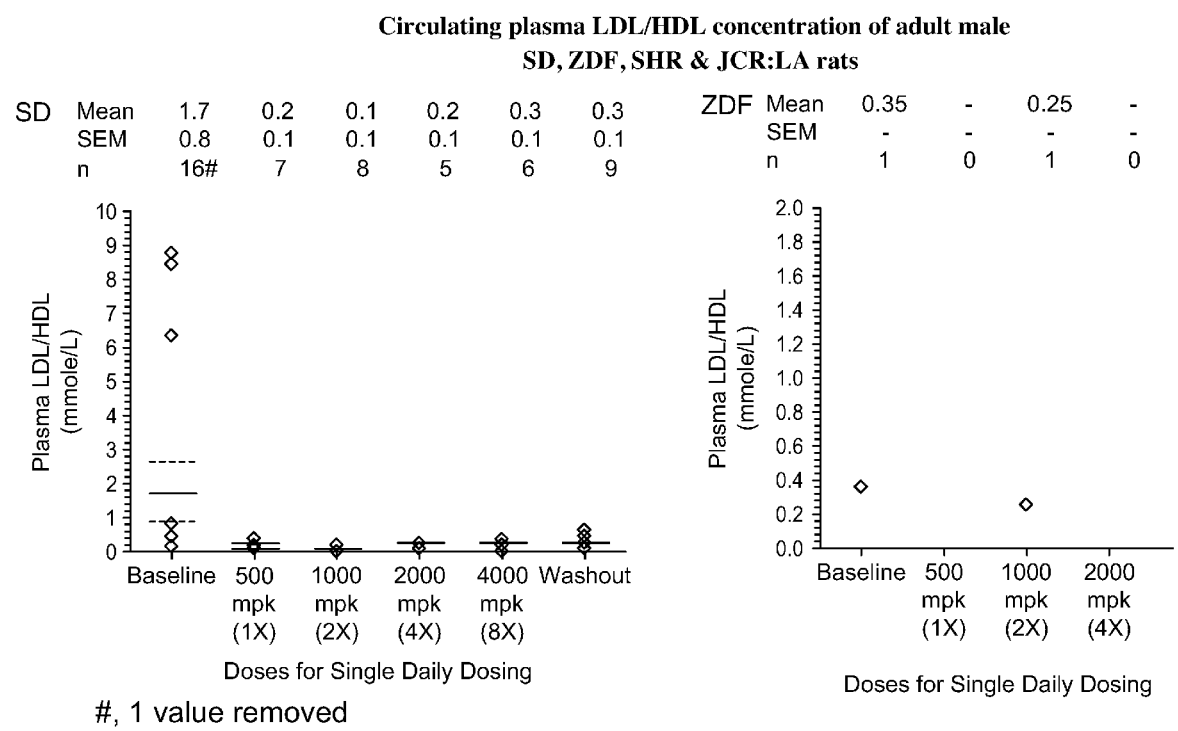
FIG. 20 depicts circulating plasma total cholesterol concentration of adult male SD, ZDF, SHR and JCR:LA rats.
Figure 21:
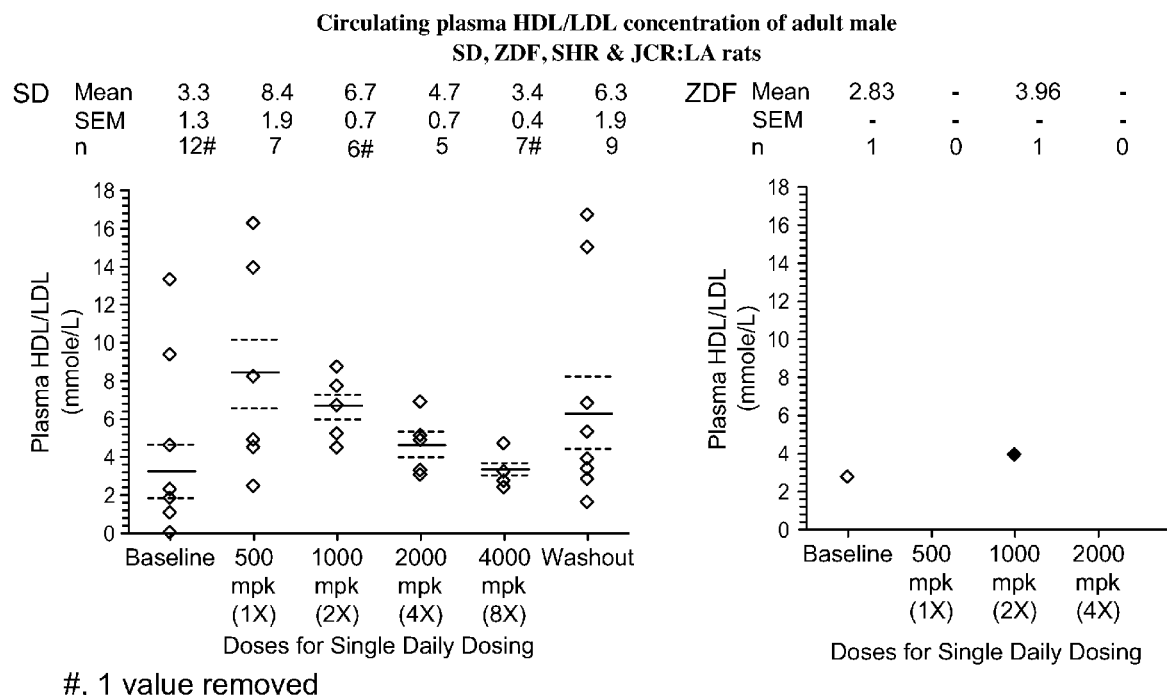
FIG. 21 depicts circulating plasma HDL/LDL concentration of adult male SD, ZDF, SHR and JCR:LA rats.
Figure 22:
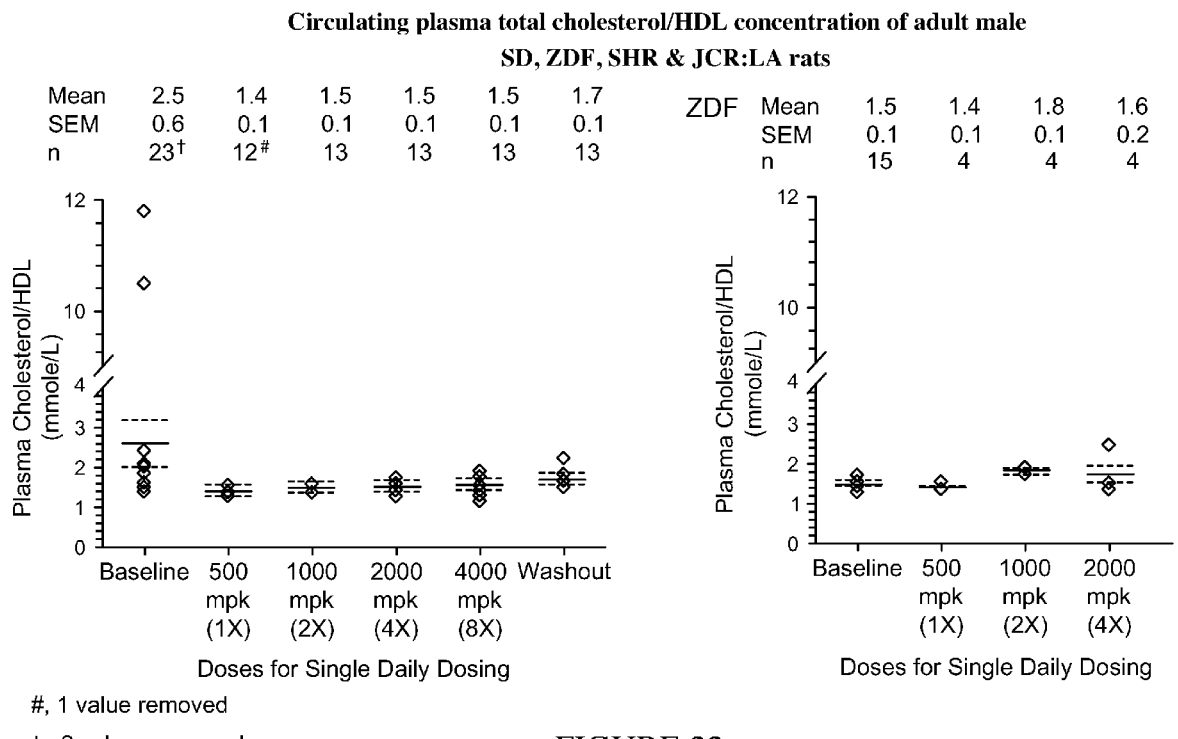
FIG. 22 depicts circulating plasma total cholesterol/HDL concentration of adult male SD, ZDF, SHR and JCR:LA rats.
Figure 23:
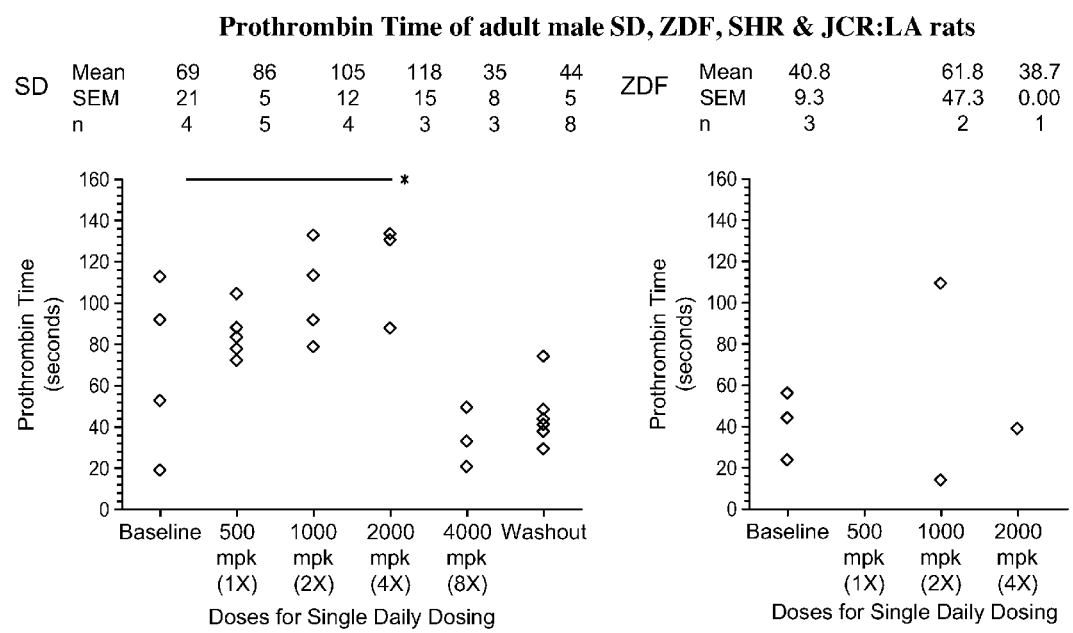
FIG. 23 depicts prothrombin time of adult male SD, ZDF, SHR and JCR:LA rats.
Figure 24:
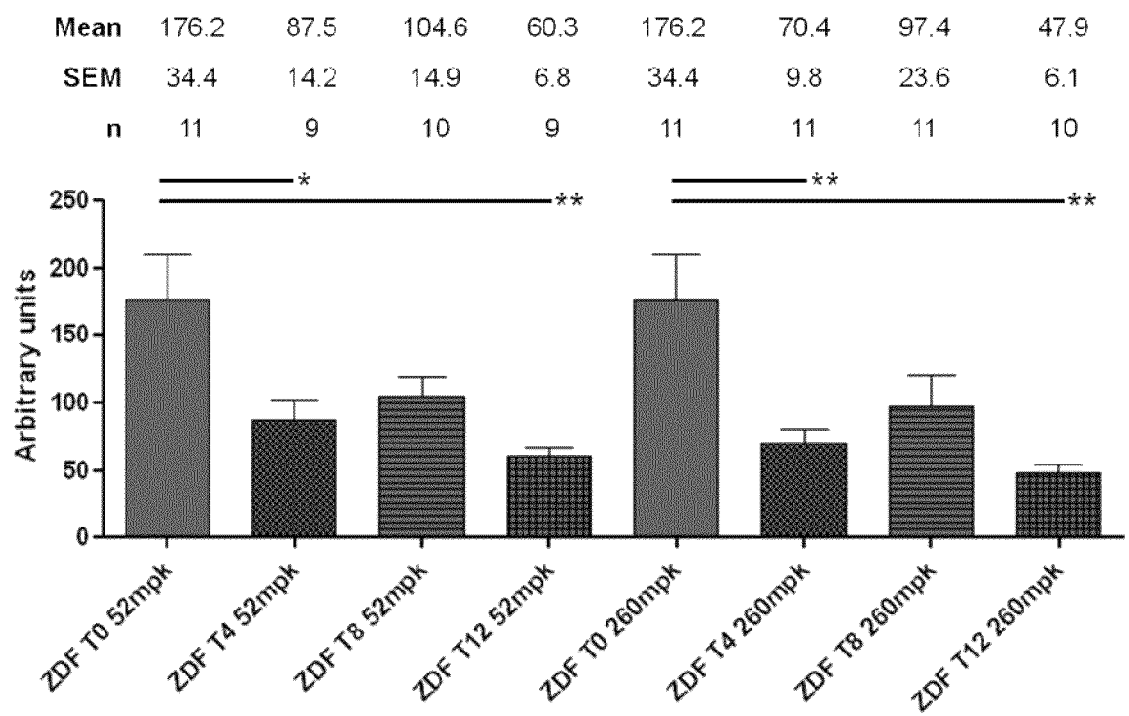
FIG. 24 depicts OGTT area under the curve data in ZDF male rats treated with Composition 3 for 28 days.
Figure 25:
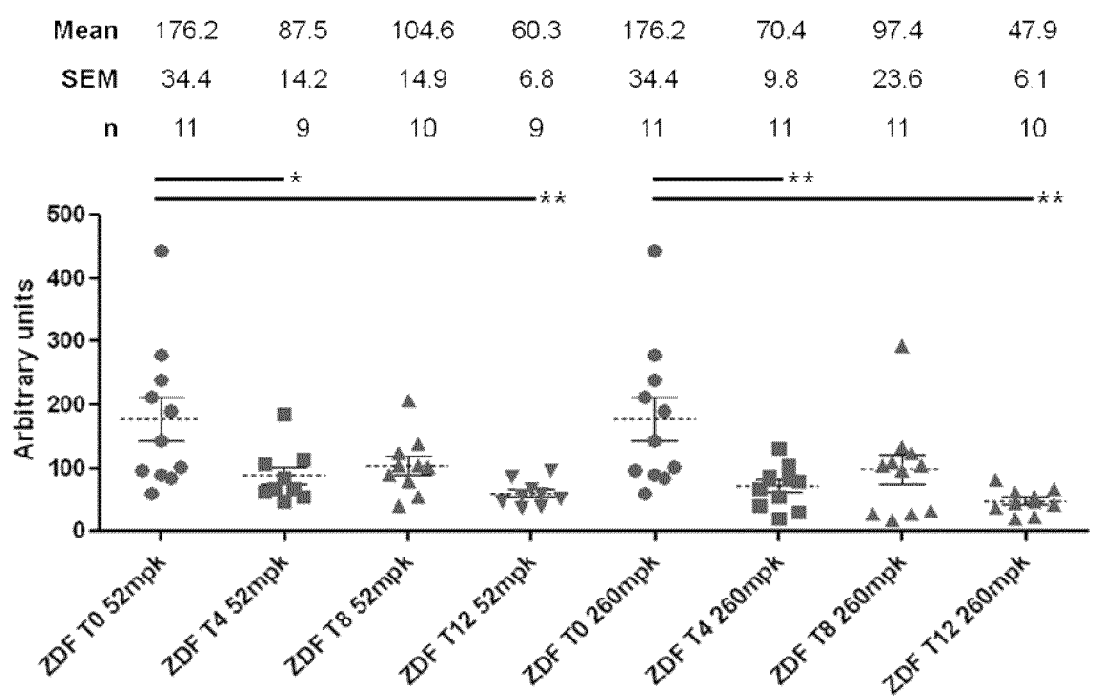
FIG. 25 depicts OGTT area under the curve data in ZDF male rats treated with Composition 3 for 28 days.
Figure 26:
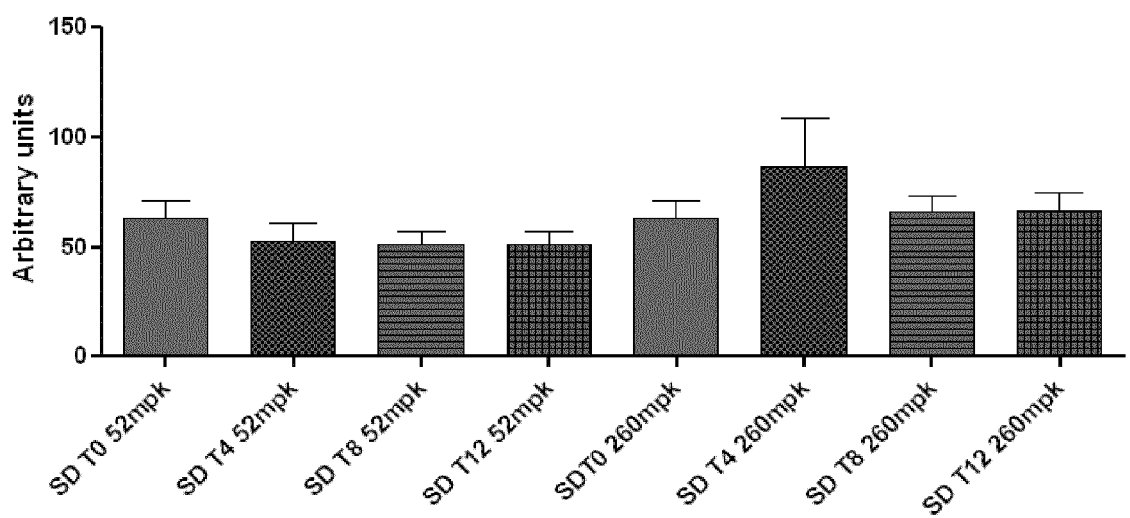
FIG. 26 depicts OGTT area under the curve data in SD male rats treated with Composition 3 for 28 days.
Figure 27:
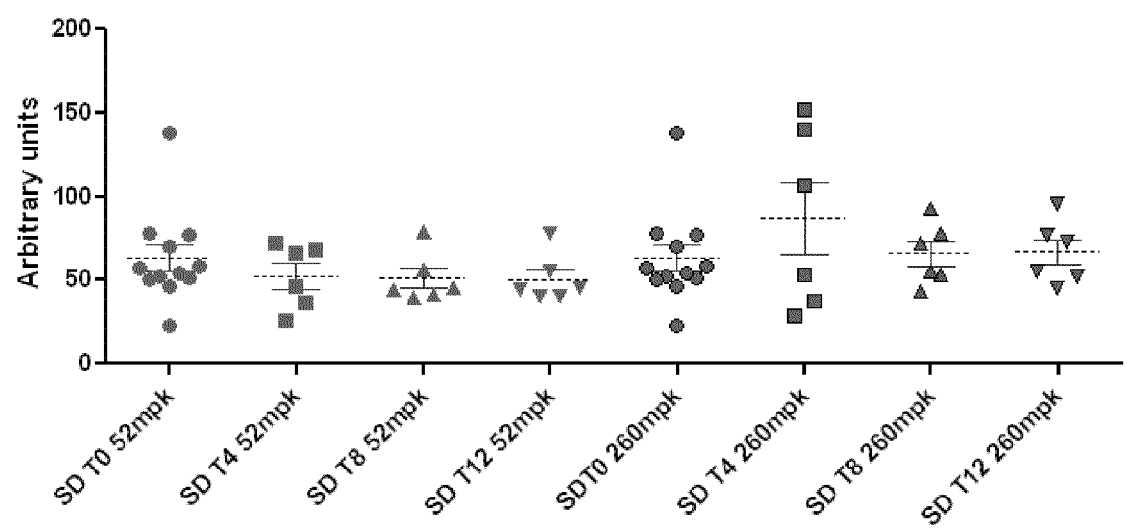
FIG. 27 depicts OGTT area under the curve data in ZDF male rats treated with Composition 3 for 28 days.
Figure 28:
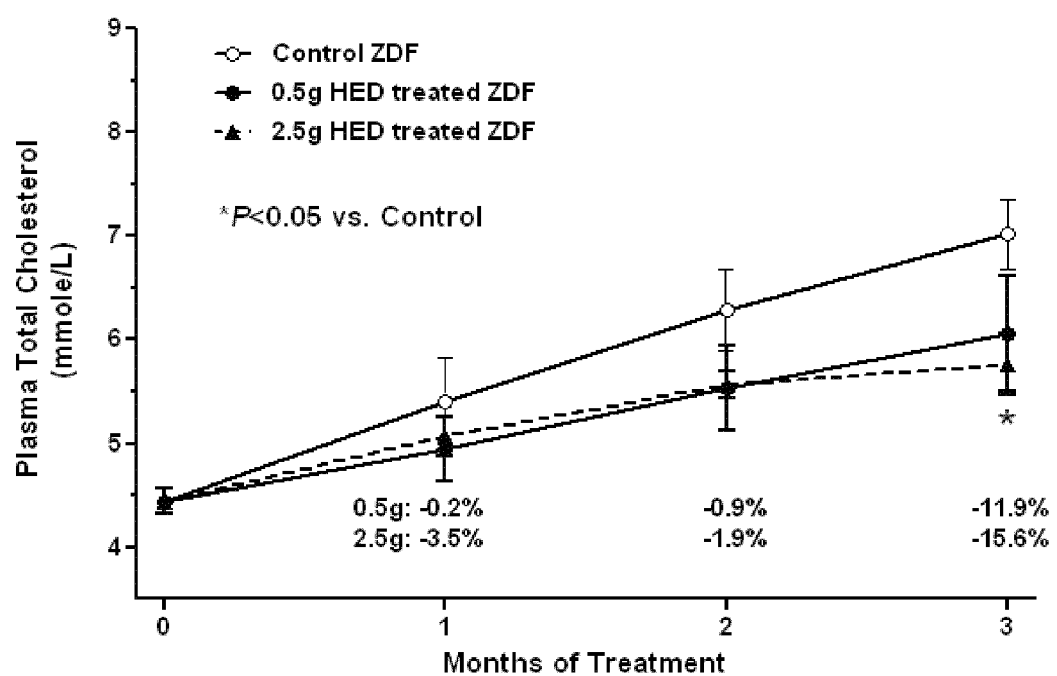
FIG. 28 depicts the effects of Composition 3 on plasma total cholesterol in male ZDF rats compared to age-matched controls.
Figure 29:
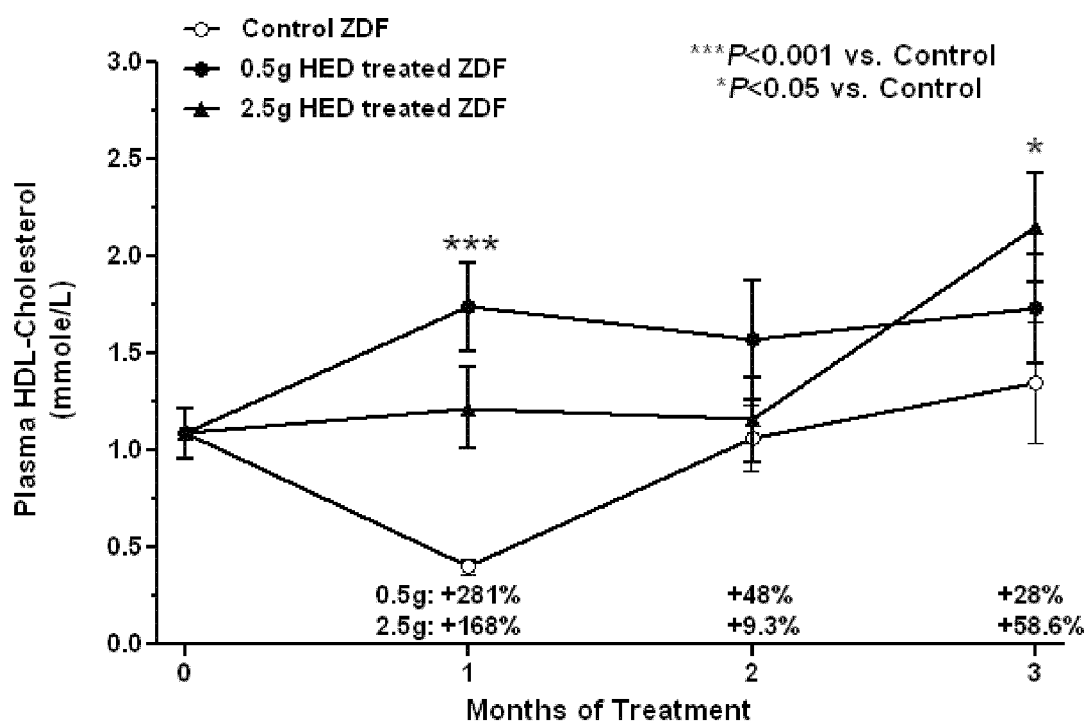
FIG. 29 depicts the effects of Composition 3 on plasma HDL-cholesterol in male ZDF rats compared to age-matched controls.
Figure 30:
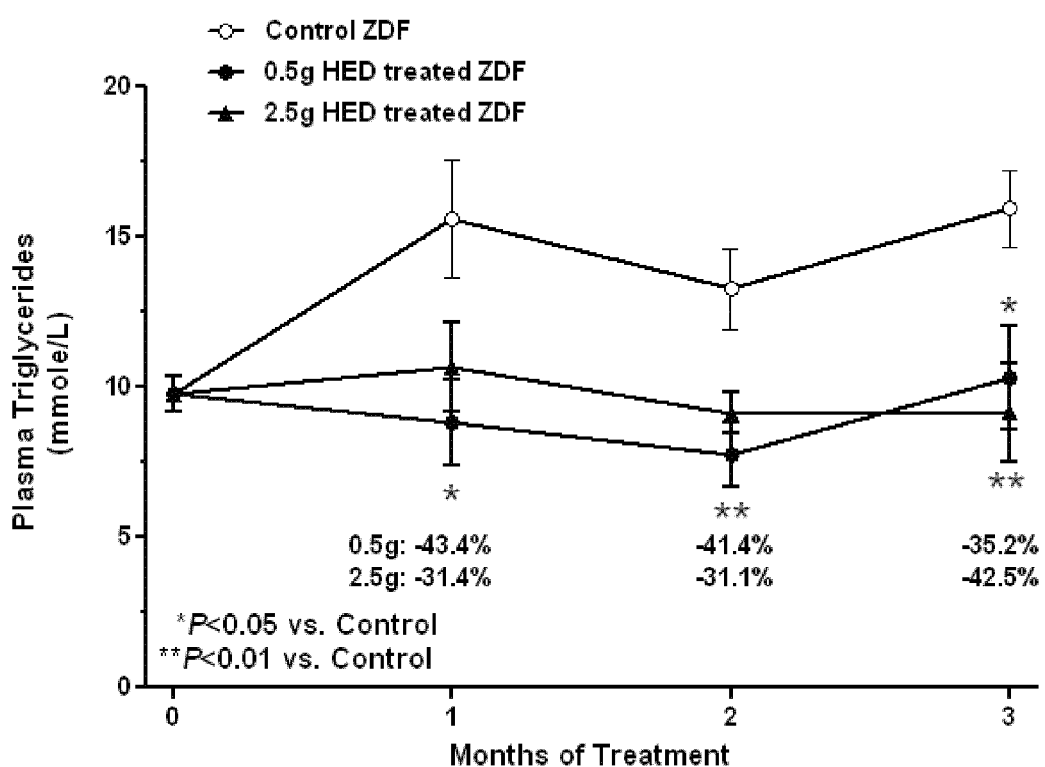
FIG. 30 depicts the effects of Composition 3 on plasma triglycerides in male ZDF rats compared to age-matched controls.
Figure 31:
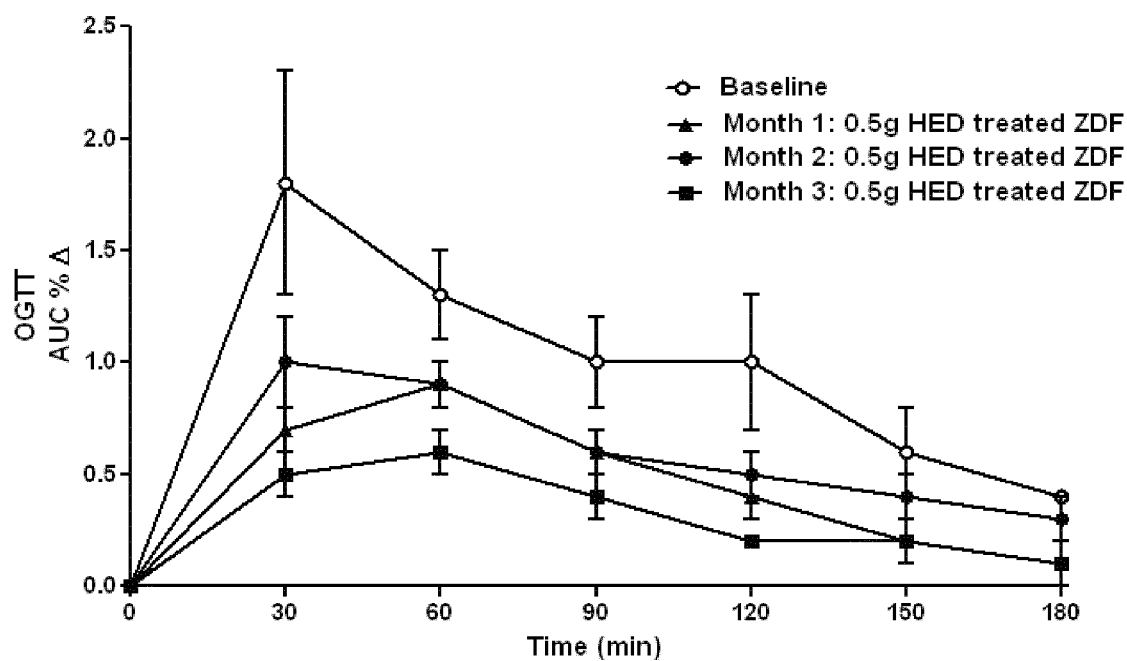
FIG. 31 depicts the effects of Composition 3 on glucose intolerance in male ZDF rats.
Figure 32:
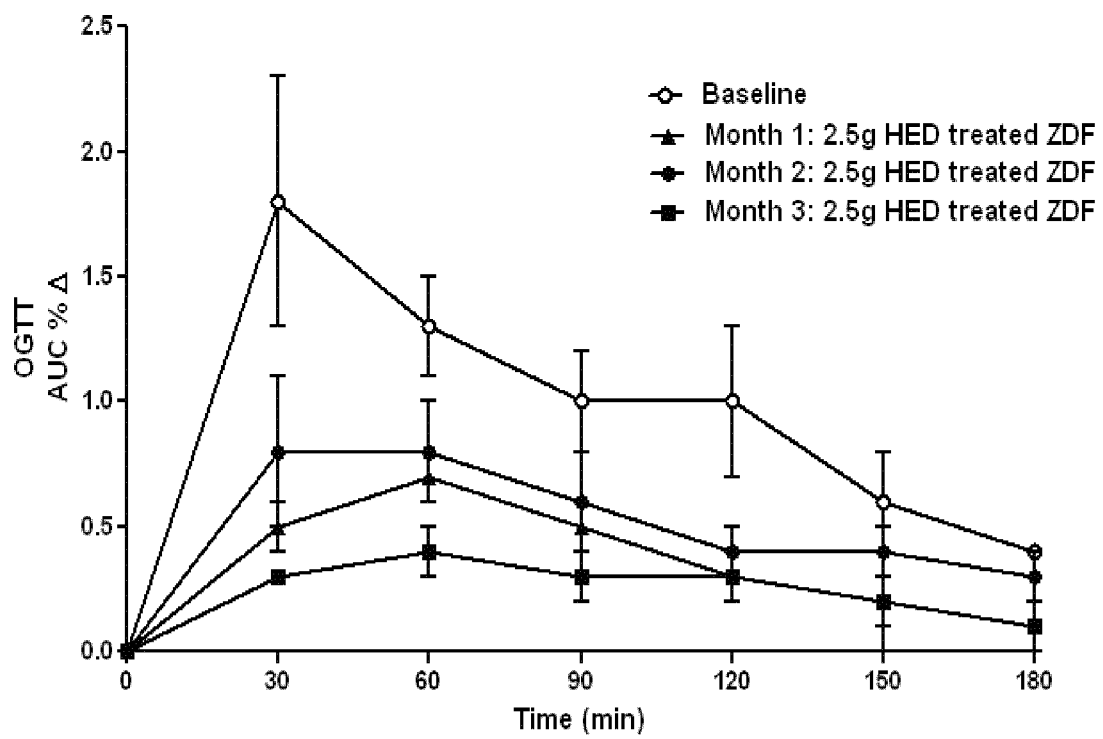
FIG. 32 depicts the effects of Composition 3 on glucose intolerance in male ZDF rats.
Figure 33:
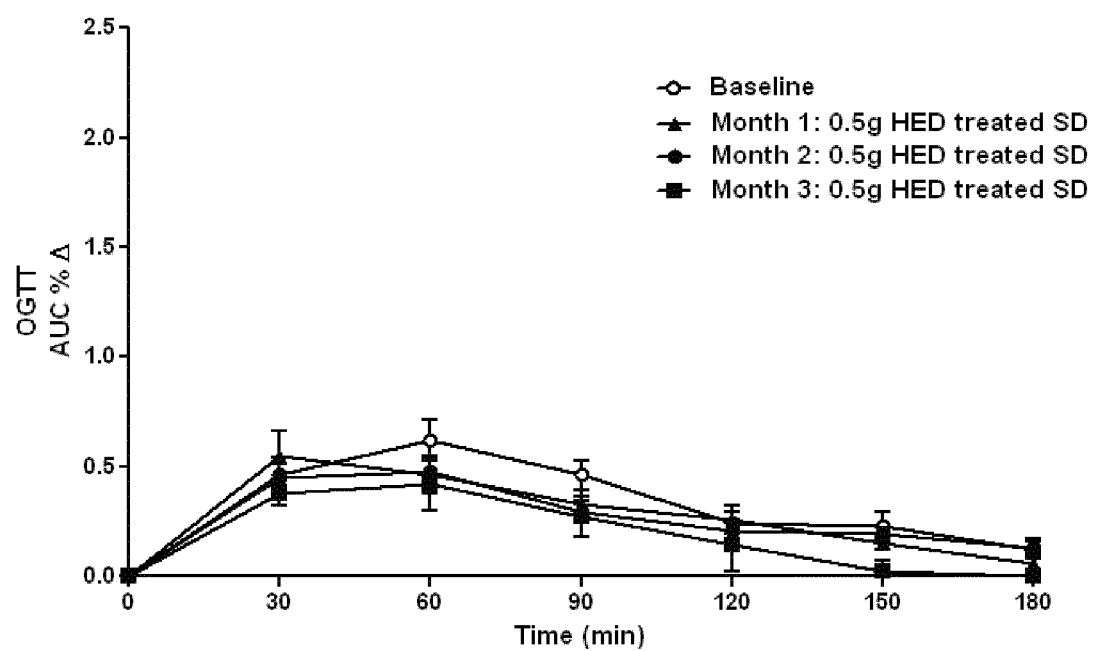
FIG. 33 depicts the effects of Composition 3 on glucose intolerance in male SD rats.
Figure 34:
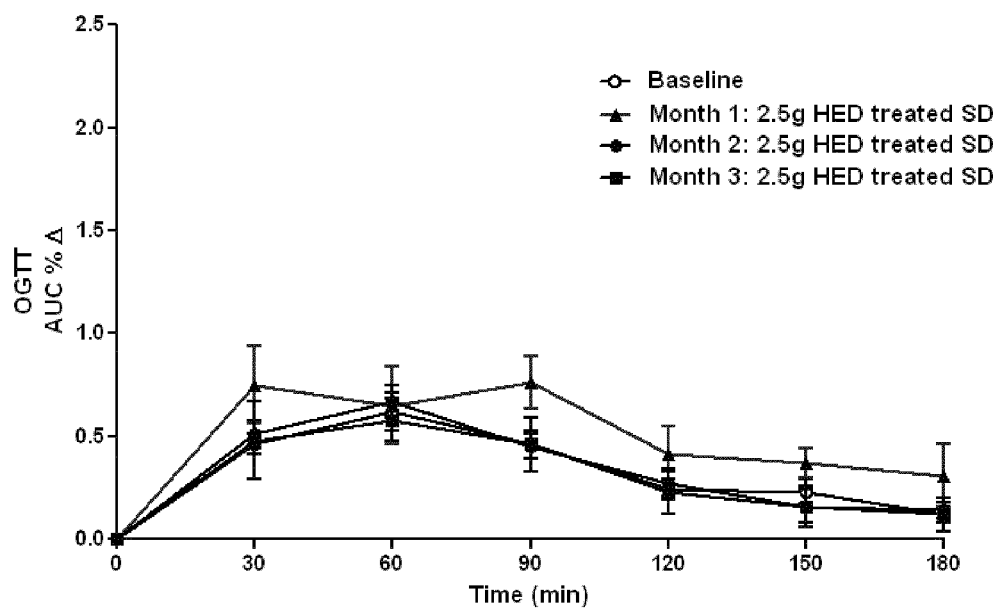
FIG. 34 depicts the effects of Composition 3 on glucose intolerance in male SD rats.

The profile of plasma lipids concentrations (mg/dL) in the above-three untreated adult male murine models were as reported in the literature: Total cholesterol (TC): 71.1±3.3 vs 215.3±10.4 vs 50.3±1.3; triglycerides (TGs): 59.5±4.5 vs 65.1±3.8 vs 53.0±12.9; low-density lipoprotein (LDL): 13.3±1.2 vs 101.6±6.7 vs 12.2±1.6; high-density lipoprotein (HDL): 53.4±3.2 vs 88.8±3.6 vs 24.8±2.6. Six (6) weeks of QD treatment with Composition 3 (104 vs 208 vs 417 mg/kg (Human equivalent dosing of 500, 1,000 and 2,000 mg/day) in C57BL6 led to significant dose-dependent decrease in plasma TGs (up to 60%), reduced LDL (up to 28%), elevated HDL (by 17%) but did not affect TC (see FIGS. 2-12 and Table 1). In severely dyslipidemic LDLr-KO mice, Composition 3 led to significant dose-dependent decrease in plasma TGs, elevated further HDL, caused a slight elevation in TC (only at mid-dose) and did not affect LDL (see FIGS. 13-17 and Table 1). In hApoA-I transgenic mice, Composition 3 led to significant decrease in plasma TGs, elevated HDL and did not affect TC (see FIG. 18 and Table 1). The liver concentrations of TC were the same in all three phenotypes but TGs were reduced (19%; $p<0.05$) in LDLr-KO and elevated (153%; $p<0.01$) in hApoA-I, compared to control C57BL6. Treatment with Composition 3 elevated liver TC and TGs by up to 12% and 27%, respectively, in C57BL6, by up to 10% and 36% in LDLr-KO and by up to 10% for TC but mixed effects for TGs (−13 to +12%) in hApoA-I mice, respectively (see Table 2).

TABLE 1

Effects mediated by 6-weeks treatment with Composition 3 on plasma lipids.

| Murine phenotype | Plasma Lipids | Low dose 104 mg/kg (HED: 500 mg/day) | Mid-dose 208 mg/kg (HED: 1000 mg/day) | High-dose 417 mg/kg (HED: 2000 mg/day) |
|---|---|---|---|---|
| C57BL6 | TC | 75.9 ± 2.0 up 6.8% (NS) | 80.6 ± 3.3 up 13.4% (NS) | 78.1 ± 2.7 up 9.8% (NS) |
|  | TGs | 32.2 ± 1.6 down 46% ($p < 0.001$) | 26.0 ± 2.8 down 56% ($p < 0.001$) | 23.8 ± 1.2 down 60% ($p < 0.001$) |
|  | LDL | 11.1 ± 1.4 down 15% (NS) | 11.2 ± 1.0 down 16% ($p \leq 0.05$) | 9.6 ± 0.7 down 28% ($p < 0.05$) |
|  | HDL | 59.4 ± 1.9 up 11% (NS) | 63.4 ± 3.5 up 19% (NS) | 62.3 ± 2.4 up 17% ($p < 0.05$) |
| LDLr-KO | TC | 219.3 ± 7.4 up 2% (NS) | 244.4 ± 7.9 up 14% ($p < 0.01$) | 238.5 ± 6.9 up 11% (NS) |
|  | TGs | 45.7 ± 2.8 down 30% ($p < 0.001$) | 41.7 ± 4.9 down 36% ($p < 0.01$) | 36.7 ± 1.6 down 44% ($p < 0.001$) |
|  | LDL | 99.2 ± 5.7 down 2% (NS) | 116.2 ± 4.4 up 14% (NS) | 97.4 ± 6.5 down 4% (NS) |
|  | HDL | 90.9 ± 2.5 up 2% (NS) | 88.4 ± 4.6 = (NS) | 111.2 ± 2.5 up 25% ($p < 0.001$) |
| hApoA-I transgenic | TC | 51.1 ± 1.5 up 2% (NS) | 57.2 ± 2.6 up 14% ($p < 0.05$) | 50.1 ± 1.4 = (NS) |
|  | TGs | 19.3 ± 2.8 down 64% ($p < 0.05$) | 43.2 ± 11.7 down 18% (NS) | 43.0 ± 8.2 down 19% (NS) |
|  | LDL | 10.8 ± 1.0 down 11% (NS) | 12.8 ± 2.3 = (NS) | 13.9 ± 1.0 up 14% (NS) |
|  | HDL | 27.9 ± 2.4 up 13% (NS) | 28.6 ± 2.6 up 15% (NS) | 21.6 ± 12.8 down 13% (NS) |

NS; not significant

TABLE 2

Plasma lipids at baseline between murine phenotype

| Plasma concentrations (mg/dL) | C57BL6 control | LDLr-KO | Variation vs control | hApoA-I transgenic | Variation vs control |
|---|---|---|---|---|---|
| total cholesterol (TC) | 71.1 ± 3.3 | 215.3 ± 10.4 | up 3-fold $p < 0.001$ | 50.3 ± 1.3 | down 29.3% NS |
| triglycerides (TGs) | 59.5 ± 4.5 | 65.1 ± 3.8 | up 9.4% NS | 53.0 ± 12.9 | down 10.9% NS |
| low density lipoprotein (LDL-C) | 13.3 ± 1.2 | 101.6 ± 6.7 | up 7.6-fold $p < 0.001$ | 12.2 ± 1.6 | down 8.3% NS |
| high-density lipoprotein (HDL-C) | 53.4 ± 3.2 | 88.8 ± 3.6 | up 166% $p < 0.001$ | 24.8 ± 2.6 | down 54% $p < 0.001$ |
| Liver concentrations (µg/mg) |  |  |  |  |  |
| total cholesterol (TC) | 23.1 ± 0.8 | 23.6 ± 0.6 | = (NS) | 25.1 ± 0.5 | up 9% (NS) |
| triglycerides (TGs) | 53.0 ± 3.1 | 42.9 ± 2.1 | down 19% $p < 0.05$ | 81.3 ± 7.4 | up 153% $p < 0.001$ |

NS; not significant

These data indicate that the Composition 3 is an effective modulator of lipid metabolism, mainly at reducing plasma TGs and LDL and elevating HDL. These data indicate that in some embodiments, concentrated therapeutic phospholipid compositions can be effective as a therapy against moderate to severe hypertriglyceridemia. In some embodiments, concentrated therapeutic phospholipid compositions in combination with other anti-dyslipidemic agents can be effective at lowering refractory hypertriglyceridemia.

Example 2

Increase of the Circulating Plasma Concentration of High-Density Lipoprotein-Cholesterol (HDL-C) and Reduced Total Cholesterol (TC)/HDL Ratio in 12-Week Old Male Zucker Diabetic Fatty Rats The purpose of this study was to examine the effects of the concentrated therapeutic phospholipid compositions in the Zucker Diabetic Fatty rat rodent model for type 2 diabetes with obesity, hyperlipidaemia and insulin resistance (ZDF; Gmi-fa/fa) vs age-/sex-matched normal healthy non-obese normoglycemic lean control SD rat (from Charles River Labs; 12-w, 359±17 vs 439±13 gr.; n=9-12/gr.). Lipid profile (total cholesterol (TC), triglycerides (TGs), High-Density Lipoprotein-Cholesterol (HDL-C) and TC/HDL ratio were assessed before, 1 and 2 month after QD treatment with Composition 3 (52 versus 260 mg/kg (HED of 500 and 2,500 mg), and kept according to local and national ethic regulations (Formulab high fat 5008 (ZDF) vs normal 5001 (SD) diet regime and water ad libitum). Data are presented as Mean±SD (n=2-10) and statistical differences calculated by unpaired two-tailed t test (v5-GraphPad Prism). At 12-w of age, the circulating plasma concentrations of TC, TGs, HDL and TC/HDL ratio were: 4.6±0.9, 11.6±5.9, 2.3±1.1 mmol/L and 2.16±0.62, respectively. Lipids' profile in SD rats were significantly lower at 1.9±0.4, 1.2±0.4, 1.3±0 2 mmol/L and 1.45±0.11, respectively. Daily low and high dose treatment for 60 days did not affect TC and TGs concentrations but increased by 1.7- to 1.8-fold (p<0.01) "good" HDL-cholesterol and decreased the TC/HDL ratio by 26-32% (p<0.01-0.05), respectively.

Example 3

Improved Glucose Intolerance in Zucker Diabetic Fatty Rats after Administration of Composition 3

The purpose of this study was to investigate the effects of Composition 3 in an overtly dyslipidemic, obese, type 2 diabetic rat model. Zucker Diabetic Fatty (ZDF; Gmi-fa/fa) rats were used versus age-/sex-matched normal healthy non-obese normoglycemic lean control SD rat (from Charles River Labs; 12-w, 359±17 vs. 439±13 gr.; n=9-12/gr.). Glucose intolerance was assessed conducting an oral glucose tolerance test (OGTT; overnight fasting then single gavage of glucose 2 g/kg rat b.w.) over 180 minutes using glucometer strips (Accu-Chek Aviva, Roche Diagnostics), before and 90 days after treatment with Composition 3 given by QD gavage at 52 versus 260 mg/kg (HED of 500 and 2,500 mg), and kept according to local and national ethic regulations (Formulab high fat 5008 (ZDF) vs normal 5001 (SD) diet regime and water ad libitum). Data are presented as Mean±SD and statistical differences calculated by unpaired two-tailed t test (v5-GraphPad Prism).

At 12-w of age ($T_0$) fasting circulating plasma concentrations of glucose were 7.8±2.1 vs 5.0±0.6 mmol/L (p<0.001) in untreated ZDF vs SD rats. Non-fasting ZDF and SD rats glucose levels were 22.0±4.2 vs 8.6±0.6 mmol/L, respectively. One month later, baseline values increased by 1.9-fold (p<0.0001) in fasted ZDF while remaining unchanged in fasted SD. Aging did not affect glucose levels in non-fasted rats. Glucose challenge led to a maximum 2.5-fold (p<0.0001) and 1.6-fold (p<0.0001) increase in plasma glucose concentrations in untreated fasted ZDF and SD, at 30 and 60 minutes, respectively, returning mostly to initial values after 180 mins. At 16 weeks of age, thirty days ($T_{30}$) of treatment did not affect either the profile (AUC) or maximum elevation in glucose in SD rats but treatment of ZDF shifted to the right the maximum elevation in plasma glucose (from 30 to 60 minutes), reduced by 61-72% (p<0.02) the peak elevation at 30 minutes and reduced by 50-60% (p<0.0001) the AUC at either doses of Composition 3, thus back to the AUC observed in untreated glucose challenged SD rats. At 20 weeks of age, 60 days of treatment, either dosing did not further attenuate glucose intolerance. None of the treatment profile affected the plasma and urinary concentrations of glucose (hyperglycemia and glucosuria) in non-fasted ZDF or SD. These data indicate that a short term and low dose chronic administration of Composition 3 significantly improves glycemic control in a model of severe hyperglycemia.

Example 4

A Randomized, Placebo-Controlled, Double-Blind, Dose-Ranging and Multi-Centered Trial to Evaluate the Safety and Efficacy of Concentrated Therapeutic Phospholipid Compositions in the Treatment of Moderate Hypertriglyceridemia Subjects with moderate hypertriglyceridemia treated by physician according to the Canadian Lipid Treatment Guidelines who are treated over 12 weeks with concentrated phospholipid given at doses of 1.0, 2.0 or 4.0 g. The primary measure of efficacy will be the percent change in fasting blood circulating serum triglycerides (TGs) between baseline (Week 1) and 12 weeks of treatment. Secondary Outcomes: between baseline and after six weeks and 12 weeks of treatment: 1) absolute change in fasting plasma TGs; 2) percentage (%) of subjects achieving target TG fasting plasma levels; 3) absolute change in fasting plasma LDL-C, VLDL-C, HDL-C, HDL2-C, HDL3-C, Total Cholesterol, hs-CRP and non-HDL; 4) percentage (%) change in fasting plasma concentrations of LDL-C, VLDL-C, HDL-C, HDL2-C, HDL3-C, TC, hs-CRP and non-HDL; 5) calculated Ratios: a) total cholesterol:HDL-C; b) LDL-C:HDL-C; c) TGs: HDL-C; 6) LDL-C-related parameters: a) particle number; b) particle size; c) oxidation; 7) absolute and percent (%) change in fasting plasma concentrations of biomarkers; a) glycated Hemoglobin (HbA1c), b) apolipoprotein A-I (ApoA-I), c) apolipoprotein B-100 (ApoB-100), d) apolipoprotein E (ApoE), e) lipoprotein(a) (Lp(a)), f) adiponectin, g) glucose, h) insulin; 8) calculated ApoB:ApoA-I ratio; 9) fasting plasma lipoprotein-associated phospholipase A2 activity (Lp-PLA2); 10) HOMA-IR (homeostasis model assessment of insulin resistance: [glucose (mmol/L)×IRI (microIU/L)/22.5]; 11) plasma concentrations of total EPA and DHA (PK/PD—25 subjects/group); 12) OM31 (Omega-3 index); 13) Subjects Genetic Polymorphism: a) Lecithin:Cholesterol Acyltransferase (LCAT), b) cholesteryl ester transfer protein (CETP), c) scavenger receptor type B-1 (SR-B1), d) ATP Binding Cassette transporter 1 (ABCA1).

Example 5

Preclinical Non-GLP Assessment of Efficacy of Concentrated Therapeutic Phospholipid Compositions Alone or in Combination with a Statin on Modulating Blood Lipids and the Development of Atherosclerotic Lesions in ApoE Null Mice Fed a Western-Type Diet Male adult mice (n=135 (15 mice/group) 5-6 weeks of age) weighing about 18-20 g each homozygous for the Apoetm1Unc mutation are administered HOW either Vehicle (Water or 0.2%-0.5% Carboxymethylcellulose); composition 3 (1,000 mg/daily HED); composition 3 (2,000 mg/daily HED); or Lipitor (20 mg/daily HED); or composition 3 (1,000 mg/daily HED)+Lipitor (20 mg/daily HED). At 0, 3 months, or 6 months the following assessment of values is made relative to: blood Lipids: TC, TGs, LDL, HDL, non-HDL, VLDL (0, 3 and 6 months) (2) Aortic Atherosclerosis (0, 3 and 6 months): a. Thoracic and abdominal aorta will be isolated, trimmed of fat, laid out and pinned on black matrix for photography, and stained with Sudan IV or Oil Red-O. b. Vessel will be imaged for surface involvement using a computerized image analysis system (Image ProPlus or NIH Package Software). The data will be computed by group and statistically analyzed. c. Lipid extraction: Following staining and morphometric analysis, aortas will be extracted (Bligh/Dyer). (3) Red blood cells Omega-3 Index (0, 3 and 6 months); (4) Circulating plasma concentration of CRP (0, 3 and 6 months).

Example 6

Comparison of Composition 3 with Lovaza® on the Omega 3 Index

Figure 35:
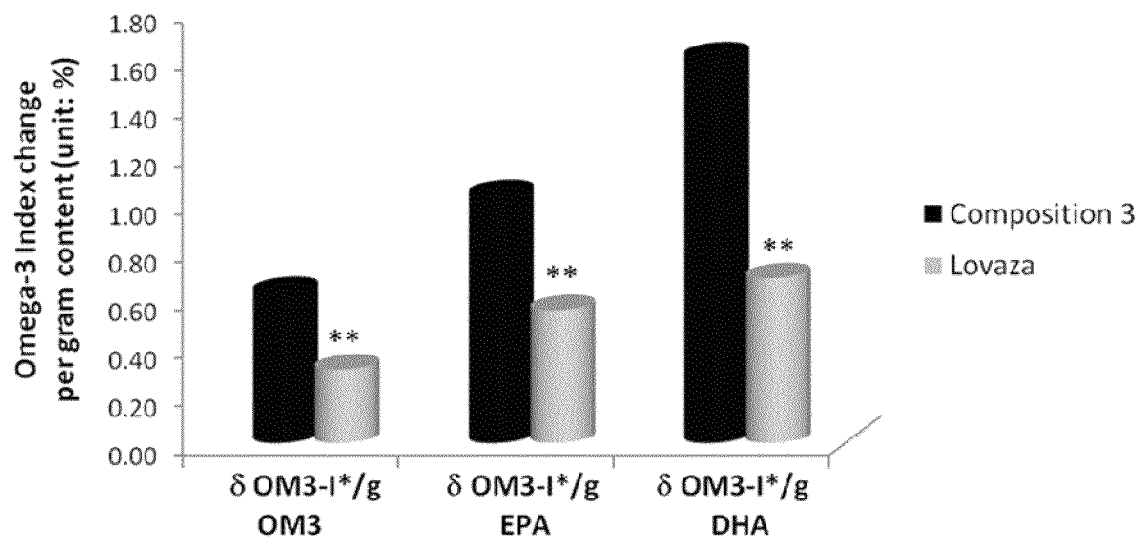
FIG. 35 depicts the comparative effects of Composition 3 and Lovaza® on the Omega-3 Index.

Male adult (14 weeks) Sprague-Dawley (SD) rats with an average body weight of >375-425 were fed normal rat chow (diet 5075—normal, standard rat chow). Number of test subjects/group: n=56; n=8 rats/gr. Dosing was QD (single daily dosing/morning) for 12 weeks with either (i) Vehicle (ii) Composition 3, 52 mpk ("milligrams per kilogram") (500 mg/day HED ("Human Effective Dose")); (iii) Composition 3, 104 mpk (1000 mg/day HED); (iv) Composition 3, 416 mpk (4000 mg/day HED); (v) Lovaza®, 416 mpk (4000 mg/day HED). Results are shown in FIG. 35.

Example 7

Montherapy Study of Concentrated Phospholipids in Early Stage Alzheimer's Disease Subjects will be randomly assigned to receive either concentrated therapeutic phospholipid composition 1 g, fish oil (135 mg EPA: 108 mg DHA) 1 g, or placebo (soy oil) 1 g once daily. The primary outcome measure will be the change in NTB between baseline and 24 weeks of treatment. The Neuropsychological Test Battery (NTB) will be used to monitor and evaluate important cognitive changes. The following 9 components of the NTB are used to determine the outcome for the subject: (1) Wechsler Memory Scale, visual immediate (score range, 0-18), (2) Wechsler Memory Scale verbal immediate (score range, 0-24), (3) Rey Auditory Verbal Learning, Test (RAVLT) immediate (score range, 0-105), (4) Wechsler, Memory Digit Span (score range, 0-24), (5) Controlled Word Association, Test (COWAT), (6) Category Fluency Test (CFT), (7) Wechsler, Memory Scale visual delayed (score range, 0-6), (8) Wechsler, Memory Scale verbal delayed (score range, 0-8), and (9) RAVLT, delayed (score range, 0-30) (Harrison et al. 2007). The RAVLT delayed measure is composed of delayed recall and recognition performance components that are summed to yield a score ranging from 0 to 30, yielding 9 measures of subject performance. Secondary outcome measures will include the change in the NPI and DAD at 24 weeks of treatment. The NPI evaluates 12 neuropsychiatric disturbances common in dementia: delusions, hallucinations, agitation, dysphoria, anxiety, apathy, irritability, euphoria, disinhibition, aberrant motor behaviour, night-time behaviour disturbances, and appetite and eating abnormalities. The DAD is a caregiver-based interview instrument used to evaluate instrumental and basic activities of daily living in dementia (hygiene, dressing, undressing, continence, eating, meal preparation, telephoning, going on an outing, finance, correspondence, medication, leisure and housework). The NPI also assesses the amount of caregiver distress engendered by each of the neuropsychiatric disorders. Blood is drawn and levels of EPA, DHA and phopsholipids is measured.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method for reducing serum triglyceride levels comprising administering to a subject in need thereof an effective amount of a concentrated therapeutic phospholipid composition wherein:

the composition comprises compounds of the Formula I:

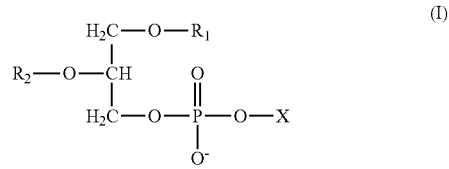

$R_1$ and $R_2$ each independently represent a docosahexaenoic acid (DHA) or an eicosapentaenoic acid (EPA) residue;
each X is independently selected from —$CH_2CH_2NH_3$, —$CH_2CH_2N(CH_3)_3$ or

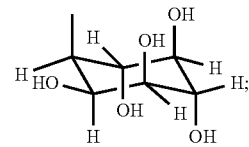

the total phospholipids in the composition are at a concentration of about 66% (w/w); the composition comprises omega-3 fatty acids in an amount of at least 15% w/w; and the composition is suitable for human consumption.

2. The method of claim 1, wherein the composition is contained in a capsule.

3. The method of claim 1, wherein the composition further comprises triglycerides in a concentration of below about 5%.

4. The method of claim 1, wherein the composition further comprises an antioxidant.

5. The method of claim 4, wherein the antioxidant is astaxanthin.

6. A method for reducing serum triglyceride levels comprising administering to a subject in need thereof a capsule comprising an effective amount of a concentrated krill oil extract
wherein:
the extract comprises compounds of the Formula I:

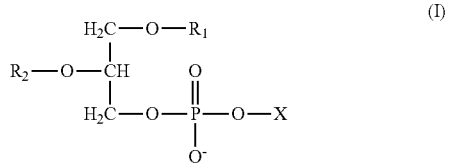

$R_1$ and $R_2$ each independently represent a docosahexaenoic acid (DHA) or an eicosapentaenoic acid (EPA) residue;
each X is independently selected from —CH$_2$CH$_2$NH$_3$, —CH$_2$CH$_2$N(CH$_3$)$_3$ or

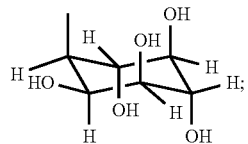

the total phospholipids in the extract are at a concentration of about 66% (w/w);
the extract comprises astaxanthin;
the extract comprises omega-3 fatty acids in an amount of at least 15% w/w; and
the extract is suitable for human consumption.

7. A method for treating hypertriglyceridemia comprising administering to a subject in need thereof an effective amount of a concentrated therapeutic phospholipid composition
wherein:
the composition comprises compounds of the Formula I:

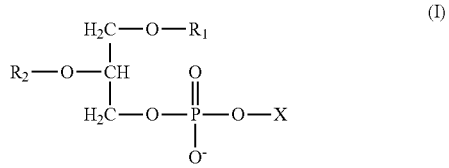

$R_1$ and $R_2$ each independently represent a docosahexaenoic acid (DHA) or an eicosapentaenoic acid (EPA) residue;
each X is independently selected from —CH$_2$CH$_2$NH$_3$, —CH$_2$CH$_2$N(CH$_3$)$_3$ or

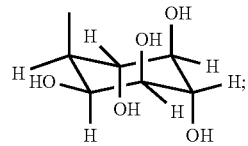

the total phospholipids in the composition are at a concentration of about 66% (w/w); the composition comprises omega-3 fatty acids in an amount of at least 15% w/w; and the composition is suitable for human consumption.

8. The method of claim 7, wherein the composition is contained in a capsule.

9. The method of claim 7, wherein the composition further comprises triglycerides in a concentration of below about 5%.

10. The method of claim 7, wherein the composition further comprises an antioxidant.

11. The method of claim 10, wherein the antioxidant is astaxanthin.

12. The method of claim 7, further comprising reducing serum triglyceride levels.

13. A method for treating hypertriglyceridemia comprising administering to a subject in need thereof a capsule comprising an effective amount of a concentrated krill oil extract
wherein:
the extract comprises compounds of the Formula I:

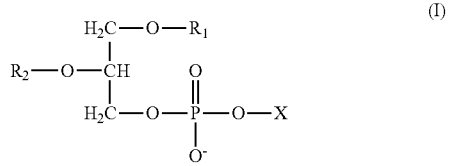

$R_1$ and $R_2$ each independently represent a docosahexaenoic acid (DHA) or an eicosapentaenoic acid (EPA) residue;
each X is independently selected from —CH$_2$CH$_2$NH$_3$, —CH$_2$CH$_2$N(CH$_3$)$_3$ or

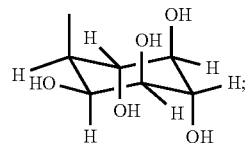

the total phospholipids in the extract are at a concentration of about 66% (w/w);
the extract comprises astaxanthin;
the extract comprises omega-3 fatty acids in an amount of at least 15% w/w; and
the extract is suitable for human consumption.

14. The method of claim 12, further comprising reducing serum triglyceride levels.

* * * * *

UNITED STATES PATENT AND TRADEMARK OFFICE
CERTIFICATE OF CORRECTION

PATENT NO.         : 8,586,567 B2
APPLICATION NO.    : 12/915724
DATED              : November 19, 2013
INVENTOR(S)        : Fotini Sampalis and Henri Harland It is certified that error appears in the above-identified patent and that said Letters Patent is hereby corrected as shown below:

In the Claims:

Claim 14, col. 32, line 58, please correct "claim 12" to:
--claim 13--.

Signed and Sealed this
Twenty-second Day of April, 2014

Michelle K. Lee
*Deputy Director of the United States Patent and Trademark Office*